US009382255B2

(12) United States Patent
Klar et al.

(10) Patent No.: US 9,382,255 B2
(45) Date of Patent: Jul. 5, 2016

(54) SUBSTITUTED PYRROLOPYRIMIDINYLAMINO-BENZOTHIAZOLONES AS MKNK KINASE INHIBITORS

(71) Applicant: BAYER PHARMA AKTIENGESELLSCHAFT, Berlin (DE)

(72) Inventors: Ulrich Klar, Berlin (DE); Lars Wortmann, Berlin (DE); Georg Kettschau, Berlin (DE); Florian Püehler, Wellesley, MA (US); Philip Lienau, Berlin (DE); Kirstin Petersen, Berlin (DE); Andrea Hägebarth, Berlin (DE); Detlev Sülzle, Berlin (DE); Anja Richter, Berlin (DE)

(73) Assignee: BAYER PHARMA AKTIENGESELLSCHAFT, Berlin (DE)

( * ) Notice: Subject to any disclaimer, the term of this patent is extended or adjusted under 35 U.S.C. 154(b) by 0 days.

(21) Appl. No.: 14/429,927

(22) PCT Filed: Sep. 18, 2013

(86) PCT No.: PCT/EP2013/069325
§ 371 (c)(1),
(2) Date: Mar. 20, 2015

(87) PCT Pub. No.: WO2014/044691
PCT Pub. Date: Mar. 27, 2014

(65) Prior Publication Data
US 2015/0239891 A1     Aug. 27, 2015

(30) Foreign Application Priority Data

Sep. 20, 2012   (EP) .................... 12185139

(51) Int. Cl.
| | | |
|---|---|---|
| *A01N 43/90* | (2006.01) | |
| *A61K 31/519* | (2006.01) | |
| *C07D 471/00* | (2006.01) | |
| *C07D 487/00* | (2006.01) | |
| *C07D 491/00* | (2006.01) | |
| *C07D 487/04* | (2006.01) | |
| *C07D 473/00* | (2006.01) | |
| *A61K 45/06* | (2006.01) | |
| *A61K 31/52* | (2006.01) | |
| *A61K 31/5377* | (2006.01) | |
| *C07D 473/34* | (2006.01) | |

(52) U.S. Cl.
CPC ............ *C07D 487/04* (2013.01); *A61K 31/519* (2013.01); *A61K 31/52* (2013.01); *A61K 31/5377* (2013.01); *A61K 45/06* (2013.01); *C07D 473/00* (2013.01); *C07D 473/34* (2013.01)

(58) Field of Classification Search
None
See application file for complete search history.

(56) References Cited

U.S. PATENT DOCUMENTS

| | | | |
|---|---|---|---|
| 3,760,806 | A | 9/1973 | Leeper et al. |
| 5,252,569 | A | 10/1993 | Hajos et al. |
| 6,395,733 | B1 | 5/2002 | Arnold et al. |
| 6,491,683 | B1 | 12/2002 | Dong et al. |
| 2001/0021822 | A1 | 9/2001 | Ayer |
| 2002/0183722 | A1 | 12/2002 | Harper et al. |
| 2003/0180757 | A1 | 9/2003 | McGall et al. |
| 2006/0183761 | A1 | 8/2006 | Ledeboer et al. |
| 2009/0142313 | A1 | 6/2009 | Talling et al. |
| 2009/0286812 | A1 | 11/2009 | Erickson et al. |
| 2011/0160203 | A1 | 6/2011 | Liu et al. |
| 2015/0133425 | A1 | 5/2015 | Kettschau et al. |
| 2015/0152121 | A1 | 6/2015 | Klar et al. |
| 2015/0218173 | A1 | 8/2015 | Wortmann et al. |
| 2015/0252047 | A1 | 9/2015 | Klar et al. |

FOREIGN PATENT DOCUMENTS

| | | |
|---|---|---|
| EP | 1674466 A1 | 6/2006 |
| EP | 1746096 A1 | 1/2007 |
| GB | 1029696 | 5/1966 |
| JP | 2007/084494 A | 4/2007 |
| WO | 97/18212 A1 | 5/1997 |
| WO | 98/23613 A1 | 6/1998 |
| WO | 99/65908 A1 | 12/1999 |
| WO | 02/088138 A1 | 11/2002 |
| WO | 2005/010008 A1 | 2/2005 |
| WO | 2005/047288 A1 | 5/2005 |
| WO | 2005/111135 A1 | 11/2005 |
| WO | 2006/017443 A2 | 2/2006 |

(Continued)

OTHER PUBLICATIONS

Wolff et. al., "Burger's Medicinal Chemistry and Drug Discovery," 5th Ed. Part 1, pp. 975-977 (1995).*
Banker, et. al., (1996), Modern Pharmaceuticals, p. 596.*
Adesso et al., "Gemcitabine triggers a pro-survival response in pancreatic cancer cells through activation of the MNK2/eIF4E pathway," Oncogene, 2013, 31:2848-2857.
Amblard et al., "A new route to acyclic nucleosides via palladium-mediated allylic alkylation and cross-metathesis," Tetrahedron Letters, 2003, 44:9177-9180.

(Continued)

*Primary Examiner* — Jeffrey H Murray
(74) *Attorney, Agent, or Firm* — Resek, Liang & Frank LLP

(57) ABSTRACT

The present invention relates to substituted pyrrolopyrimidinylamino-benzothiazolone compounds of general formula I as described and defined herein, to methods of preparing said compounds, to intermediate compounds useful for preparing said compounds, to pharmaceutical compositions and combinations comprising said compounds and to the use of said compounds for manufacturing a pharmaceutical composition for the treatment or prophylaxis of a disease, in particular of a hyper-proliferative and/or angiogenesis disorder, as a sole agent or in combination with other active ingredients.

9 Claims, No Drawings

(56) References Cited

FOREIGN PATENT DOCUMENTS

| WO | 2006/136402 A1 | 12/2006 |
|---|---|---|
| WO | 2007/023110 A2 | 3/2007 |
| WO | 2007/059905 A2 | 5/2007 |
| WO | 2008/144253 A1 | 11/2008 |
| WO | 2009/134658 A2 | 11/2009 |
| WO | 2010/006032 A1 | 1/2010 |
| WO | 2010/023181 A1 | 3/2010 |
| WO | 2011/104334 A1 | 9/2011 |
| WO | 2011/104337 A1 | 9/2011 |
| WO | 2011/104338 A1 | 9/2011 |
| WO | 2011/104340 A1 | 9/2011 |
| WO | 2011/149827 A1 | 12/2011 |

OTHER PUBLICATIONS

Blagden et al., The biological and therapeutic relevance of mRNA translation in cancer, Nature Reviews/Clinical Oncology, May 2011, 8:280-291.

Braendvang et al., "Efficient and regioselective N-I alkylation of 4-chloropyrazolo[3,4-d)pyrimidine," 2007, 48:3057-3059.

Buxade et al., "The Mnks: MAP kinase-interacting kinases (MAP kinase signal-integrating kinases)," Frontier in Bioscience, May 1, 2008, 5359-5374.

Chrestensen et al., "Loss of MNK function sensitizes fibroblasts to serum-withdrawal induced apoptosis," Genes to Cells, 2007, 12:113-1140.

Chrestensen et al., "MNK1 and MNK2 Regulation in HER2-overexpressing Breast Cancer Lines," Journal of Biological Chemistry, Feb. 16, 2007, 282(7):4243-4252.

Jauch et al., "Crystal Structures of the Mnk2 Kinase Domain Reveal an Inhibitory Conformation and a Zinc Binding Site," Structure, Oct. 2005, 13:1559-1568.

Jauch et al., "Mitogen-activated protein kinases interacting kinases are autoinhibited by a reprogrammed activation segment," The EMBO Journal, 2006, 25:4020-4032.

Konicek et al., "Therapeutic Inhibition of MAP Kinase Interacting Kinase Blocks Eukaryotic Initiation Factor 4E Phosphorylation and Suppresses Outgrowth of Experimental Lung Metastases," American Association for Cancer Research, Oct. 13, 2015, 1849-1857.

Konicek et al., "Targeting the eIF4F translation initiation complex for cancer therapy," Cell Cycle, Aug. 15, 2008, 7 (16):2466-2471.

Seela et al., "7-Functionalized 7-deazapurine β-D and β-L-ribonucleosides related to tubercidin and 7-deazainosine: glycosylation of pyrrolo[2,3-d]pyrimidines with 1-0-acetyl-2,3,5-tri-O-benzoyl-β-D or β-L-ribofuranose," Tetrahedron, 2007, 63:9850-9861.

Shi et al., "MNK kinases facilitate c-myc IRES activity in rapamycin-treated multiple myeloma cells," Oncogene, 2013, 32:190-197.

Sizun et al., "Synthesis of the first example of a nucleoside analogue bearing a 5'-deoxy-β-D-allo-septanose as a seven-membered ring sugar moiety," Carbohydrate Research, 2009, 344:448-453.

Ueda et al. "Mnk2 and Mnk1 Are Essential for Constitutive and Inducible Phosphorylation of Eukaryotic Initiation Factor 4E but Not for Cell Growth or Development," Molecular and Cellular Biology, Aug. 2004, 24(15):6539-6549.

Wendel et al., "Dissecting eIF4E action in tumorigenesis," Genes & Development, 2007, 21:3232-3237.

Yoshizawa et al., "Overexpression of Phospho-eIF4E is Associated with Survival through AKT Pathway in Non-Small Cell Lung Cancer," Clinical Cancer Research, Jan. 1, 2010, 16(1):240-248.

\* cited by examiner

SUBSTITUTED PYRROLOPYRIMIDINYLAMINO-BENZOTHIAZOLONES AS MKNK KINASE INHIBITORS

The present invention relates to substituted pyrrolopyrimidinylamino-benzothiazolone compounds of general formula I as described and defined herein, to methods of preparing said compounds, to intermediate compounds useful for preparing said compounds, to pharmaceutical compositions and combinations comprising said compounds and to the use of said compounds for manufacturing a pharmaceutical composition for the treatment or prophylaxis of a disease, in particular of a hyperproliferative and/or angiogenesis disorder, as a sole agent or in combination with other active ingredients.

BACKGROUND OF THE INVENTION

The present invention relates to chemical compounds that inhibit MKNK1 kinase (also known as MAP Kinase interacting Kinase, Mnk1) and/or MKNK2 kinase (also known as MAP Kinase interacting Kinase, Mnk2).

Human MKNKs comprise a group of four proteins encoded by two genes (Gene symbols: MKNK1 and MKNK2) by alternative splicing. The b-forms lack a MAP kinase-binding domain situated at the C-terminus. The catalytic domains of the MKNK1 and MKNK2 are very similar and contain a unique DFD (Asp-Phe-Asp) motif in subdomain VII, which usually is DFG (Asp-Phe-Gly) in other protein kinases and suggested to alter ATP binding [Jauch et al., Structure 13, 1559-1568, 2005 and Jauch et al., EMBO J25, 4020-4032, 2006]. MKNK1a binds to and is activated by ERK and p38 MAP Kinases, but not by JNK1. MKNK2a binds to and is activated only by ERK. MKNK1b has low activity under all conditions and MKNK2b has a basal activity independent of ERK or p38 MAP Kinase. [Buxade M et al., Frontiers in Bioscience 5359-5374, May 1, 2008]

MKNKs have been shown to phosphorylate eukaryotic initiation factor 4E (eIF4E), heterogeneous nuclear RNA-binding protein A1 (hnRNP A1), polypyrimidine-tract binding protein-associated splicing factor (PSF), cytoplasmic phospholipase A2 (cPLA2) and Sprouty 2 (hSPRY2) [Buxade M et al., Frontiers in Bioscience 5359-5374, May 1, 2008].

eIF4E is an oncogene that is amplified in many cancers and is phosphorylated exclusively by MKNKs proteins as shown by KO-mouse studies [Konicek et al., Cell Cycle 7:16, 2466-2471, 2008; Ueda et al., Mol Cell Biol 24, 6539-6549, 2004]. eIF4E has a pivotal role in enabling the translation of cellular mRNAs. eIF4E binds the 7-methylguanosine cap at the 5' end of cellular mRNAs and delivers them to the ribosome as part of the eIF4F complex, also containing eIF4G and eIF4A. Though all capped mRNAs require eIF4E for translation, a pool of mRNAs is exceptionally dependent on elevated eIF4E activity for translation. These so-called "weak mRNAs" are usually Less efficiently translated due to their Long and complex 5'UTR region and they encode proteins that play significant roles in all aspects of malignancy including VEGF, FGF-2, c-Myc, cyclin D1, survivin, BCL-2, MCL-1, MMP-9, heparanase, etc. Expression and function of eIF4E is elevated in multiple human cancers and directly related to disease progression [Konicek et al., Cell Cycle 7:16, 2466-2471, 2008].

MKNK1 and MKNK2 are the only kinases known to phosphorylate eIF4E at Ser209. Overall translation rates are not affected by eIF4E phosphorylation, but it has been suggested that eIF4E phosphorylation contributes to polysome formation (i.e. multiple ribosome on a single mRNA) that ultimately enables more efficient translation of "weak mRNAs" [Buxade M et al., Frontiers in Bioscience 5359-5374, May 1, 2008]. Alternatively, phosphorylation of eIF4E by MKNK proteins might facilitate eIF4E release from the 5' cap so that the 48S complex can move along the "weak mRNA" in order to Locate the start codon [Blagden S P and Willis A E, Nat Rev Clin Oncol. 8(5):280-91, 2011]. Accordingly, increased eIF4E phosphorylation predicts poor prognosis in non-small cell lung cancer patients [Yoshizawa et al., Clin Cancer Res. 16(1):240-8, 2010]. Further data point to a functional role of MKNK1 in carcinogenesis, as overexpression of constitutively active MKNK1, but not of kinase-dead MKNK1, in mouse embryo fibroblasts accelerates tumor formation [Chrestensen C. A. et al., Genes Cells 12, 1133-1140, 2007]. Moreover, increased phosphorylation and activity of MKNK proteins correlate with overexpression of HER2 in breast cancer [Chrestensen, C. A. et al., J. Biol. Chem. 282, 4243-4252, 2007]. Constitutively active, but not kinase-dead, MKNK1 also accelerated tumor growth in a model using Eµ-Myc transgenic hematopoietic stem cells to produce tumors in mice. Comparable results were achieved, when an eIF4E carrying a S209D mutation was analyzed. The S209D mutation mimicks a phosphorylation at the MKNK1 phosphorylation site. In contrast a non-phosphorylatable form of eIF4E attenuated tumor growth [Wendel H G, et al, Genes Dev. 21(24):3232-7, 2007]. A selective MKNK inhibitor that blocks eIF4E phosphorylation induces apoptosis and suppresses proliferation and soft agar growth of cancer cells in vitro. This inhibitor also suppresses outgrowth of experimental B16 melanoma pulmonary metastases and growth of subcutaneous HCT116 colon carcinoma xenograft tumors without affecting body weight [Konicek et al, Cancer Res. 71(5): 1849-57, 2011]. Screening of a cohort of pancreatic ductal adenocarcinoma patients by immunohistochemistry showed that eIF4E phosphorylation correlated with disease grade, early onset of disease and worse prognosis. In addition it was suggested based on preclinical in vitro findings that the MNK/eIF4E pathway represents an escape route utilized by pancreatic ductal adenocarcinoma cells to withstand chemotherapeutic treatments (e.g Gemcitabine) [Adesso L, et al., Oncogene. 2012 Jul. 16]. Furthermore, it was observed that Rapamycin activated MKNK1 kinase activity in multiple myeloma cell lines and primary specimens by a MKNK-dependent mechanism. Pharmacological inhibition of MKNK activity or genetic silencing of MKNK1 prevented a rapalog-induced upregulation of c-myc IRES activity. Although Rapamycin, used alone, had little effect on myc protein expression, when combined with a MKNK inhibitor, myc protein expression was abrogated. These data provide a rationale for therapeutically targeting MKNK kinases for combined treatment with mTOR inhibitors [Shi Y et al., Oncogene. 2012 Feb. 27]. In summary, eIF4E phosphorylation through MKNK protein activity can promote cellular proliferation and survival and is critical for malignant transformation. Inhibition of MKNK activity may provide a tractable cancer therapeutic approach.

WO 2006/136402 A1 and WO 2007/059905 A2 (Develogen AG) disclose thienopyrimidin-4-amines and their use for the prophylaxis and/or treatment of diseases which can be influenced by the inhibition of the kinase activity of Mnk1 and/or Mnk2.

WO 2010/023181 A1, WO 2011/104334 A1, WO 2011/104337 A1, WO 2011/104338 A1 and WO 2011/104340 A1 (Boehringer Ingelheim) relate to thienopyrimidin-4-amines for the prophylaxis and/or treatment of diseases which can be influenced by the inhibition of the kinase activity of Mnk1 and/or Mnk2.

US 2011/0160203 A1 (ArQule) addresses substituted pyrrolo-aminopyrimidine compounds as antimitotic agents. The general formula I of claim 1 of the US application generically covers inter alia pyrrolopyrimidinylamino-benzothiazolone compounds. However, there is no specific example of a benzothiazolonyl-substituted pyrrolo-aminopyrimidine disclosed in the specification of the patent application.

WO 2005/117890 A2 discloses, inter alia pyrrolo-aminopyrimidine compounds, for the treatment of C—C chemokine mediated conditions. The compounds do not bear a benzothiazolyl group.

So, the state of the art described above does not describe the specific substituted pyrrolopyrimidinylamino-benzothiazolone compounds of general formula I of the present invention as defined herein, or a stereoisomer, a tautomer, an N-oxide, a hydrate, a solvate, or a salt thereof, or a mixture of same, as described and defined herein, and as hereinafter referred to as "compounds of the present invention", or their pharmacological activity.

It has now been found, and this constitutes the basis of the present invention, that said compounds of the present invention have surprising and advantageous properties.

In particular, said compounds of the present invention have surprisingly been found to effectively inhibit MKNK1 kinase and may therefore be used for the treatment or prophylaxis of diseases of uncontrolled cell growth, proliferation and/or survival, inappropriate cellular immune responses, or inappropriate cellular inflammatory responses or diseases which are accompanied with uncontrolled cell growth, proliferation and/or survival, inappropriate cellular immune responses, or inappropriate cellular inflammatory responses, particularly in which the uncontrolled cell growth, proliferation and/or survival, inappropriate cellular immune responses, or inappropriate cellular inflammatory responses is mediated by MKNK1 kinase, such as, for example, haematological tumours, solid tumours, and/or metastases thereof, e.g. Leukaemias and myelodysplastic syndrome, malignant Lymphomas, head and neck tumours including brain tumours and brain metastases, tumours of the thorax including non-small cell and small cell Lung tumours, gastrointestinal tumours, endocrine tumours, mammary and other gynaecological tumours, urological tumours including renal, bladder and prostate tumours, skin tumours, and sarcomas, and/or metastases thereof.

SUMMARY OF THE INVENTION

The present invention covers compounds of general formula I:

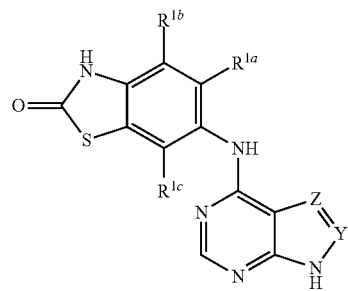

in which $R^{1a}$ represents a hydrogen atom or a halogen atom or a hydroxy-, cyano-, $C_1$-$C_6$-alkyl-, halo-$C_1$-$C_6$-alkyl-, $C_1$-$C_6$-alkoxy-, halo-$C_1$-$C_6$-alkoxy-, $C_3$-$C_6$-cycloalkyloxy-, (3- to 10-membered heterocycloalkyl)-O—, —$NR^{5a}R^{5b}$, —$SCF_3$ or —$SF_5$ group;

$R^{1b}$ represents a hydrogen atom or a halogen atom or a hydroxy-, cyano-, $C_1$-$C_6$-alkyl-, halo-$C_1$-$C_6$-alkyl-, $C_1$-$C_6$-alkoxy-, halo-$C_1$-$C_6$-alkoxy-, $C_3$-$C_6$-cycloalkyloxy-, (3- to 10-membered heterocycloalkyl)-O—, —$NR^{5a}R^{5b}$, —$SCF_3$ or —$SF_5$ group;

$R^{1c}$ represents a hydrogen atom or a halogen atom or a hydroxy-, cyano-, $C_1$-$C_6$-alkyl-, halo-$C_1$-$C_6$-alkyl-, $C_1$-$C_6$-alkoxy-, halo-$C_1$-$C_6$-alkoxy-, $C_3$-$C_6$-cycloalkyloxy-, (3- to 10-membered heterocycloalkyl)-O—, —$NR^{5a}R^{5b}$, —$SCF_3$ or —$SF_5$ group;

Y represents N or $CR^{2a}$;

Z represents N or $CR^{2b}$;

with the proviso that not more than one of Y and Z represents N;

$R^{2a}$ represents a hydrogen atom or a halogen atom or a group selected from:
  $C_1$-$C_6$-alkyl-, $C_2$-$C_6$-alkenyl-, $C_2$-$C_6$-alkynyl-, $C_3$-$C_6$-cycloalkyl-, 3- to 10-membered heterocycloalkyl-, 4- to 10-membered heterocycloalkenyl-, aryl-, heteroaryl-, halo-$C_1$-$C_3$-alkyl-, cyano-, —$(CH_2)_q$—X—$(CH_2)_p$—$R^3$;
  wherein said $C_1$-$C_6$-alkyl-, $C_2$-$C_6$-alkenyl-, $C_2$-$C_6$-alkynyl-, $C_3$-$C_6$-cycloalkyl-, 3- to 10-membered heterocycloalkyl-, 4- to 10-membered heterocycloalkenyl-, aryl- or heteroaryl- group is optionally substituted, identically or differently, with 1, 2, 3, 4 or 5 $R^4$ groups;

$R^{2b}$ represents a hydrogen atom or a halogen atom or a group selected from:
  $C_1$-$C_6$-alkyl-, $C_2$-$C_6$-alkenyl-, $C_2$-$C_6$-alkynyl-, $C_3$-$C_6$-cycloalkyl-, 3- to 10-membered heterocycloalkyl-, 4- to 10-membered heterocycloalkenyl-, aryl-, heteroaryl-, halo-$C_1$-$C_3$-alkyl-, cyano-, —$(CH_2)_q$—X—$(CH_2)_p$—$R^3$;
  wherein said $C_1$-$C_6$-alkyl-, $C_2$-$C_6$-alkenyl-, $C_2$-$C_6$-alkynyl-, $C_3$-$C_6$-cycloalkyl-, 3- to 10-membered heterocycloalkyl-, 4- to 10-membered heterocycloalkenyl-, aryl- or heteroaryl- group is optionally substituted, identically or differently, with 1, 2, 3, 4 or 5 $R^4$ groups;

X represents a single bond or a bivalent group selected from:
  —O—, —S—, —S(=O)—, —S(=O)$_2$—, —S(=O)(NR$^{3a}$)—, —(NR$^{3a}$)—S(=O)$_2$—, —S(=O)$_2$—(NR$^{3a}$), —(NR$^{3a}$)—S(=O)—, —C(=O)—, —(NR$^{3a}$)—, —C(=O)—O—, —O—C(=O)—, —C(=S)—O—, —O—C(=S)—, —C(=O)—(NR$^{3a}$)—, —(NR$^{3a}$)—C(=O)—, —(NR$^{3a}$)—C(=O)—(NR$^{3b}$)—, —O—C(=O)—(NR$^{3a}$)—, —(NR$^{3a}$)—C(=O)—O—;

$R^3$ represents a hydrogen atom or a group selected from $C_1$-$C_6$-alkyl-, $C_3$-$C_6$-cycloalkyl-, 3- to 10-membered heterocycloalkyl-, aryl-, heteroaryl-, halo-$C_1$-$C_3$-alkyl-;
  wherein said $C_1$-$C_6$-alkyl-, $C_3$-$C_6$-cycloalkyl-, 3- to 10-membered heterocycloalkyl-, aryl- or heteroaryl- group is optionally substituted, identically or differently, with 1, 2, 3, 4 or 5 $R^4$ groups;

$R^{3a}$ represents a hydrogen atom or a group selected from $C_1$-$C_6$-alkyl-, $C_3$-$C_6$-cycloalkyl-, 3- to 10-membered heterocycloalkyl-, aryl-, heteroaryl-, halo-$C_1$-$C_3$-alkyl-;
  wherein said $C_1$-$C_6$-alkyl-, $C_3$-$C_6$-cycloalkyl-, 3- to 10-membered heterocycloalkyl-, aryl- or heteroaryl- group is optionally substituted, identically or differently, with 1, 2, 3, 4 or 5 $R^4$ groups;

$R^{3b}$ represents a hydrogen atom or a group selected from $C_1$-$C_6$-alkyl-, $C_3$-$C_6$-cycloalkyl-, 3- to 10-membered heterocycloalkyl-, aryl-, heteroaryl-, halo-$C_1$-$C_3$-alkyl-;

wherein said $C_1$-$C_6$-alkyl-, $C_3$-$C_6$-cycloalkyl-, 3- to 10-membered heterocycloalkyl-, aryl- or heteroaryl- group is optionally substituted, identically or differently, with 1, 2, 3, 4 or 5 $R^4$ groups; or $R^3$ together with $R^{3a}$ or $R^{3b}$ represent a 3- to 10-membered heterocycloalkyl- or a 4- to 10-membered heterocycloalkenyl- group, which is optionally substituted, one or more times, identically or differently, with $C_1$-$C_3$-alkyl-, halo-, hydroxyl-, cyano-;

$R^4$ represents halo-, hydroxy-, oxo- (O=), cyano-, nitro-, $C_1$-$C_6$-alkyl-, $C_2$-$C_6$-alkenyl-, $C_2$-$C_6$-alkynyl-, halo-$C_1$-$C_6$-alkyl-, $C_1$-$C_6$-alkoxy-, halo-$C_1$-$C_6$-alkoxy-, hydroxy-$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-, $R^5$—O—, —C(=O)—$R^5$, —C(=O)—O—$R^5$, —O—C(=O)—$R^5$, —N($R^{5a}$)—C(=O)—$R^{5b}$, —N($R^{5a}$)—C(=O)—$NR^{5b}R^{5c}$, —$NR^{5a}R^{5b}$, —C(=O)—$NR^{5a}R^{5b}$, $R^5$—S—, $R^5$—S(=O)—, $R^5$—S(=O)$_2$—, —N($R^{5a}$)—S(=O)—$R^{5b}$, —S(=O)—$NR^{5a}R^{5b}$, —N($R^{5a}$)—S(=O)$_2$—$R^{5b}$, —S(=O)$_2$—$NR^{5a}R^{5b}$, —S(=O)(=$NR^{5a}$)$R^{5b}$, —S(=O)(=$NR^{5a}$)$R^{5b}$ or —N=S(=O)($R^{5a}$)$R^{5b}$;

$R^5$ represents a hydrogen atom, a $C_1$-$C_6$-alkyl- or $C_3$-$C_6$-cycloalkyl- group;

$R^{5a}$ represents a hydrogen atom, a $C_1$-$C_6$-alkyl- or $C_3$-$C_6$-cycloalkyl- group;

$R^{5b}$ represents a hydrogen atom, a $C_1$-$C_6$-alkyl- or $C_3$-$C_6$-cycloalkyl- group;

$R^{5c}$ represents a hydrogen atom, a $C_1$-$C_6$-alkyl- or $C_3$-$C_6$-cycloalkyl- group; or $R^{5a}$ and $R^{5b}$, $R^{5a}$ and $R^{5c}$, or $R^{5b}$ and $R^{5c}$ together may form a $C_2$-$C_6$-alkylene group, in which optionally one methylene can be replaced by —O—, —C(=O)—, —NH—, or —N($C_1$-$C_4$-alkyl)-;

p represents an integer of 0, 1, 2 or 3;

q represents an integer of 0, 1, 2 or 3;

or a tautomer, an N-oxide, a hydrate, a solvate, or a salt thereof, or a mixture of same.

The present invention further relates to methods of preparing compounds of general formula I, to pharmaceutical compositions and combinations comprising said compounds, to the use of said compounds for manufacturing a pharmaceutical composition for the treatment or prophylaxis of a disease, as well as to intermediate compounds useful in the preparation of said compounds.

DETAILED DESCRIPTION OF THE INVENTION

The terms as mentioned in the present text have preferably the following meanings:

The term "halogen atom", "halo-" or "Hal-" is to be understood as meaning a fluorine, chlorine, bromine or iodine atom, preferably a fluorine, chlorine or bromine atom.

The term "$C_1$-$C_6$-alkyl" is to be understood as preferably meaning a linear or branched, saturated, monovalent hydrocarbon group having 1, 2, 3, 4, 5 or 6 carbon atoms, e.g. a methyl, ethyl, propyl, butyl, pentyl, hexyl, iso-propyl, iso-butyl, sec-butyl, tert-butyl, iso-pentyl, 2-methylbutyl, 1-methylbutyl, 1-ethylpropyl, 1,2-dimethylpropyl, neo-pentyl, 1,1-dimethylpropyl, 4-methylpentyl, 3-methylpentyl, 2-methylpentyl, 1-methylpentyl, 2-ethylbutyl, 1-ethylbutyl, 3,3-dimethylbutyl, 2,2-dimethylbutyl, 1,1-dimethylbutyl, 2,3-dimethylbutyl, 1,3-dimethylbutyl, or 1,2-dimethylbutyl group, or an isomer thereof. Particularly, said group has 1, 2, 3 or 4 carbon atoms ("$C_1$-$C_4$-alkyl"), e.g. a methyl, ethyl, propyl, butyl, iso-propyl, iso-butyl, sec-butyl, tert-butyl group, more particularly 1, 2 or 3 carbon atoms ("$C_1$-$C_3$-alkyl"), e.g. a methyl, ethyl, n-propyl- or iso-propyl group.

The term "$C_2$-$C_6$-alkylene" is to be understood as preferably meaning a linear or branched, saturated, bivalent hydrocarbon group having 2, 3, 4, 5 or 6 carbon atoms, e.g. an ethylene, n-propylene, n-butylene, n-pentylene, 2-methylbutylene, n-hexylene, 3-methylpentylene group, or an isomer thereof. Particularly, said group is linear and has 2, 3, 4 or 5 carbon atoms ("$C_2$-$C_5$-alkylene"), e.g. an ethylene, n-propylene, n-butylene, n-pentylene group, more particularly 3 or 4 carbon atoms ("$C_3$-$C_4$-alkylene"), e.g. an n-propylene or n-butylene group.

The term "halo-$C_1$-$C_6$-alkyl" is to be understood as preferably meaning a linear or branched, saturated, monovalent hydrocarbon group in which the term "$C_1$-$C_6$-alkyl" is defined supra, and in which one or more hydrogen atoms is replaced by a halogen atom, in identically or differently, i.e. one halogen atom being independent from another. Particularly, said halogen atom is F. Said halo-$C_1$-$C_6$-alkyl group is, for example, —$CF_3$, —$CHF_2$, —$CH_2F$, —$CF_2CF_3$, or —$CH_2CF_3$.

The term "$C_1$-$C_6$-alkoxy" is to be understood as preferably meaning a linear or branched, saturated, monovalent, hydrocarbon group of formula —O—($C_1$-$C_6$-alkyl), in which the term "$C_1$-$C_6$-alkyl" is defined supra, e.g. a methoxy, ethoxy, n-propoxy, iso-propoxy, n-butoxy, iso-butoxy, tert-butoxy, sec-butoxy, pentoxy, iso-pentoxy, or n-hexoxy group, or an isomer thereof.

The term "halo-$C_1$-$C_6$-alkoxy" is to be understood as preferably meaning a linear or branched, saturated, monovalent $C_1$-$C_6$-alkoxy group, as defined supra, in which one or more of the hydrogen atoms is replaced, in identically or differently, by a halogen atom. Particularly, said halogen atom is F. Said halo-$C_1$-$C_6$-alkoxy group is, for example, —$OCF_3$, —$OCHF_2$, —$OCH_2F$, —$OCF_2CF_3$, or —$OCH_2CF_3$.

The term "$C_1$-$C_6$-alkoxy-$C_1$-$C_6$-alkyl" is to be understood as preferably meaning a linear or branched, saturated, monovalent $C_1$-$C_6$-alkyl group, as defined supra, in which one or more of the hydrogen atoms is replaced, in identically or differently, by a $C_1$-$C_6$-alkoxy group, as defined supra, e.g. methoxyalkyl, ethoxyalkyl, propyloxyalkyl, iso-propoxyalkyl, butoxyalkyl, iso-butoxyalkyl, tert-butoxyalkyl, sec-butoxyalkyl, pentyloxyalkyl, iso-pentyloxyalkyl, hexyloxyalkyl group, or an isomer thereof.

The term "halo-$C_1$-$C_6$-alkoxy-$C_1$-$C_6$-alkyl" is to be understood as preferably meaning a linear or branched, saturated, monovalent $C_1$-$C_6$-alkoxy-$C_1$-$C_6$-alkyl group, as defined supra, in which one or more of the hydrogen atoms is replaced, in identically or differently, by a halogen atom. Particularly, said halogen atom is F. Said halo-$C_1$-$C_6$-alkoxy-$C_1$-$C_6$-alkyl group is, for example, —$CH_2CH_2OCF_3$, —$CH_2CH_2OCHF_2$, —$CH_2CH_2OCH_2F$, —$CH_2CH_2OCF_2CF_3$, or —$CH_2CH_2OCH_2CF_3$.

The term "$C_2$-$C_6$-alkenyl" is to be understood as preferably meaning a linear or branched, monovalent hydrocarbon group, which contains one or more double bonds, and which has 2, 3, 4, 5 or 6 carbon atoms, particularly 2 or 3 carbon atoms ("$C_2$-$C_3$-alkenyl"), it being understood that in the case in which said alkenyl group contains more than one double bond, then said double bonds may be isolated from, or conjugated with, each other. Said alkenyl group is, for example, a vinyl, allyl, (E)-2-methylvinyl, (Z)-2-methylvinyl, homoallyl, (E)-but-2-enyl, (Z)-but-2-enyl, (E)-but-1-enyl, (Z)-but-1-enyl, pent-4-enyl, (E)-pent-3-enyl, (Z)-pent-3-enyl, (E)-pent-2-enyl, (Z)-pent-2-enyl, (E)-pent-1-enyl, (Z)-pent-1-enyl, hex-5-enyl, (E)-hex-4-enyl, (Z)-hex-4-enyl, (E)-hex-3-enyl, (Z)-hex-3-enyl, (E)-hex-2-enyl, (Z)-hex-2-enyl, (E)-hex-1-enyl, (Z)-hex-1-enyl, iso-propenyl, 2-methylprop-2-enyl, 1-methylprop-2-enyl, 2-methylprop-1-enyl, (E)-1-methylprop-1-enyl, (Z)-1-methylprop-1-enyl, 3-methylbut-3-enyl, 2-methylbut-3-enyl, 1-methylbut-3-enyl, 3-methylbut-2-enyl, (E)-2-methylbut-2-enyl, (Z)-2-methylbut-2-enyl, (E)-1-methylbut-2-enyl, (Z)-1-methylbut-2-enyl, (E)-3-methylbut-1-enyl, (Z)-3-methylbut-1-enyl, (E)-2-methylbut-1-enyl, (Z)-2-methylbut-1-enyl, (E)-1-methylbut-1-enyl, (Z)-1-methylbut-1-enyl, 1,1-dimethylprop-2-enyl, 1-ethylprop-1-enyl, 1-propylvinyl, 1-isopropylvinyl, 4-methylpent-4-enyl, 3-methylpent-4-enyl, 2-methylpent-4-enyl, 1-methylpent-4-enyl, 4-methylpent-3-enyl, (E)-3-methylpent-3-enyl, (Z)-3-methylpent-3-enyl, (E)-2-methylpent-3-enyl, (Z)-2-methylpent-3-enyl, (E)-1-methylpent-3-enyl, (Z)-1-methylpent-3-enyl, (E)-4-methylpent-2-enyl, (Z)-4-methylpent-2-enyl, (E)-3-methylpent-2-enyl, (Z)-3-methylpent-2-enyl, (E)-2-methylpent-2-enyl, (Z)-2-methylpent-2-enyl, (E)-1-methylpent-2-enyl, (Z)-1-methylpent-2-enyl, (E)-4-methylpent-1-enyl, (Z)-4-methylpent-1-enyl, (E)-3-methylpent-1-enyl, (Z)-3-methylpent-1-enyl, (E)-2-methylpent-1-enyl, (Z)-2-methylpent-1-enyl, (E)-1-methylpent-1-enyl, (Z)-1-methylpent-1-enyl, 3-ethylbut-3-enyl, 2-ethylbut-3-enyl, 1-ethylbut-3-enyl, (E)-3-ethylbut-2-enyl, (Z)-3-ethylbut-2-enyl, (E)-2-ethylbut-2-enyl, (Z)-2-ethylbut-2-enyl, (E)-1-ethylbut-2-enyl, (Z)-1-ethylbut-2-enyl, (E)-3-ethylbut-1-enyl, (Z)-3-ethylbut-1-enyl, 2-ethylbut-1-enyl, (E)-1-ethylbut-1-enyl, (Z)-1-ethylbut-1-enyl, 2-propylprop-2-enyl, i-propylprop-2-enyl, 2-isopropylprop-2-enyl, 1-isopropylprop-2-enyl, (E)-2-propylprop-1-enyl, (Z)-2-propylprop-1-enyl, (E)-1-propylprop-1-enyl, (Z)-1-propylprop-1-enyl, (E)-2-isopropylprop-1-enyl, (Z)-2-isopropylprop-1-enyl, (E)-1-isopropylprop-1-enyl, (Z)-1-isopropylprop-1-enyl, (E)-3,3-dimethylprop-1-enyl, (Z)-3,3-dimethylprop-1-enyl, 1-(1,1-dimethylethyl) ethenyl, buta-1,3-dienyl, penta-1,4-dienyl, hexa-1,5-dienyl, or methylhexadienyl group. Particularly, said group is vinyl or allyl.

The term "$C_2$-$C_6$-alkynyl" is to be understood as preferably meaning a linear or branched, monovalent hydrocarbon group which contains one or more triple bonds, and which contains 2, 3, 4, 5 or 6 carbon atoms, particularly 2 or 3 carbon atoms ("$C_2$-$C_3$-alkynyl"). Said $C_2$-$C_6$-alkynyl group is, for example, ethynyl, prop-1-ynyl, prop-2-ynyl, but-1-ynyl, but-2-ynyl, but-3-ynyl, pent-1-ynyl, pent-2-ynyl, pent-3-ynyl, pent-4-ynyl, hex-1-ynyl, hex-2-ynyl, hex-3-ynyl, hex-4-ynyl, hex-5-ynyl, 1-methylprop-2-ynyl, 2-methylbut-3-ynyl, 1-methylbut-3-ynyl, 1-methylbut-2-ynyl, 3-methylbut-1-ynyl, 1-ethylprop-2-ynyl, 3-methylpent-4-ynyl, 2-methylpent-4-ynyl, 1-methylpent-4-ynyl, 2-methylpent-3-ynyl, 1-methylpent-3-ynyl, 4-methylpent-2-ynyl, 1-methylpent-2-ynyl, 4-methylpent-1-ynyl, 3-methylpent-1-ynyl, 2-ethylbut-3-ynyl, 1-ethylbut-3-ynyl, 1-ethylbut-2-ynyl, 1-propylprop-2-ynyl, 1-isopropylprop-2-ynyl, 2,2-dimethylbut-3-ynyl, 1,1-dimethylbut-3-ynyl, 1,1-dimethylbut-2-ynyl, or 3,3-dimethylbut-1-ynyl group. Particularly, said alkynyl group is ethynyl, prop-1-ynyl, or prop-2-ynyl.

The term "$C_3$-$C_{10}$-cycloalkyl" is to be understood as meaning a saturated, monovalent, mono-, or bicyclic hydrocarbon ring which contains 3, 4, 5, 6, 7, 8, 9 or 10 carbon atoms ("$C_3$-$C_{10}$-cycloalkyl"). Said $C_3$-$C_{10}$-cycloalkyl group is for example, a monocyclic hydrocarbon ring, e.g. a cyclopropyl, cyclobutyl, cyclopentyl, cyclohexyl, cycloheptyl, cyclooctyl, cyclononyl or cyclodecyl, or a bicyclic hydrocarbon ring, e.g. a perhydropentalenylene or decalin ring. Particularly, said ring contains 3, 4, 5 or 6 carbon atoms ("$C_3$-$C_6$-cycloalkyl").

The term "$C_3$-$C_6$-cycloalkyloxy" refers to a ($C_3$-$C_6$-cycloalkyl)-O— group in which "$C_3$-$C_6$-cycloalkyl" is as defined herein. Examples include, but are not limited to, cyclopropanoxy and cyclobutanoxy.

The term "$C_4$-$C_{10}$-cycloalkenyl" is to be understood as preferably meaning a non-aromatic, monovalent, mono-, or bicyclic hydrocarbon ring which contains 4, 5, 6, 7, 8, 9 or 10 carbon atoms and one, two, three or four double bonds, in conjugation or not, as the size of said cycloalkenyl ring allows. Said $C_4$-$C_{10}$-cycloalkenyl group is for example, a monocyclic hydrocarbon ring, e.g. a cyclobutenyl, cyclopentenyl, or cyclohexenyl or a bicyclic hydrocarbon, e.g.:

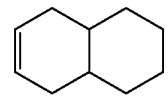

The term "3- to 10-membered heterocycloalkyl", is to be understood as meaning a saturated, monovalent, mono- or bicyclic hydrocarbon ring which contains 2, 3, 4, 5, 6, 7, 8 or 9 carbon atoms, and one or more heteroatom-containing groups selected from C(=O), O, S, S(=O), S(=O)$_2$, NR$^a$, in which R$^a$ represents a hydrogen atom or a $C_1$-$C_6$-alkyl-group; it being possible for said heterocycloalkyl group to be attached to the rest of the molecule via any one of the carbon atoms or, if present, the nitrogen atom.

Particularly, said 3- to 10-membered heterocycloalkyl can contain 2, 3, 4, or 5 carbon atoms, and one or more of the above-mentioned heteroatom-containing groups (a "3- to 6-membered heterocycloalkyl"), more particularly said heterocycloalkyl can contain 4 or 5 carbon atoms, and one or more of the above-mentioned heteroatom-containing groups (a "5- to 6-membered heterocycloalkyl").

Particularly, without being limited thereto, said heterocycloalkyl can be a 4-membered ring, such as an azetidinyl, oxetanyl, or a 5-membered ring, such as tetrahydrofuranyl, dioxolinyl, pyrrolidinyl, imidazolidinyl, pyrazolidinyl, or a 6-membered ring, such as tetrahydropyranyl, piperidinyl, morpholinyl, dithianyl, thiomorpholinyl, piperazinyl, or trithianyl, or a 7-membered ring, such as a diazepanyl ring, for example.

Said heterocycloalkyl can be bicyclic, such as, without being limited thereto, a 5,5-membered ring, e.g. a hexahydrocyclopenta[c]pyrrol-2(1H)-yl ring, or a 5,6-membered bicyclic ring, e.g. a hexahydropyrrolo[1,2-a]pyrazin-2(1H)-yl ring.

The term "4- to 10-membered heterocycloalkenyl", is to be understood as meaning an non-aromatic, unsaturated, monovalent, mono- or bicyclic hydrocarbon ring which contains 3, 4, 5, 6, 7, 8 or 9 carbon atoms, and one or more heteroatom-containing groups selected from C(=O), O, S, S(=O), S(=O)$_2$, NR$^a$, in which R$^a$ represents a hydrogen atom or a $C_1$-$C_6$-alkyl- group; it being possible for said heterocycloalkenyl group to be attached to the rest of the molecule via any one of the carbon atoms or, if present, the nitrogen atom. Examples of said heterocycloalkenyl are e.g. 4H-pyranyl, 2H-pyranyl, 3H-diazirinyl, 2,5-dihydro-1H-pyrrolyl, [1,3]dioxolyl, 4H-[1,3,4]thiadiazinyl, 2,5-dihydrofuranyl, 2,3-dihydrofuranyl, 2,5-dihydrothiophenyl, 2,3-dihydrothiophenyl, 4,5-dihydrooxazolyl, or 4H-[1,4]thiazinyl group.

The term "aryl" is to be understood as preferably meaning a monovalent, aromatic or partially aromatic, mono-, or bi- or tricyclic hydrocarbon ring having 6, 7, 8, 9, 10, 11, 12, 13 or 14 carbon atoms (a "$C_6$-$C_{14}$-aryl" group), particularly a ring having 6 carbon atoms (a "$C_6$-aryl" group), e.g. a phenyl group; or a biphenyl group, or a ring having 9 carbon atoms (a "$C_9$-aryl" group), e.g. an indanyl or indenyl group, or a ring having 10 carbon atoms (a "$C_{10}$-aryl" group), e.g. a tetralinyl, dihydronaphthyl, or naphthyl group, or a ring having 13 carbon atoms, (a "$C_{13}$-aryl" group), e.g. a fluorenyl group, or a ring having 14 carbon atoms, (a "$C_{14}$-aryl" group), e.g. an anthranyl group. Preferably, the aryl group is a phenyl group.

The term "heteroaryl" is understood as preferably meaning a monovalent, monocyclic, bicyclic or tricyclic aromatic ring system having 5, 6, 7, 8, 9, 10, 11, 12, 13 or 14 ring atoms (a "5- to 14-membered heteroaryl" group), particularly 5 or 6 or 9 or 10 atoms, and which contains at least one heteroatom which may be identical or different, said heteroatom being such as oxygen, nitrogen or sulfur, and in addition in each case can be benzocondensed. Particularly, heteroaryl is selected from thienyl, furanyl, pyrrolyl, oxazolyl, thiazolyl, imidazolyl, pyrazolyl, isoxazolyl, isothiazolyl, oxadiazolyl, triazolyl, thiadiazolyl, thia-4H-pyrazolyl etc., and benzo derivatives thereof, such as, for example, benzofuranyl, benzothienyl, benzoxazolyl, benzisoxazolyl, benzimidazolyl, benzotriazolyl, indazolyl, indolyl, isoindolyl, etc.; or pyridyl, pyridazinyl, pyrimidinyl, pyrazinyl, triazinyl, etc., and benzo derivatives thereof, such as, for example, quinolinyl, quinazolinyl, isoquinolinyl, etc.; or azocinyl, indolizinyl, purinyl, etc., and benzo derivatives thereof; or cinnolinyl, phthalazinyl, quinazolinyl, quinoxalinyl, naphthpyridinyl, pteridinyl, carbazolyl, acridinyl, phenazinyl, phenothiazinyl, phenoxazinyl, xanthenyl, or oxepinyl, etc.

In general, and unless otherwise mentioned, the heteroarylic or heteroarylenic radicals include all the possible isomeric forms thereof, e.g. the positional isomers thereof. Thus, for some illustrative non-restricting example, the term pyridinyl or pyridinylene includes pyridin-2-yl, pyridin-2-ylene, pyridin-3-yl, pyridin-3-ylene, pyridin-4-yl and pyridin-4-ylene; or the term thienyl or thienylene includes thien-2-yl, thien-2-ylene, thien-3-yl and thien-3-ylene.

The term "$C_1$-$C_6$", as used throughout this text, e.g. in the context of the definition of "$C_1$-$C_6$-alkyl", "$C_1$-$C_6$-haloalkyl", "$C_1$-$C_6$-alkoxy", or "$C_1$-$C_6$-haloalkoxy" is to be understood as meaning an alkyl group having a finite number of carbon atoms of 1 to 6, i.e. 1, 2, 3, 4, 5, or 6 carbon atoms. It is to be understood further that said term "$C_1$-$C_6$" is to be interpreted as any sub-range comprised therein, e.g. $C_1$-$C_6$, $C_2$-$C_5$, $C_3$-$C_4$, $C_1$-$C_2$, $C_1$-$C_3$, $C_1$-$C_4$, $C_1$-$C_5$; particularly $C_1$-$C_2$, $C_1$-$C_3$, $C_1$-$C_4$, $C_1$-$C_5$, $C_1$-$C_6$; more particularly $C_1$-$C_4$; in the case of "$C_1$-$C_6$-haloalkyl" or "$C_1$-$C_6$-haloalkoxy" even more particularly $C_1$-$C_2$.

Similarly, as used herein, the term "$C_2$-$C_6$", as used throughout this text, e.g. in the context of the definitions of "$C_2$-$C_6$-alkenyl" and "$C_2$-$C_6$-alkynyl", is to be understood as meaning an alkenyl group or an alkynyl group having a finite number of carbon atoms of 2 to 6, i.e. 2, 3, 4, 5, or 6 carbon atoms. It is to be understood further that said term "$C_2$-$C_6$" is to be interpreted as any sub-range comprised therein, e.g. $C_2$-$C_6$, $C_3$-$C_5$, $C_3$-$C_4$, $C_2$-$C_3$, $C_2$-$C_4$, $C_2$-$C_5$; particularly $C_2$-$C_3$.

Further, as used herein, the term "$C_3$-$C_6$", as used throughout this text, e.g. in the context of the definition of "$C_3$-$C_6$-cycloalkyl", is to be understood as meaning a cycloalkyl group having a finite number of carbon atoms of 3 to 6, i.e. 3, 4, 5 or 6 carbon atoms. It is to be understood further that said term "$C_3$-$C_6$" is to be interpreted as any sub-range comprised therein, e.g. $C_3$-$C_6$, $C_4$-$C_5$, $C_3$-$C_5$, $C_3$-$C_4$, $C_4$-$C_6$, $C_5$-$C_6$; particularly $C_3$-$C_6$.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds.

The term "optionally substituted" means optional substitution with the specified groups, radicals or moieties.

As used herein, the term "leaving group" refers to an atom or a group of atoms that is displaced in a chemical reaction as stable species taking with it the bonding electrons. Preferably, a leaving group is selected from the group comprising: halo, in particular chloro, bromo or iodo, methanesulfonyloxy, p-toluenesulfonyloxy, trifluoromethanesulfonyloxy, nonafluorobutanesulfonyloxy, (4-bromo-benzene)sulfonyloxy, (4-nitro-benzene)sulfonyloxy, (2-nitro-benzene)-sulfonyloxy, (4-isopropyl-benzene)sulfonyloxy, (2,4,6-tri-isopropyl-benzene)-sulfonyloxy, (2,4,6-trimethyl-benzene)sulfonyloxy, (4-tertbutyl-benzene)sulfonyloxy, benzenesulfonyloxy, and (4-methoxy-benzene)sulfonyloxy.

As used herein, the term "protective group" is a protective group attached to a nitrogen in intermediates used for the preparation of compounds of the general formula I. Such groups are introduced e.g. by chemical modification of the respective amino group in order to obtain chemoselectivity in a subsequent chemical reaction. Protective groups for amino groups are described for example in T. W. Greene and P. G. M. Wuts in *Protective Groups in Organic Synthesis*, 3$^{rd}$ edition, Wiley 1999; more specifically, said groups can be selected from substituted sulfonyl groups, such as mesyl-, tosyl- or phenylsulfonyl-, acyl groups such as benzoyl, acetyl or tetrahydropyranoyl-, or carbamate based groups, such as tert.-butoxycarbonyl (Boc), or can include silicon, as in e.g. 2-(trimethylsilyl)ethoxymethyl (SEM).

As used herein, the term "one or more", e.g. in the definition of the substituents of the compounds of the general formulae of the present invention, is understood as meaning "one, two, three, four or five, particularly one, two, three or four, more particularly one, two or three, even more particularly one or two".

The invention also includes all suitable isotopic variations of a compound of the invention. An isotopic variation of a compound of the invention is defined as one in which at least one atom is replaced by an atom having the same atomic number but an atomic mass different from the atomic mass usually or predominantly found in nature. Examples of isotopes that can be incorporated into a compound of the invention include isotopes of hydrogen, carbon, nitrogen, oxygen, phosphorus, sulphur, fluorine, chlorine, bromine and iodine, such as $^2$H (deuterium), $^3$H (tritium), $^{11}$C, $^{13}$C, $^{14}$C, $^{15}$N, $^{17}$O, $^{18}$O, $^{32}$P, $^{33}$P, $^{33}$S, $^{34}$S, $^{35}$S, $^{36}$S, $^{18}$F, $^{36}$Cl, $^{82}$Br, $^{123}$I, $^{124}$I, $^{129}$I and $^{131}$I, respectively. Certain isotopic variations of a compound of the invention, for example, those in which one or more radioactive isotopes such as $^3$H or $^{14}$C are incorporated, are useful in drug and/or substrate tissue distribution studies. Tritiated and carbon-14, i.e., $^{14}$C, isotopes are particularly preferred for their ease of preparation and detectability. Further, substitution with isotopes such as deuterium may afford certain therapeutic advantages resulting from greater metabolic stability, for example, increased in vivo half-life or reduced dosage requirements and hence may be preferred in some circumstances. Isotopic variations of a compound of the invention can generally be prepared by conventional procedures known by a person skilled in the art such as by the illustrative methods or by the preparations described in the examples hereafter using appropriate isotopic variations of suitable reagents.

Where the plural form of the word compounds, salts, polymorphs, hydrates, solvates and the like, is used herein, this is taken to mean also a single compound, salt, polymorph, isomer, hydrate, solvate or the like.

By "stable compound' or "stable structure" is meant a compound that is sufficiently robust to survive isolation to a useful degree of purity from a reaction mixture, and formulation into an efficacious therapeutic agent.

The compounds of this invention may contain one or more asymmetric centre, depending upon the location and nature of the various substituents desired. Asymmetric carbon atoms may be present in the (R) or (S) configuration, resulting in racemic mixtures in the case of a single asymmetric centre, and diastereomeric mixtures in the case of multiple asymmetric centres. In certain instances, asymmetry may also be present due to restricted rotation about a given bond, for example, the central bond adjoining two substituted aromatic rings of the specified compounds.

The compounds of the present invention may contain sulphur atoms which are asymmetric, such as an asymmetric sulphoxide or sulphoximine group, of structure:

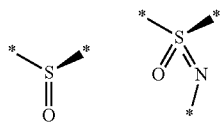

for example, in which * indicates atoms to which the rest of the molecule can be bound.

Substituents on a ring may also be present in either cis or trans form. It is intended that all such configurations (including enantiomers and diastereomers), are included within the scope of the present invention.

Preferred compounds are those which produce the more desirable biological activity. Separated, pure or partially purified isomers and stereoisomers or racemic or diastereomeric mixtures of the compounds of this invention are also included within the scope of the present invention. The purification and the separation of such materials can be accomplished by standard techniques known in the art.

Pure stereoisomers can be obtained by resolution of racemic mixtures according to conventional processes, for example, by the formation of diastereoisomeric salts using an optically active acid or base or formation of covalent diastereomers. Examples of appropriate acids are tartaric, diacetyltartaric, ditoluoyltartaric and camphorsulfonic acid. Mixtures of diastereoisomers can be separated into their individual diastereomers on the basis of their physical and/or chemical differences by methods known in the art, for example, by chromatography or fractional crystallisation. The optically active bases or acids are then liberated from the separated diastereomeric salts. A different process for separation of optical isomers involves the use of chiral chromatography (e.g., chiral HPLC columns), with or without conventional derivatisation, optimally chosen to maximise the separation of the enantiomers. Suitable chiral HPLC columns are manufactured by Daicel, e.g., Chiracel OD and Chiracel OJ among many others, all routinely selectable. Enzymatic separations, with or without derivatisation, are also useful. The optically active compounds of this invention can likewise be obtained by chiral syntheses utilizing optically active starting materials.

In order to limit different types of isomers from each other reference is made to IUPAC Rules Section E (Pure Appl Chem 45, 11-30, 1976).

The present invention includes all possible stereoisomers of the compounds of the present invention as single stereoisomers, or as any mixture of said stereoisomers, e.g. R- or S-isomers, or E- or Z-isomers, in any ratio. Isolation of a single stereoisomer, e.g. a single enantiomer or a single diastereomer, of a compound of the present invention may be achieved by any suitable state of the art method, such as chromatography, especially chiral chromatography, for example.

Further, the compounds of the present invention may exist as tautomers. For example, any compound of the present invention which contains a pyrazole moiety as a heteroaryl group for example can exist as a 1H tautomer, or a 2H tautomer, or even a mixture in any amount of the two tautomers, or a triazole moiety for example can exist as a 1H tautomer, a 2H tautomer, or a 4H tautomer, or even a mixture in any amount of said 1H, 2H and 4H tautomers, namely:

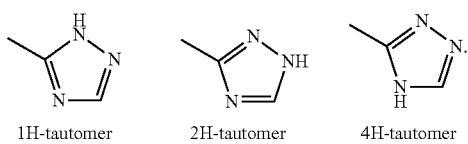

1H-tautomer    2H-tautomer    4H-tautomer

The present invention includes all possible tautomers of the compounds of the present invention as single tautomers, or as any mixture of said tautomers, in any ratio.

Further, the compounds of the present invention can exist as N-oxides, which are defined in that at least one nitrogen of the compounds of the present invention is oxidised. The present invention includes all such possible N-oxides.

The present invention also relates to useful forms of the compounds as disclosed herein, such as metabolites, hydrates, solvates, prodrugs, salts, in particular pharmaceutically acceptable salts, and co-precipitates.

The compounds of the present invention can exist as a hydrate, or as a solvate, wherein the compounds of the present invention contain polar solvents, in particular water, methanol or ethanol for example as structural element of the crystal lattice of the compounds. The amount of polar solvents, in particular water, may exist in a stoichiometric or non-stoichiometric ratio. In the case of stoichiometric solvates, e.g. a hydrate, hemi-, (semi-), mono-, sesqui-, di-, tri-, tetra-, penta- etc. solvates or hydrates, respectively, are possible. The present invention includes all such hydrates or solvates.

Further, the compounds of the present invention can exist in free form, e.g. as a free base, or as a free acid, or as a zwitterion, or can exist in the form of a salt. Said salt may be any salt, either an organic or inorganic addition salt, particularly any pharmaceutically acceptable organic or inorganic addition salt, customarily used in pharmacy.

The term "pharmaceutically acceptable salt" refers to a relatively non-toxic, inorganic or organic acid addition salt of a compound of the present invention. For example, see S. M. Berge, et al. "Pharmaceutical Salts," J. Pharm. Sci. 1977, 66, 1-19.

A suitable pharmaceutically acceptable salt of the compounds of the present invention may be, for example, an acid-addition salt of a compound of the present invention bearing a nitrogen atom, in a chain or in a ring, for example, which is sufficiently basic, such as an acid-addition salt with an inorganic acid, such as hydrochloric, hydrobromic, hydroiodic, sulfuric, bisulfuric, phosphoric, or nitric acid, for example, or with an organic acid, such as formic, acetic, acetoacetic, pyruvic, trifluoroacetic, propionic, butyric, hexanoic, heptanoic, undecanoic, lauric, benzoic, salicylic, 2-(4-hydroxybenzoyl)-benzoic, camphoric, cinnamic, cyclopentanepropionic, digluconic, 3-hydroxy-2-naphthoic, nicotinic, pamoic, pectinic, persulfuric, 3-phenylpropionic, picric, pivalic, 2-hydroxyethanesulfonate, itaconic, sulfamic, trifluoromethanesulfonic, dodecylsulfuric, ethansulfonic, benzenesulfonic, para-toluenesulfonic, methansulfonic, 2-naphthalenesulfonic, naphthalinedisulfonic, camphorsulfonic acid, citric, tartaric, stearic, Lactic, oxalic, malonic, succinic, malic, adipic, alginic, maleic, fumaric, D-gluconic, mandelic, ascorbic, glucoheptanoic, glycerophosphoric, aspartic, sulfosalicylic, hemisulfuric, or thiocyanic acid, for example.

Further, another suitably pharmaceutically acceptable salt of a compound of the present invention which is sufficiently acidic, is an alkali metal salt, for example a sodium or potassium salt, an alkaline earth metal salt, for example a calcium or magnesium salt, an ammonium salt or a salt with an organic base which affords a physiologically acceptable cation, for example a salt with N-methyl-glucamine, dimethyl-glucamine, ethyl-glucamine, lysine, dicyclohexylamine, 1,6-hexadiamine, ethanolamine, glucosamine, sarcosine, serinol, trishydroxy-methyl-aminomethane, aminopropandiol, sovakbase, 1-amino-2,3,4-butantriol, or with a quarternary ammonium salt, such as tetramethylammonium, tetraethylammonium, tetra(n-propyl)ammonium, tetra (n-butyl)ammonium, or N-benzyl-N,N,N-trimethylammonium.

Those skilled in the art will further recognise that acid addition salts of the claimed compounds may be prepared by reaction of the compounds with the appropriate inorganic or organic acid via any of a number of known methods. Alternatively, alkali and alkaline earth metal salts of acidic compounds of the invention are prepared by reacting the compounds of the invention with the appropriate base via a variety of known methods.

The present invention includes all possible salts of the compounds of the present invention as single salts, or as any mixture of said salts, in any ratio.

As used herein, the term "in vivo hydrolysable ester" is understood as meaning an in vivo hydrolysable ester of a compound of the present invention containing a carboxy or hydroxy group, for example, a pharmaceutically acceptable ester which is hydrolysed in the human or animal body to produce the parent acid or alcohol. Suitable pharmaceutically acceptable esters for carboxy include for example alkyl, cycloalkyl and optionally substituted phenylalkyl, in particular benzyl esters, $C_1$-$C_6$ alkoxymethyl esters, e.g. methoxymethyl, $C_1$-$C_6$ alkanoyloxymethyl esters, e.g. pivaloyloxymethyl, phthalidyl esters, $C_3$-$C_8$ cycloalkoxy-carbonyloxy-$C_1$-$C_6$ alkyl esters, e.g. 1-cyclohexylcarbonyloxyethyl; 1,3-dioxolen-2-onylmethyl esters, e.g. 5-methyl-1,3-dioxolen-2-onylmethyl; and $C_1$-$C_6$-alkoxycarbonyloxyethyl esters, e.g. 1-methoxycarbonyloxyethyl, and may be formed at any carboxy group in the compounds of this invention.

An in vivo hydrolysable ester of a compound of the present invention containing a hydroxy group includes inorganic esters such as phosphate esters and [alpha]-acyloxyalkyl ethers and related compounds which as a result of the in vivo hydrolysis of the ester breakdown to give the parent hydroxy group. Examples of [alpha]-acyloxyalkyl ethers include acetoxymethoxy and 2,2-dimethylpropionyloxymethoxy. A selection of in vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl. The present invention covers all such esters.

Furthermore, the present invention includes all possible crystalline forms, or polymorphs, of the compounds of the present invention, either as single polymorphs, or as a mixture of more than one polymorphs, in any ratio.

In accordance with a first aspect, the present invention covers compounds of general formula I:

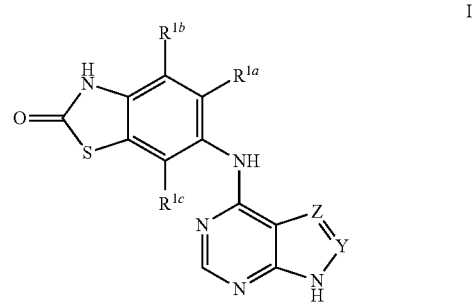

in which:
$R^{1a}$ represents a hydrogen atom or a halogen atom or a hydroxy-, cyano-, $C_1$-$C_6$-alkyl-, halo-$C_1$-$C_6$-alkyl-, $C_1$-$C_6$-alkoxy-, halo-$C_1$-$C_6$-alkoxy-, $C_3$-$C_6$-cycloalkyloxy-, (3- to 10-membered heterocycloalkyl)-O—, —NR$^{5a}$R$^{5b}$, —SCF$_3$ or —SF$_5$ group;

$R^{1b}$ represents a hydrogen atom or a halogen atom or a hydroxy-, cyano-, $C_1$-$C_6$-alkyl-, halo-$C_1$-$C_6$-alkyl-, $C_1$-$C_6$-alkoxy-, halo-$C_1$-$C_6$-alkoxy-, $C_3$-$C_6$-cycloalkyloxy-, (3- to 10-membered heterocycloalkyl)-O—, —NR$^{5a}$R$^{5b}$, —SCF$_3$ or —SF$_5$ group;

$R^{1c}$ represents a hydrogen atom or a halogen atom or a hydroxy-, cyano-, $C_1$-$C_6$-alkyl-, halo-$C_1$-$C_6$-alkyl-, $C_1$-$C_6$-alkoxy-, halo-$C_1$-$C_6$-alkoxy-, $C_3$-$C_6$-cycloalkyloxy-, (3- to 10-membered heterocycloalkyl)-O—, —NR$^{5a}$R$^{5b}$, —SCF$_3$ or —SF$_5$ group;

Y represents N or CR$^{2a}$;
Z represents N or CR$^{2b}$;
with the proviso that not more than one of Y and Z represents N;

$R^{2a}$ represents a hydrogen atom or a halogen atom or a group selected from:
  $C_1$-$C_6$-alkyl-, $C_2$-$C_6$-alkenyl-, $C_2$-$C_6$-alkynyl-, $C_3$-$C_6$-cycloalkyl-, 3- to 10-membered heterocycloalkyl-, 4- to 10-membered heterocycloalkenyl-, aryl-, heteroaryl-, halo-$C_1$-$C_3$-alkyl-, cyano-, —(CH$_2$)$_q$—X—(CH$_2$)$_p$—R$^3$;
  wherein said $C_1$-$C_6$-alkyl-, $C_2$-$C_6$-alkenyl-, $C_2$-$C_6$-alkynyl-, $C_3$-$C_6$-cycloalkyl-, 3- to 10-membered heterocycloalkyl-, 4- to 10-membered heterocycloalkenyl-, aryl- or heteroaryl- group is optionally substituted, identically or differently, with 1, 2, 3, 4 or 5 R$^4$ groups;

$R^{2b}$ represents a hydrogen atom or a halogen atom or a group selected from:
  $C_1$-$C_6$-alkyl-, $C_2$-$C_6$-alkenyl-, $C_2$-$C_6$-alkynyl-, $C_3$-$C_6$-cycloalkyl-, 3- to 10-membered heterocycloalkyl-, 4- to 10-membered heterocycloalkenyl-, aryl-, heteroaryl-, halo-$C_1$-$C_3$-alkyl-, cyano-, —(CH$_2$)$_q$—X—(CH$_2$)$_p$—R$^3$;
  wherein said $C_1$-$C_6$-alkyl-, $C_2$-$C_6$-alkenyl-, $C_2$-$C_6$-alkynyl-, $C_3$-$C_6$-cycloalkyl-, 3- to 10-membered heterocycloalkyl-, 4- to 10-membered heterocycloalkenyl-, aryl- or heteroaryl- group is optionally substituted, identically or differently, with 1, 2, 3, 4 or 5 R$^4$ groups;

X represents a single bond or a bivalent group selected from:
—O—, —S—, —S(=O)—, —S(=O)$_2$—, —S(=O)—(NR$^{3a}$)—, —(NR$^{3a}$)—S(=O)$_2$—, —S(=O)$_2$—(NR$^{3a}$)—, —(NR$^{3a}$)—S(=O)—, —C(=O)—, —(NR$^{3a}$)—, —C(=O)—O—, —O—C(=O)—, —C(=S)—O—, —O—C(=S)—, —C(=O)—(NR$^{3a}$)—, —(NR$^{3a}$)—C(=O)—, —(NR$^{3a}$)—C(=O)—(NR$^{3b}$)—, —O—C(=O)—(NR$^{3a}$)—, —(NR$^{3a}$)—C(=O)—O—;

$R^3$ represents a hydrogen atom or a group selected from $C_1$-$C_6$-alkyl-, $C_3$-$C_6$-cycloalkyl-, 3- to 10-membered heterocycloalkyl-, aryl-, heteroaryl-, halo-$C_1$-$C_3$-alkyl-;
  wherein said $C_1$-$C_6$-alkyl-, $C_3$-$C_6$-cycloalkyl-, 3- to 10-membered heterocycloalkyl-, aryl- or heteroaryl- group is optionally substituted, identically or differently, with 1, 2, 3, 4 or 5 $R^4$ groups;

$R^{3a}$ represents a hydrogen atom or a group selected from $C_1$-$C_6$-alkyl-, $C_3$-$C_6$-cycloalkyl-, 3- to 10-membered heterocycloalkyl-, aryl-, heteroaryl-, halo-$C_1$-$C_3$-alkyl-;
  wherein said $C_1$-$C_6$-alkyl-, $C_3$-$C_6$-cycloalkyl-, 3- to 10-membered heterocycloalkyl-, aryl- or heteroaryl- group is optionally substituted, identically or differently, with 1, 2, 3, 4 or 5 $R^4$ groups;

$R^{3b}$ represents a hydrogen atom or a group selected from $C_1$-$C_6$-alkyl-, $C_3$-$C_6$-cycloalkyl-, 3- to 10-membered heterocycloalkyl-, aryl-, heteroaryl-, halo-$C_1$-$C_3$-alkyl-;
  wherein said $C_1$-$C_6$-alkyl-, $C_3$-$C_6$-cycloalkyl-, 3- to 10-membered heterocycloalkyl-, aryl- or heteroaryl- group is optionally substituted, identically or differently, with 1, 2, 3, 4 or 5 $R^4$ groups; or $R^3$ together with $R^{3a}$ or $R^{3b}$ represent a 3- to 10-membered heterocycloalkyl- or a 4- to 10-membered heterocycloalkenyl- group, which is optionally substituted, one or more times, identically or differently, with $C_1$-$C_3$-alkyl-, halo-, hydroxyl-, cyano-;

$R^4$ represents halo-, hydroxy-, oxo- (O=), cyano-, nitro-, $C_1$-$C_6$-alkyl-, $C_2$-$C_6$-alkenyl-, $C_2$-$C_6$-alkynyl-, halo-$C_1$-$C_6$-alkyl-, $C_1$-$C_6$-alkoxy-, halo-$C_1$-$C_6$-alkoxy-, hydroxy-$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-, $R^5$—O—, —C(=O)—$R^5$, —C(=O)—O—$R^5$, —O—C(=O)—$R^5$, —N($R^{5a}$)—C(=O)—$R^{5b}$, —N($R^{5a}$)—C(=O)—N$R^{5b}R^{5c}$, —N$R^{5a}R^{5b}$, —C(=O)—N$R^{5a}R^{5b}$, $R^5$—S—, $R^5$—S(=O)—, $R^5$—S(=O)$_2$—, —N($R^{5a}$)—S(=O)—$R^{5b}$, —S(=O)—N$R^{5a}R^{5b}$, —N($R^{5a}$)—S(=O)$_2$—$R^{5b}$, —S(=O)$_2$—N$R^{5a}R^{5b}$, —S(=O)(=N$R^{5a}$)$R^{5b}$, —S(=O)(=N$R^{5a}$)$R^{5b}$ or —N=S(=O)($R^{5a}$)$R^{5b}$;

$R^5$ represents a hydrogen atom, a $C_1$-$C_6$-alkyl- or $C_3$-$C_6$-cycloalkyl- group;

$R^{5a}$ represents a hydrogen atom, a $C_1$-$C_6$-alkyl- or $C_3$-$C_6$-cycloalkyl- group;

$R^{5b}$ represents a hydrogen atom, a $C_1$-$C_6$-alkyl- or $C_3$-$C_6$-cycloalkyl- group;

$R^{5c}$ represents a hydrogen atom, a $C_1$-$C_6$-alkyl- or $C_3$-$C_6$-cycloalkyl- group; or $R^{5a}$ and $R^{5b}$, $R^{5a}$ and $R^{5c}$, or $R^{5b}$ and $R^{5c}$
together may form a $C_2$-$C_6$-alkylene group, in which optionally one methylene can be replaced by —O—, —C(=O)—, —NH—, or —N($C_1$-$C_4$-alkyl)-;

p represents an integer of 0, 1, 2 or 3;

q represents an integer of 0, 1, 2 or 3;

or a tautomer, an N-oxide, a hydrate, a solvate, or a salt thereof, or a mixture of same.

In a preferred embodiment, the invention relates to compounds of formula I, supra, wherein $R^{1a}$ represents a hydrogen atom or a halogen atom or a hydroxy-, cyano-, —N$R^{5a}R^{5b}$, $C_1$-$C_6$-alkyl-, halo-$C_1$-$C_6$-alkyl-, $C_1$-$C_6$-alkoxy-, or a halo-$C_1$-$C_6$-alkoxy- group.

In another preferred embodiment, the invention relates to compounds of formula I, supra, wherein $R^{1a}$ represents a hydrogen atom or a halogen atom or a hydroxy-, cyano-, —N$R^{5a}R^{5b}$, $C_1$-$C_3$-alkyl-, halo-$C_1$-$C_3$-alkyl-, $C_1$-$C_3$-alkoxy-, or a halo-$C_1$-$C_3$-alkoxy- group.

In another preferred embodiment, the invention relates to compounds of formula I, supra, wherein $R^{1a}$ represents a hydrogen atom or a halogen atom or a —N$R^{5a}R^{5b}$, $C_1$-$C_3$-alkyl-, halo-$C_1$-$C_3$-alkyl-, $C_1$-$C_3$-alkoxy-, or a halo-$C_1$-$C_3$-alkoxy- group.

In another preferred embodiment, the invention relates to compounds of formula I, supra, wherein $R^{1a}$ represents a hydrogen atom or a halogen atom or a $C_1$-$C_3$-alkyl-, halo-$C_1$-$C_3$-alkyl- group.

In another preferred embodiment, the invention relates to compounds of formula I, supra, wherein $R^{1a}$ represents a hydrogen atom or a halogen atom, or a cyano- or $C_1$-$C_3$-alkoxy- group.

In another preferred embodiment, the invention relates to compounds of formula I, supra, wherein $R^{1a}$ represents a hydrogen or halogen atom.

In another preferred embodiment, the invention relates to compounds of formula I, supra, wherein $R^{1a}$ represents a hydrogen atom or a $C_1$-$C_3$-alkoxy- group.

In another preferred embodiment, the invention relates to compounds of formula I, supra, wherein $R^{1a}$ represents a hydrogen atom or a $C_1$-$C_3$-alkyl- group.

In another preferred embodiment, the invention relates to compounds of formula I, supra, wherein $R^{1a}$ represents a hydrogen atom.

In another preferred embodiment, the invention relates to compounds of formula I, supra, wherein $R^{1a}$ represents a halogen atom.

In another preferred embodiment, the invention relates to compounds of formula I, supra, wherein $R^{1a}$ represents a $C_1$-$C_3$-alkoxy- group.

In another preferred embodiment, the invention relates to compounds of formula I, supra, wherein $R^{1a}$ represents a methoxy- group.

In another preferred embodiment, the invention relates to compounds of formula I, supra, wherein $R^{1b}$ represents a hydrogen or halogen atom or a cyano-, $C_1$-$C_6$-alkyl-, halo-$C_1$-$C_6$-alkyl-, $C_1$-$C_6$-alkoxy-, halo-$C_1$-$C_6$-alkoxy- group.

In another preferred embodiment, the invention relates to compounds of formula I, supra, wherein $R^{1b}$ represents a hydrogen or halogen atom or a cyano-, $C_1$-$C_3$-alkyl-, halo-$C_1$-$C_3$-alkyl-, $C_1$-$C_3$-alkoxy-, halo-$C_1$-$C_3$-alkoxy- group.

In another preferred embodiment, the invention relates to compounds of formula I, supra, wherein $R^{1b}$ represents a hydrogen or halogen atom or a cyano- or $C_1$-$C_3$-alkyl- group.

In another preferred embodiment, the invention relates to compounds of formula I, supra, wherein $R^{1b}$ represents a hydrogen or halogen atom.

In another preferred embodiment, the invention relates to compounds of formula I, supra, wherein $R^{1b}$ represents a hydrogen atom.

In another preferred embodiment, the invention relates to compounds of formula I, supra, wherein $R^{1b}$ represents a halogen atom.

In another preferred embodiment, the invention relates to compounds of formula I, supra, wherein $R^{1c}$ represents a hydrogen or a halogen atom or a cyano-, $C_1$-$C_6$-alkyl-, halo-$C_1$-$C_6$-alkyl-, $C_1$-$C_6$-alkoxy- or halo-$C_1$-$C_6$-alkoxy- group.

In another preferred embodiment, the invention relates to compounds of formula I, supra, wherein $R^{1c}$ represents a hydrogen or a halogen atom or a cyano-, $C_1$-$C_3$-alkyl-, halo-$C_1$-$C_3$-alkyl-, $C_1$-$C_3$-alkoxy- or halo-$C_1$-$C_3$-alkoxy- group.

In another preferred embodiment, the invention relates to compounds of formula I, supra, wherein $R^{1c}$ represents a hydrogen or a halogen atom or a cyano- or $C_1$-$C_3$-alkyl- group.

In another preferred embodiment, the invention relates to compounds of formula I, supra, wherein $R^{1c}$ represents a hydrogen or halogen atom.

In another preferred embodiment, the invention relates to compounds of formula I, supra, wherein $R^{1c}$ represents a hydrogen atom.

In another preferred embodiment, the invention relates to compounds of formula I, supra, wherein $R^{1c}$ represents a halogen atom.

In another preferred embodiment, the invention relates to compounds of formula I, supra, wherein each of $R^{1a}$, $R^{1b}$, and $R^{1c}$ represents a hydrogen atom.

In another preferred embodiment, the invention relates to compounds of formula I, supra, wherein each of $R^{1b}$ and $R^{1c}$ represents a hydrogen atom and $R^{1a}$ represents a $C_1$-$C_3$-alkoxy group, preferably a methoxy- group.

In another preferred embodiment, the invention relates to compounds of formula I, supra, wherein Y represents N and Z represents $CR^{2b}$.

In another preferred embodiment, the invention relates to compounds of formula I, supra, wherein Y represents $CR^{2a}$.

In another preferred embodiment, the invention relates to compounds of formula I, supra, wherein Z represents N and Y represents $CR^{2a}$.

In another preferred embodiment, the invention relates to compounds of formula I, supra, wherein Z represents $CR^{2b}$.

In another preferred embodiment, the invention relates to compounds of formula I, supra, wherein Z represents $CR^{2b}$ and Y represents $CR^{2a}$.

In another preferred embodiment, the invention relates to compounds of formula I, supra, wherein $R^{2a}$ represents a hydrogen atom or a halogen atom or a group selected from: $C_1$-$C_6$-alkyl-, $C_2$-$C_6$-alkenyl-, $C_2$-$C_6$-alkynyl-, $C_3$-$C_6$-cycloalkyl-, aryl-, heteroaryl-, halo-$C_1$-$C_3$-alkyl-, cyano-, 3- to 10-membered heterocycloalkyl-, 4- to 10-membered heterocycloalkenyl-, —(CH$_2$)$_q$—X—(CH$_2$)$_p$—R$^3$;
wherein said $C_1$-$C_6$-alkyl-, $C_2$-$C_6$-alkenyl-, $C_2$-$C_6$-alkynyl-, $C_3$-$C_6$-cycloalkyl-, 3- to 10-membered heterocycloalkyl-, 4- to 10-membered heterocycloalkenyl-, aryl- or heteroaryl- group is optionally substituted, identically or differently, with 1, 2 or 3 $R^4$ groups.

In another preferred embodiment, the invention relates to compounds of formula I, supra, wherein $R^{2a}$ represents a hydrogen atom or a halogen atom or a group selected from: $C_1$-$C_6$-alkyl-, $C_2$-$C_6$-alkenyl-, $C_2$-$C_6$-alkynyl-, $C_3$-$C_6$-cycloalkyl-, halo-$C_1$-$C_3$-alkyl-, cyano-, 3- to 10-membered heterocycloalkyl-, 4- to 10-membered heterocycloalkenyl-, —(CH$_2$)$_q$—X—(CH$_2$)$_p$—R$^3$; wherein said $C_1$-$C_6$-alkyl-, $C_2$-$C_6$-alkenyl-, $C_2$-$C_6$-alkynyl-, $C_3$-$C_6$-cycloalkyl-, 3- to 10-membered heterocycloalkyl- or 4- to 10-membered heterocycloalkenyl- group is optionally substituted, identically or differently, with 1, 2 or 3 $R^4$ groups.

In another preferred embodiment, the invention relates to compounds of formula I, supra, wherein $R^{2a}$ represents a hydrogen atom or a halogen atom or a group selected from: $C_1$-$C_3$-alkyl-, $C_2$-$C_4$-alkenyl-, $C_2$-$C_4$-alkynyl-, $C_3$-$C_6$-cycloalkyl-, halo-$C_1$-$C_3$-alkyl-, cyano-, 4- to 6-membered heterocycloalkyl-, 4- to 6-membered heterocycloalkenyl-, —(CH$_2$)$_q$—X—(CH$_2$)$_p$—R$^3$; wherein said $C_1$-$C_3$-alkyl-, $C_2$-$C_4$-alkenyl-, $C_2$-$C_4$-alkynyl-, $C_3$-$C_6$-cycloalkyl-, 4- to 6-membered heterocycloalkyl- or 4- to 6-membered heterocycloalkenyl- group is optionally substituted, identically or differently, with 1, 2 or 3 $R^4$ groups.

In another preferred embodiment, the invention relates to compounds of formula I, supra, wherein $R^{2a}$ represents a hydrogen atom or a halogen atom or a group selected from: $C_1$-$C_3$-alkyl-, halo-$C_1$-$C_3$-alkyl-, —(CH$_2$)$_q$—X—(CH$_2$)$_p$—R$^3$; wherein said $C_1$-$C_3$-alkyl- group is optionally substituted, identically or differently, with 1, 2 or 3 $R^4$ groups.

In another preferred embodiment, the invention relates to compounds of formula I, supra, wherein $R^{2a}$ represents a hydrogen atom or a halogen atom or a group selected from: $C_1$-$C_3$-alkyl-, —(CH$_2$)$_q$—X—(CH$_2$)$_p$—R$^3$; wherein said $C_1$-$C_3$-alkyl- group is optionally substituted, identically or differently, with 1, 2 or 3 $R^4$ groups.

In another preferred embodiment, the invention relates to compounds of formula I, supra, wherein $R^{2a}$ represents a hydrogen atom or a halogen atom or a group selected from: $C_1$-$C_3$-alkyl-, —(CH$_2$)$_q$—X—(CH$_2$)$_p$—R$^3$; wherein said $C_1$-$C_3$-alkyl- group is optionally substituted, identically or differently, with 1 or 2 $R^4$ groups.

In another preferred embodiment, the invention relates to compounds of formula I, supra, wherein $R^{2a}$ represents a hydrogen atom or a halogen atom or a group selected from: $C_1$-$C_3$-alkyl-, —(CH$_2$)$_q$—X—(CH$_2$)$_p$—R$^3$; wherein said $C_1$-$C_3$-alkyl- group is optionally substituted with one $R^4$ group.

In another preferred embodiment, the invention relates to compounds of formula I, supra, wherein $R^{2a}$ represents a hydrogen atom or a halogen atom or a $C_1$-$C_3$-alkyl- group; wherein said $C_1$-$C_3$-alkyl- group is optionally substituted with one $R^4$ group.

In another preferred embodiment, the invention relates to compounds of formula I, supra, wherein $R^{2a}$ represents a hydrogen atom or a $C_1$-$C_3$-alkyl- group; wherein said $C_1$-$C_3$-alkyl- group is optionally substituted with one $R^4$ group.

In another preferred embodiment, the invention relates to compounds of formula I, supra, wherein $R^{2a}$ represents a hydrogen atom or a $C_1$-$C_3$-alkyl- group.

In another preferred embodiment, the invention relates to compounds of formula I, supra, wherein $R^{2b}$ represents a hydrogen atom or a halogen atom or a group selected from: $C_1$-$C_6$-alkyl-, $C_2$-$C_6$-alkenyl-, $C_2$-$C_6$-alkynyl-, $C_3$-$C_6$-cycloalkyl-, —(CH$_2$)$_q$—X—(CH$_2$)$_p$—R$^3$, halo-$C_1$-$C_3$-alkyl-, 3- to 10-membered heterocycloalkyl-, 4- to 10-membered heterocycloalkenyl-, cyano-; wherein said $C_1$-$C_6$-alkyl-, $C_2$-$C_6$-alkenyl-, $C_2$-$C_6$-alkynyl-, $C_3$-$C_6$-cycloalkyl-, 3- to 10-membered heterocycloalkyl- or 4- to 10-membered heterocycloalkenyl- group is optionally substituted, identically or differently, with 1, 2 or 3 $R^4$ groups.

In another preferred embodiment, the invention relates to compounds of formula I, supra, wherein $R^{2b}$ represents a hydrogen atom or a halogen atom or a group selected from: $C_1$-$C_3$-alkyl-, $C_2$-$C_4$-alkenyl-, $C_2$-$C_4$-alkynyl-, $C_3$-$C_6$-cycloalkyl-, —(CH$_2$)$_q$—X—(CH$_2$)$_p$—R$^3$, halo-$C_1$-$C_3$-alkyl-, 4- to 6-membered heterocycloalkyl-, 4- to 6-membered heterocycloalkenyl-, cyano-; wherein said $C_1$-$C_3$-alkyl-, $C_2$-$C_4$-alkenyl-, $C_2$-$C_4$-alkynyl-, $C_3$-$C_6$-cycloalkyl-, 4- to 6-membered heterocycloalkyl- or 4- to 6-membered heterocycloalkenyl- group is optionally substituted, identically or differently, with 1, 2 or 3 $R^4$ groups.

In another preferred embodiment, the invention relates to compounds of formula I, supra, wherein $R^{2b}$ represents a hydrogen atom or a halogen atom or a group selected from: $C_1$-$C_3$-alkyl-, $C_2$-$C_4$-alkynyl-, —(CH$_2$)$_q$—X—(CH$_2$)$_p$—R$^3$, halo-$C_1$-$C_3$-alkyl-; wherein said $C_1$-$C_3$-alkyl- group is optionally substituted, identically or differently, with 1, 2 or 3 $R^4$ groups.

In another preferred embodiment, the invention relates to compounds of formula I, supra, wherein $R^{2b}$ represents a hydrogen atom or a halogen atom or a group selected from: $C_1$-$C_3$-alkyl-, $C_2$-$C_4$-alkynyl-, —$(CH_2)_q$—X—$(CH_2)_p$—$R^3$, halo-$C_1$-$C_3$-alkyl-; wherein said $C_1$-$C_3$-alkyl- group is optionally substituted, identically or differently, with 1 or 2 $R^4$ groups.

In another preferred embodiment, the invention relates to compounds of formula I, supra, wherein $R^{2b}$ represents a hydrogen atom or a halogen atom or a group selected from: $C_1$-$C_3$-alkyl-, —$(CH_2)_q$—X—$(CH_2)_p$—$R^3$, halo-$C_1$-$C_3$-alkyl-; wherein said $C_1$-$C_3$-alkyl- group is optionally substituted with 1 $R^4$ groups.

In another preferred embodiment, the invention relates to compounds of formula I, supra, wherein $R^{2b}$ represents a hydrogen atom or a halogen atom or a group selected from: $C_1$-$C_3$-alkyl-, —$(CH_2)_q$—X—$(CH_2)_p$—$R^3$; wherein said $C_1$-$C_3$-alkyl- group is optionally substituted with 1 $R^4$ groups.

In another preferred embodiment, the invention relates to compounds of formula I, supra, wherein $R^{2b}$ represents a hydrogen atom or a halogen atom or a group selected from: $C_1$-$C_3$-alkyl-, —$(CH_2)_q$—X—$(CH_2)_p$—$R^3$.

In another preferred embodiment, the invention relates to compounds of formula I, supra, wherein one of $R^{2a}$ and $R^{2b}$ represents —$(CH_2)_q$—X—$(CH_2)_p$—$R^3$ and the other one of $R^{2a}$ and $R^{2b}$ represents a hydrogen atom or a halogen atom or a group selected from: $C_1$-$C_6$-alkyl-, $C_2$-$C_6$-alkynyl-, halo-$C_1$-$C_3$-alkyl-, cyano-; wherein said $C_1$-$C_6$-alkyl- group is optionally substituted, identically or differently, with 1, 2 or 3 $R^4$ groups.

In another preferred embodiment, the invention relates to compounds of formula I, supra, wherein one of $R^{2a}$ and $R^{2b}$ represents —$(CH_2)_q$—X—$(CH_2)_p$—$R^3$ and the other one of $R^{2a}$ and $R^{2b}$ represents a hydrogen atom or a halogen atom or a group selected from: $C_1$-$C_3$-alkyl-, halo-$C_1$-$C_3$-alkyl-, cyano-; wherein said $C_1$-$C_3$-alkyl- group is optionally substituted, identically or differently, with 1 or 2 $R^4$ groups.

In another preferred embodiment, the invention relates to compounds of formula I, supra, wherein one of $R^{2a}$ and $R^{2b}$ represents —$(CH_2)_q$—X—$(CH_2)_p$—$R^3$ and the other one of $R^{2a}$ and $R^{2b}$ represents a hydrogen atom or a halogen atom or a group selected from: $C_1$-$C_3$-alkyl-, halo-$C_1$-$C_3$-alkyl-, cyano-; wherein said $C_1$-$C_3$-alkyl- group is optionally substituted with one $R^4$ group.

In another preferred embodiment, the invention relates to compounds of formula I, supra, wherein one of $R^{2a}$ and $R^{2b}$ represents —$(CH_2)_q$—X—$(CH_2)_p$—$R^3$ and the other one of $R^{2a}$ and $R^{2b}$ represents a hydrogen atom or a halogen atom or a group selected from: $C_1$-$C_3$-alkyl-, halo-$C_1$-$C_3$-alkyl-, cyano-.

In another preferred embodiment, the invention relates to compounds of formula I, supra, wherein one of $R^{2a}$ and $R^{2b}$ represents —$(CH_2)_q$—X—$(CH_2)_p$—$R^3$ and the other one of $R^{2a}$ and $R^{2b}$ represents a hydrogen atom or a halogen atom or a $C_1$-$C_3$-alkyl- group.

In another preferred embodiment, the invention relates to compounds of formula I, supra, wherein one of $R^{2a}$ and $R^{2b}$ represents a hydrogen atom or a halogen atom or a group selected from: cyano-, $C_1$-$C_3$-alkyl-, halo-$C_1$-$C_3$-alkyl-; and the other one of $R^{2a}$ and $R^{2b}$ represents a group selected from $C_1$-$C_6$-alkyl-, $C_3$-$C_6$-cycloalkyl-, 3- to 10-membered heterocycloalkyl-, 4- to 10-membered heterocycloalkenyl-, aryl-, heteroaryl-, —$(CH_2)_q$—X—$(CH_2)_p$—$R^3$; wherein said $C_1$-$C_6$-alkyl-, $C_3$-$C_6$-cycloalkyl-, 3- to 10-membered heterocycloalkyl-, 4- to 10-membered heterocycloalkenyl-, aryl- or heteroaryl- group is optionally substituted, identically or differently, with 1, 2 or 3 $R^4$ groups.

In another preferred embodiment, the invention relates to compounds of formula I, supra, wherein one of $R^{2a}$ and $R^{2b}$ represents a hydrogen atom, and the other one of $R^{2a}$ and $R^{2b}$ represents a group selected from $C_1$-$C_6$-alkyl-, $C_3$-$C_6$-cycloalkyl-, 3- to 10-membered heterocycloalkyl-, 4- to 10-membered heterocycloalkenyl-, aryl-, heteroaryl-, —$(CH_2)_q$—X—$(CH_2)_p$—$R^3$; wherein said $C_1$-$C_6$-alkyl-, $C_3$-$C_6$-cycloalkyl-, 3- to 10-membered heterocycloalkyl-, 4- to 10-membered heterocycloalkenyl-, aryl- or heteroaryl- group is optionally substituted, identically or differently, with 1 or 2 $R^4$ groups.

In another preferred embodiment, the invention relates to compounds of formula I, supra, wherein X represents a single bond.

In another preferred embodiment, the invention relates to compounds of formula I, supra, wherein X represents a bivalent group selected from:
—S—, —S(=O)—, —S(=O)$_2$—.

In another preferred embodiment, the invention relates to compounds of formula I, supra, wherein X represents —O—.

In another preferred embodiment, the invention relates to compounds of formula I, supra, wherein X represents a bivalent group selected from:
—S(=O)—(NR$^{3a}$)—, —(NR$^{3a}$)—S(=O)—.

In another preferred embodiment, the invention relates to compounds of formula I, supra, wherein X represents a bivalent group selected from:
—S(=O)$_2$—(NR$^{3a}$)—, —(NR$^{3a}$)—S(=O)$_2$—.

In another preferred embodiment, the invention relates to compounds of formula I, supra, wherein X represents a bivalent group selected from:
—O—C(=O)—, —C(=S)—O—, —O—C(=S)—.

In another preferred embodiment, the invention relates to compounds of formula I, supra, wherein X represents —(NR$^{3a}$)—.

In another preferred embodiment, the invention relates to compounds of formula I, supra, wherein X represents a bivalent group selected from:
—C(=O)—, —C(=O)—O—, —C(=O)—(NR$^{3a}$)—, —(NR$^{3a}$)—C(=O)—, —(NR$^{3a}$)—C(=O)—(NR$^{3b}$)—, —O—C(=)—(NR$^{3a}$)—, —(NR$^{3a}$)—C(=O)—O—.

In another preferred embodiment, the invention relates to compounds of formula I, supra, wherein X represents a bivalent group selected from:
—C(=O)—, —C(=O)—O—, —C(=O)—(NR$^{3a}$)—, —(NR$^{3a}$)—C(=O)—, —(NR$^{3a}$)—C(=O)—(NR$^{3b}$)—, —O—C(=O)—(NR$^{3a}$)—, —(NR$^{3a}$)—C(=O)—O—
with the proviso that if X=—C(=O)— and both p and q are 0, then $R^3$ is not an aryl- group.

In another preferred embodiment, the invention relates to compounds of formula I, supra, wherein X represents a bivalent group selected from:
—(NR$^{3a}$)—C(=O)—(NR$^{3b}$)—, —O—C(=O)—(NR$^{3a}$)—, —(NR$^{3a}$)—C(=O)—O—.

In another preferred embodiment, the invention relates to compounds of formula I, supra, wherein X represents a bivalent group selected from:
—C(=O)—, —C(=O)—O—, —C(=O)—(NR$^{3a}$)—, —(NR$^{3a}$)—C(=O)—.

In another preferred embodiment, the invention relates to compounds of formula I, supra, wherein X represents a bivalent group selected from:
—C(=O)—, —C(=O)—O—, —C(=O)—(NR$^{3a}$)—, —(NR$^{3a}$)—C(=O)— with the proviso that if X=—C(=O)— and both p and q are 0, then $R^3$ is not an aryl- group.

In another preferred embodiment, the invention relates to compounds of formula I, supra, wherein X represents a bivalent group selected from:

—C(=O)—, —C(=O)—O—, —C(=O)—(NR$^{3a}$)—.

In another preferred embodiment, the invention relates to compounds of formula I, supra, wherein X represents a bivalent group selected from:
—C(=O)—, —C(=O)—O—, —C(=O)—(NR$^{3a}$)— with the proviso that if X=—C(=O)— and both p and q are 0, then R$^3$ is not an aryl- group.

In another preferred embodiment, the invention relates to compounds of formula I, supra, wherein X represents —C(=O)—.

In another preferred embodiment, the invention relates to compounds of formula I, supra, wherein X represents —C(=O)— with the proviso that if both p and q are 0, then R$^3$ is not an aryl- group.

In another preferred embodiment, the invention relates to compounds of formula I, supra, wherein X represents —C(=O)—O—.

In another preferred embodiment, the invention relates to compounds of formula I, supra, wherein X represents —C(=O)—(NR$^{3a}$)—.

In another preferred embodiment, the invention relates to compounds of formula I, supra, wherein X represents —(NR$^{3a}$)—C(=O)—.

In another preferred embodiment, the invention relates to compounds of formula I, supra, wherein X represents a bivalent group selected from:
—S(=O)$_2$—, —C(=O)—O—, —C(=O)—(NR$^{3a}$)—, —(NR$^{3a}$)—C(=O)—, —S(=O)$_2$—(NR$^{3a}$)—, —(NR$^{3a}$)—S(=O)$_2$—.

In another preferred embodiment, the invention relates to compounds of formula I, supra, wherein X represents a bivalent group selected from:
—S(=O)$_2$—, —C(=O)—O—, —C(=O)—(NR$^{3a}$)—, —S(=O)$_2$—(NR$^{3a}$)—.

In another preferred embodiment, the invention relates to compounds of formula I, supra, wherein X represents a bivalent group selected from:
—S(=O)$_2$—, —C(=O)—O—, —C(=O)—(NR$^{3a}$)—, —S(=O)$_2$—(NR$^{3a}$)—.

In another preferred embodiment, the invention relates to compounds of formula I, supra, wherein X represents a bivalent group selected from:
—S(=O)$_2$—, —C(=O)—O—, —C(=O)—(NR$^{3a}$)—.

In another preferred embodiment, the invention relates to compounds of formula I, supra, wherein X represents a bivalent group selected from:
—S(=O)$_2$—, —C(=O)—O—.

In another preferred embodiment, the invention relates to compounds of formula I, supra, wherein X represents a bivalent group selected from:
—S(=O)$_2$—, —C(=O)—(NR$^{3a}$)—.

In another preferred embodiment, the invention relates to compounds of formula I, supra, wherein X represents a bivalent group selected from:
—C(=O)—O—, —C(=O)—(NR$^{3a}$)—.

In another preferred embodiment, the invention relates to compounds of formula I, supra, wherein X represents —S(=O)$_2$—.

In another preferred embodiment, the invention relates to compounds of formula I, supra, wherein R$^3$ represents a hydrogen atom or a group selected from C$_1$-C$_6$-alkyl-, C$_3$-C$_6$-cycloalkyl-, 3- to 10-membered heterocycloalkyl-, aryl-, heteroaryl-, halo-C$_1$-C$_3$-alkyl-; wherein said C$_1$-C$_6$-alkyl-, C$_3$-C$_6$-cycloalkyl-, 3- to 10-membered heterocycloalkyl-, aryl- or heteroaryl- group is optionally substituted, identically or differently, with 1, 2 or 3 R$^4$ groups.

In another preferred embodiment, the invention relates to compounds of formula I, supra, wherein R$^3$ represents a hydrogen atom or a group selected from C$_1$-C$_6$-alkyl-, C$_3$-C$_6$-cycloalkyl-, 3- to 10-membered heterocycloalkyl-, halo-C$_1$-C$_3$-alkyl-; wherein said C$_1$-C$_6$-alkyl-, C$_3$-C$_6$-cycloalkyl- or 3- to 10-membered heterocycloalkyl- group is optionally substituted, identically or differently, with 1, 2 or 3 R$^4$ groups.

In another preferred embodiment, the invention relates to compounds of formula I, supra, wherein R$^3$ represents a hydrogen atom or a group selected from C$_1$-C$_3$-alkyl-, C$_3$-C$_6$-cycloalkyl-, 4- to 6-membered heterocycloalkyl-, halo-C$_1$-C$_3$-alkyl-; wherein said C$_1$-C$_3$-alkyl-, C$_3$-C$_6$-cycloalkyl- or 4- to 6-membered heterocycloalkyl- group is optionally substituted, identically or differently, with 1, 2 or 3 R$^4$ groups.

In another preferred embodiment, the invention relates to compounds of formula I, supra, wherein R$^3$ represents a hydrogen atom or a group selected from C$_1$-C$_3$-alkyl-, 4- to 6-membered heterocycloalkyl-; wherein said C$_1$-C$_3$-alkyl- or 4- to 6-membered heterocycloalkyl- group is optionally substituted, identically or differently, with 1, 2 or 3 R$^4$ groups.

In another preferred embodiment, the invention relates to compounds of formula I, supra, wherein R$^3$ represents a hydrogen atom or a group selected from C$_1$-C$_3$-alkyl-, aryl-; wherein said C$_1$-C$_3$-alkyl- aryl- group is optionally substituted, identically or differently, with 1, 2 or 3 R$^4$ groups.

In another preferred embodiment, the invention relates to compounds of formula I, supra, wherein R$^3$ represents a hydrogen atom or a group selected from C$_1$-C$_3$-alkyl-, aryl-; wherein said C$_1$-C$_3$-alkyl- aryl- group is optionally substituted, identically or differently, with 1, 2 or 3 R$^4$ groups, with the proviso that if R$^3$ is aryl, X is not —C(=O)— or p is different from 0 or q is different from 0.

In another preferred embodiment, the invention relates to compounds of formula I, supra, wherein R$^3$ represents a hydrogen atom or a group selected from C$_1$-C$_3$-alkyl-, 4- to 6-membered heterocycloalkyl-; wherein said C$_1$-C$_3$-alkyl- or 4- to 6-membered is optionally substituted with one R$^4$ group.

In another preferred embodiment, the invention relates to compounds of formula I, supra, wherein R$^3$ represents an aryl- or heteroaryl- group; wherein said aryl- or heteroaryl- group is optionally substituted with one R$^4$ group.

In another preferred embodiment, the invention relates to compounds of formula I, supra, wherein R$^3$ represents an aryl- or heteroaryl- group; wherein said aryl- or heteroaryl- group is optionally substituted with one R$^4$ group, with the proviso that if R$^3$ is aryl, X is not —C(=O)— or p is different from 0 or q is different from 0.

In another preferred embodiment, the invention relates to compounds of formula I, supra, wherein R$^3$ represents an aryl- group; wherein said aryl- group is optionally substituted with one R$^4$ group.

In another preferred embodiment, the invention relates to compounds of formula I, supra, wherein R$^3$ represents an aryl- group; wherein said aryl- group is optionally substituted with one R$^4$ group, with the proviso that X is not —C(=O)— or p is different from 0 or q is different from 0.

In another preferred embodiment, the invention relates to compounds of formula I, supra, wherein R$^3$ represents a C$_1$-C$_3$-alkyl- group; wherein said C$_1$-C$_3$-alkyl- group is optionally substituted with one R$^4$ group.

In another preferred embodiment, the invention relates to compounds of formula I, supra, wherein R$^3$ represents a hydrogen atom.

In another preferred embodiment, the invention relates to compounds of formula I, supra, wherein R$^{3a}$ represents a hydrogen atom or a group selected from C$_1$-C$_3$-alkyl-, C$_3$-C$_6$-cycloalkyl-, 4- to 6-membered heterocycloalkyl-, aryl-, heteroaryl-, halo-$C_1$-$C_3$-alkyl-; wherein said $C_1$-$C_3$-alkyl-, $C_3$-$C_6$-cycloalkyl-, 4- to 6-membered heterocycloalkyl-, aryl- or heteroaryl- group is optionally substituted, identically or differently, with 1, 2, 3, 4 or 5 $R^4$ groups.

In another preferred embodiment, the invention relates to compounds of formula I, supra, wherein $R^{3a}$ represents a hydrogen atom or a group selected from $C_1$-$C_3$-alkyl-, $C_3$-$C_6$-cycloalkyl-, 4- to 6-membered heterocycloalkyl-, halo-$C_1$-$C_3$-alkyl-; wherein said $C_1$-$C_3$-alkyl-, $C_3$-$C_6$-cycloalkyl- or 4- to 6-membered heterocycloalkyl- group is optionally substituted, identically or differently, with 1, 2 or 3 $R^4$ groups.

In another preferred embodiment, the invention relates to compounds of formula I, supra, wherein $R^{3a}$ represents a hydrogen atom or a $C_1$-$C_6$-alkyl- group; wherein said $C_1$-$C_6$-alkyl- group is optionally substituted, identically or differently, with 1, 2 or 3 $R^4$ groups.

In another preferred embodiment, the invention relates to compounds of formula I, supra, wherein $R^{3a}$ represents a hydrogen atom or a $C_1$-$C_6$-alkyl- group; wherein said $C_1$-$C_6$-alkyl- group is optionally substituted, identically or differently, with 1 or 2 $R^4$ groups.

In another preferred embodiment, the invention relates to compounds of formula I, supra, wherein $R^{3a}$ represents a hydrogen atom or a $C_1$-$C_3$-alkyl- group; wherein said $C_1$-$C_3$-alkyl- group is optionally substituted, identically or differently, with 1 or 2 $R^4$ groups.

In another preferred embodiment, the invention relates to compounds of formula I, supra, wherein $R^{3a}$ represents a hydrogen atom or a $C_1$-$C_3$-alkyl- group; wherein said $C_1$-$C_3$-alkyl- group is optionally substituted with one $R^4$ group.

In another preferred embodiment, the invention relates to compounds of formula I, supra, wherein $R^{3a}$ represents a hydrogen atom or a $C_1$-$C_3$-alkyl- group.

In another preferred embodiment, the invention relates to compounds of formula I, supra, wherein $R^{3b}$ represents a hydrogen atom or a group selected from $C_1$-$C_3$-alkyl-, $C_3$-$C_6$-cycloalkyl-, 4- to 6-membered heterocycloalkyl-, aryl-, heteroaryl-, halo-$C_1$-$C_3$-alkyl-; wherein said $C_1$-$C_3$-alkyl-, $C_3$-$C_6$-cycloalkyl-, 4- to 6-membered heterocycloalkyl-, aryl- or heteroaryl- group is optionally substituted, identically or differently, with 1, 2, 3, 4 or 5 $R^4$ groups.

In another preferred embodiment, the invention relates to compounds of formula I, supra, wherein $R^{3b}$ represents a hydrogen atom or a group selected from $C_1$-$C_3$-alkyl-, $C_3$-$C_6$-cycloalkyl-, 4- to 6-membered heterocycloalkyl-, halo-$C_1$-$C_3$-alkyl-; wherein said $C_1$-$C_3$-alkyl-, $C_3$-$C_6$-cycloalkyl- or 4- to 6-membered heterocycloalkyl- group is optionally substituted, identically or differently, with 1, 2 or 3 $R^4$ groups.

In another preferred embodiment, the invention relates to compounds of formula I, supra, wherein $R^{3b}$ represents a hydrogen atom or a $C_1$-$C_6$-alkyl- group; wherein said $C_1$-$C_6$-alkyl- group is optionally substituted, identically or differently, with 1, 2 or 3 $R^4$ groups.

In another preferred embodiment, the invention relates to compounds of formula I, supra, wherein $R^{3b}$ represents a hydrogen atom or a $C_1$-$C_6$-alkyl- group; wherein said $C_1$-$C_6$-alkyl- group is optionally substituted, identically or differently, with 1 or 2 $R^4$ groups.

In another preferred embodiment, the invention relates to compounds of formula I, supra, wherein $R^{3b}$ represents a hydrogen atom or a $C_1$-$C_3$-alkyl- group; wherein said $C_1$-$C_3$-alkyl- group is optionally substituted, identically or differently, with 1 or 2 $R^4$ groups.

In another preferred embodiment, the invention relates to compounds of formula I, supra, wherein $R^{3b}$ represents a hydrogen atom or a $C_1$-$C_3$-alkyl- group; wherein said $C_1$-$C_3$-alkyl- group is optionally substituted with one $R^4$ group.

In another preferred embodiment, the invention relates to compounds of formula I, supra, wherein $R^{3b}$ represents a hydrogen atom or a $C_1$-$C_3$-alkyl- group.

In another preferred embodiment, the invention relates to compounds of formula I, supra, wherein $R^{3b}$ represents a hydrogen atom.

In another preferred embodiment, the invention relates to compounds of formula I, supra, wherein $R^3$ together with $R^{3a}$ or $R^{3b}$ represent a 3- to 10-membered heterocycloalkyl- or a 4- to 10-membered heterocycloalkenyl- group, which is optionally substituted, one or more times, identically or differently, with halo-, hydroxyl, cyano-.

In another preferred embodiment, the invention relates to compounds of formula I, supra, wherein $R^3$ together with $R^{3a}$ represent a 3- to 10-membered heterocycloalkyl- or a 4- to 10-membered heterocycloalkenyl- group, which is optionally substituted, one or more times, identically or differently, with halo-, hydroxyl, cyano-.

In another preferred embodiment, the invention relates to compounds of formula I, supra, wherein $R^3$ together with $R^{3a}$ or $R^{3b}$ represent a 3- to 10-membered heterocycloalkyl- group, which is optionally substituted, one or more times, identically or differently, with halo-, hydroxyl, cyano-.

In another preferred embodiment, the invention relates to compounds of formula I, supra, wherein $R^3$ together with $R^{3a}$ or $R^{3b}$ represent a 3- to 10-membered heterocycloalkyl- group, which is optionally substituted, one or more times, identically or differently, with halo-.

In another preferred embodiment, the invention relates to compounds of formula I, supra, wherein $R^3$ together with $R^{3a}$ represent a 3- to 10-membered heterocycloalkyl- group, which is optionally substituted, one or more times, identically or differently, with halo-.

In another preferred embodiment, the invention relates to compounds of formula I, supra, wherein $R^3$ together with $R^{3a}$ represent a 4- to 7-membered heterocycloalkyl- group, which is optionally substituted, one or more times, identically or differently, with halo-.

In another preferred embodiment, the invention relates to compounds of formula I, supra, wherein $R^3$ together with $R^{3a}$ represent a 5- to 6-membered heterocycloalkyl- group, which is optionally substituted, one or more times, identically or differently, with halo-.

In another preferred embodiment, the invention relates to compounds of formula I, supra, wherein $R^4$ represents halo-, hydroxy-, cyano-, nitro-, $C_1$-$C_6$-alkyl-, $C_2$-$C_6$-alkenyl-, $C_2$-$C_6$-alkynyl-, halo-$C_1$-$C_6$-alkyl-, $C_1$-$C_6$-alkoxy-, halo-$C_1$-$C_6$-alkoxy-, hydroxy-$C_1$-$C_6$-alkyl-, $C_1$-$C_6$-alkoxy-$C_1$-$C_6$-alkyl- or halo-$C_1$-$C_6$-alkoxy-$C_1$-$C_6$-alkyl-.

In another preferred embodiment, the invention relates to compounds of formula I, supra, wherein $R^4$ represents halo-, hydroxy-, cyano-, nitro-, $C_1$-$C_3$-alkyl-, $C_2$-$C_3$-alkenyl-, $C_2$-$C_3$-alkynyl-, halo-$C_1$-$C_3$-alkyl-, $C_1$-$C_3$-alkoxy-, halo-$C_1$-$C_3$-alkoxy-, hydroxy-$C_1$-$C_3$-alkyl-, $C_1$-$C_3$-alkoxy-$C_1$-$C_3$-alkyl- or halo-$C_1$-$C_3$-alkoxy-$C_1$-$C_3$-alkyl-.

In another preferred embodiment, the invention relates to compounds of formula I, supra, wherein $R^4$ represents halo-, hydroxy-, $C_1$-$C_3$-alkyl-, $C_2$-$C_3$-alkenyl-, $C_2$-$C_3$-alkynyl-, halo-$C_1$-$C_3$-alkyl-, $C_1$-$C_3$-alkoxy-, halo-$C_1$-$C_3$-alkoxy-, hydroxy-$C_1$-$C_3$-alkyl-, $C_1$-$C_3$-alkoxy-$C_1$-$C_3$-alkyl- or halo-$C_1$-$C_3$-alkoxy-$C_1$-$C_3$-alkyl-.

In another preferred embodiment, the invention relates to compounds of formula I, supra, wherein $R^4$ represents halo-, $C_1$-$C_3$-alkyl-, $C_2$-$C_3$-alkenyl-, $C_2$-$C_3$-alkynyl-, halo-$C_1$-$C_3$-alkyl-, $C_1$-$C_3$-alkoxy-, halo-$C_1$-$C_3$-alkoxy-, $C_1$-$C_3$-alkoxy-$C_1$-$C_3$-alkyl- or halo-$C_1$-$C_3$-alkoxy-$C_1$-$C_3$-alkyl-.

In another preferred embodiment, the invention relates to compounds of formula I, supra, wherein $R^4$ represents halo-, $C_1$-$C_3$-alkyl-, halo-$C_1$-$C_3$-alkyl-, $C_1$-$C_3$-alkoxy- or halo-$C_1$-$C_3$-alkoxy-.

In another preferred embodiment, the invention relates to compounds of formula I, supra, wherein $R^4$ represents halo-, hydroxy or $C_1$-$C_3$-alkyl-.

In another preferred embodiment, the invention relates to compounds of formula I, supra, wherein $R^4$ represents $C_1$-$C_3$-alkyl-.

In another preferred embodiment, the invention relates to compounds of formula I, supra, wherein $R^4$ represents $R^5$—O—, —C(=O)—$R^5$, —O—C(=O)—$R^5$, —C(=O)—O—$R^5$, —N($R^{5a}$)—C(=O)—$R^{5b}$, —N($R^{5a}$)—C(=O)—N$R^{5b}R^{5c}$, —N$R^{5a}R^{5b}$, —C(=O)—N$R^{5a}R^{5b}$, $R^5$—S—, $R^5$—S(=O)—, $R^5$—S(=O)$_2$—, —N($R^{5a}$)—S(=O)—$R^{5b}$, —S(=O)—N$R^{5a}R^{5b}$, —N($R^{5a}$)—S(=O)$_2$—$R^{5b}$, —S(=O)$_2$—N$R^{5a}R^{5b}$, —S(=O)(=N$R^{5a}$)$R^{5b}$, —S(=O)(=N$R^{5a}$)$R^{5b}$ or —N=S(=O)($R^{5a}$)$R^{5b}$.

In another preferred embodiment, the invention relates to compounds of formula I, supra, wherein $R^4$ represents $R^5$—O—, —C(=O)—$R^5$, —O—C(=O)—$R^5$ or —C(=O)—O—$R^5$.

In another preferred embodiment, the invention relates to compounds of formula I, supra, wherein $R^4$ represents —N($R^{5a}$)—C(=O)—$R^{5b}$, —N($R^{5a}$)—C(=O)—N$R^{5b}R^{5c}$, —N$R^{5a}R^{5b}$ or —C(=O)—N$R^{5a}R^{5b}$.

In another preferred embodiment, the invention relates to compounds of formula I, supra, wherein $R^4$ represents $R^5$—S—, $R^5$—S(=O)— or $R^5$—S(=O)$_2$—.

In another preferred embodiment, the invention relates to compounds of formula I, supra, wherein $R^4$ represents —N($R^{5a}$)—S(=O)—$R^{5b}$, —S(=O)—N$R^{5a}R^{5b}$, —N($R^{5a}$)—S(=O)$_2$—$R^{5b}$, —S(=O)$_2$—N$R^{5a}R^{5b}$, —S(=O)(=N$R^{5a}$)$R^{5b}$, —S(=O)(=N$R^{5a}$)$R^{5b}$ or —N=S(=O)($R^{5a}$)$R^{5b}$.

In another preferred embodiment, the invention relates to compounds of formula I, supra, wherein $R^4$ represents $R^5$—S(=O)—, $R^5$—S(=O)$_2$—, —C(=O)—$R^5$, —O—C(=O)—$R^5$, —C(=O)—O—$R^5$, —N($R^{5a}$)—C(=O)—$R^{5b}$, —N$R^{5a}R^{5b}$ or —C(=O)—N$R^{5a}R^{5b}$.

In another preferred embodiment, the invention relates to compounds of formula I, supra, wherein $R^5$ represents a hydrogen atom or a $C_1$-$C_6$-alkyl- group.

In another preferred embodiment, the invention relates to compounds of formula I, supra, wherein $R^5$ represents a hydrogen atom or a $C_1$-$C_3$-alkyl- group.

In another preferred embodiment, the invention relates to compounds of formula I, supra, wherein $R^{5a}$ represents a hydrogen atom or a $C_1$-$C_6$-alkyl- group.

In another preferred embodiment, the invention relates to compounds of formula I, supra, wherein $R^{5a}$ represents a hydrogen atom or a $C_1$-$C_3$-alkyl- group.

In another preferred embodiment, the invention relates to compounds of formula I, supra, wherein $R^{5b}$ represents a hydrogen atom or a $C_1$-$C_6$-alkyl- group.

In another preferred embodiment, the invention relates to compounds of formula I, supra, wherein $R^{5b}$ represents a hydrogen atom or a $C_1$-$C_3$-alkyl- group.

In another preferred embodiment, the invention relates to compounds of formula I, supra, wherein $R^{5c}$ represents a hydrogen atom or a $C_1$-$C_6$-alkyl- group.

In another preferred embodiment, the invention relates to compounds of formula I, supra, wherein $R^{5c}$ represents a hydrogen atom or a $C_1$-$C_3$-alkyl- group.

In another preferred embodiment, the invention relates to compounds of formula I, supra, wherein $R^{5a}$ and $R^{5b}$, or
$R^{5a}$ and $R^{5c}$, or
$R^{5b}$ and $R^{5c}$ together may form a $C_2$-$C_6$-alkylene group, in which optionally one methylene can be replaced by —O—, —C(=O)—, —NH—, or —N($C_1$-$C_4$-alkyl)-.

In another preferred embodiment, the invention relates to compounds of formula I, supra, wherein $R^{5a}$ and $R^{5b}$ together form a $C_3$-$C_4$ alkylene group.

In another preferred embodiment, the invention relates to compounds of formula I, supra, wherein $R^{5a}$ and $R^{5c}$ together form a $C_3$-$C_4$ alkylene group.

In another preferred embodiment, the invention relates to compounds of formula I, supra, wherein $R^{5b}$ and $R^{5c}$ together form a $C_3$-$C_4$ alkylene group.

In another preferred embodiment, the invention relates to compounds of formula I, supra, wherein p represents an integer of 0, 1 or 2.

In another preferred embodiment, the invention relates to compounds of formula I, supra, wherein p represents an integer of 0.

In another preferred embodiment, the invention relates to compounds of formula I, supra, wherein p represents an integer of 1.

In another preferred embodiment, the invention relates to compounds of formula I, supra, wherein p represents an integer of 2.

In another preferred embodiment, the invention relates to compounds of formula I, supra, wherein q represents an integer of 0, 1 or 2.

In another preferred embodiment, the invention relates to compounds of formula I, supra, wherein q represents an integer of 0.

In another preferred embodiment, the invention relates to compounds of formula I, supra, wherein q represents an integer of 1.

In another preferred embodiment, the invention relates to compounds of formula I, supra, wherein q represents an integer of 2.

In another preferred embodiment, the invention relates to compounds of formula I, supra, wherein p represents an integer of 0 and q represents an integer of 1.

In another preferred embodiment, the invention relates to compounds of formula I, supra, wherein p represents an integer of 1 and q represents an integer of 0.

In another preferred embodiment, the invention relates to compounds of formula I, supra, wherein p represents an integer of 0 and q represents an integer of 0.

In another preferred embodiment, the invention relates to compounds of formula I, supra, wherein p represents an integer of 1 and q represents an integer of 1.

In a further embodiment of the above-mentioned aspect, the invention relates to compounds of formula I, according to any of the above-mentioned embodiments, in the form of or a stereoisomer, a tautomer, an N-oxide, a hydrate, a solvate, or a salt thereof, or a mixture of same.

It is to be understood that the present invention relates also to any combination of the preferred embodiments described above.

Some examples of combinations are given hereinafter. However, the invention is not limited to these combinations.

In a preferred embodiment, the invention relates to compounds of formula I, supra, in which:

$R^{1a}$ represents a hydrogen or halogen atom or a hydroxy-, cyano-, —N$R^{5a}R^{5b}$, $C_1$-$C_6$-alkyl-, halo-$C_1$-$C_6$-alkyl-, $C_1$-$C_6$-alkoxy-, or a halo-$C_1$-$C_6$-alkoxy- group;

$R^{1b}$ represents a hydrogen or halogen atom or a $C_1$-$C_6$-alkyl-, halo-$C_1$-$C_6$-alkyl-, $C_1$-$C_6$-alkoxy-, halo-$C_1$-$C_6$-alkoxy- group;

$R^{1c}$ represents a hydrogen or halogen atom or a $C_1$-$C_6$-alkyl-, halo-$C_1$-$C_6$-alkyl-, $C_1$-$C_6$-alkoxy-, halo-$C_1$-$C_6$-alkoxy- group;

Y represents N or $CR^{2a}$;

Z represents $CR^{2b}$;

$R^{2a}$ represents a hydrogen atom or a halogen atom or a group selected from:
  $C_1$-$C_6$-alkyl-, $C_3$-$C_6$-cycloalkyl-, aryl-, heteroaryl-, halo-$C_1$-$C_3$-alkyl-, cyano-, 3- to 10-membered heterocycloalkyl-, 4- to 10-membered heterocycloalkenyl-, —$(CH_2)_q$—X—$(CH_2)_p$—$R^3$; wherein said $C_1$-$C_6$-alkyl-, $C_3$-$C_6$-cycloalkyl-, 3- to 10-membered heterocycloalkyl-, 4- to 10-membered heterocycloalkenyl-, aryl- or heteroaryl- group is optionally substituted, identically or differently, with 1, 2 or 3 $R^4$ groups;

$R^{2b}$ represents a hydrogen atom or a halogen atom or a group selected from:
  $C_1$-$C_6$-alkyl-, $C_3$-$C_6$-cycloalkyl-, —$(CH_2)_q$—X—$(CH_2)_p$—$R^3$, halo-$C_1$-$C_3$-alkyl-, 3- to 10-membered heterocycloalkyl-, 4- to 10-membered heterocycloalkenyl-, cyano-; wherein said $C_1$-$C_6$-alkyl-, $C_3$-$C_6$-cycloalkyl-, 3- to 10-membered heterocycloalkyl- or 4- to 10-membered heterocycloalkenyl- group is optionally substituted, identically or differently, with 1, 2 or 3 $R^4$ groups;

X represents a single bond or a bivalent group selected from: —O—, —S—, —S(=O)—, —S(=O)$_2$—, —S(=O)—(NR$^{3a}$)—, —(NR$^{3a}$)—S(=O)—, —C(=O)—, —(NR$^{3a}$)—, —C(=O)—O—, —O—C(=O)—, —C(=S)—O—, —O—C(=S)—, —C(=O)—(NR$^{3a}$)—, —(NR$^{3a}$)—C(=O)—, —(NR$^{3a}$)—C(=O)—(NR$^{3b}$)—, —O—C(=O)—(NR$^{3a}$)—, —(NR$^{3a}$)—C(=O)—O—;

$R^3$ represents a hydrogen atom or a group selected from $C_1$-$C_6$-alkyl-, $C_3$-$C_6$-cycloalkyl-, 3- to 10-membered heterocycloalkyl-, aryl-, heteroaryl-, halo-$C_1$-$C_3$-alkyl-;
  wherein said $C_1$-$C_6$-alkyl-, $C_3$-$C_6$-cycloalkyl-, 3- to 10-membered heterocycloalkyl-, aryl- or heteroaryl- group is optionally substituted, identically or differently, with 1, 2, 3, 4 or 5 $R^4$ groups;

$R^{3a}$ represents a hydrogen atom or a group selected from $C_1$-$C_6$-alkyl-, $C_3$-$C_6$-cycloalkyl-, 3- to 10-membered heterocycloalkyl-, aryl-, heteroaryl-, halo-$C_1$-$C_3$-alkyl-;
  wherein said $C_1$-$C_6$-alkyl-, $C_3$-$C_6$-cycloalkyl-, 3- to 10-membered heterocycloalkyl-, aryl- or heteroaryl- group is optionally substituted, identically or differently, with 1, 2, 3, 4 or 5 $R^4$ groups;

$R^{3b}$ represents a hydrogen atom or a group selected from $C_1$-$C_6$-alkyl-, $C_3$-$C_6$-cycloalkyl-, 3- to 10-membered heterocycloalkyl-, aryl-, heteroaryl-, halo-$C_1$-$C_3$-alkyl-;
  wherein said $C_1$-$C_6$-alkyl-, $C_3$-$C_6$-cycloalkyl-, 3- to 10-membered heterocycloalkyl-, aryl- or heteroaryl- group is optionally substituted, identically or differently, with 1, 2, 3, 4 or 5 $R^4$ groups; or $R^3$ together with $R^{3a}$ or $R^{3b}$ represent a 3- to 10-membered heterocycloalkyl- or a 4- to 10-membered heterocycloalkenyl- group, which is optionally substituted, one or more times, identically or differently, with halo-, hydroxyl-, cyano-;

$R^4$ represents halo-, hydroxy-, oxo- (O=), cyano-, nitro-, $C_1$-$C_6$-alkyl-, $C_2$-$C_6$-alkenyl-, $C_2$-$C_6$-alkynyl-, halo-$C_1$-$C_6$-alkyl-, $C_1$-$C_6$-alkoxy-, halo-$C_1$-$C_6$-alkoxy-, hydroxy-$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-, $R^5$—O—, —C(=O)—$R^5$, —C(=O)—O—$R^5$, —O—C(=O)—$R^5$, —N($R^{5a}$)—C(=O)—$R^{5b}$, —N($R^{5a}$)—C(=O)—NR$^{5b}$R$^{5c}$, —NR$^{5a}$R$^{5b}$, —C(=O)—NR$^{5a}$R$^{5b}$, R$^5$—S—, R$^5$—S(=O)—, R$^5$—S(=O)$_2$—, —N($R^{5a}$)—S(=O)—$R^{5b}$, —S(=O)—NR$^{5a}$R$^{5b}$, —N($R^{5a}$)—S(=O)$_2$—$R^{5b}$, —S(=O)$_2$—NR$^{5a}$R$^{5b}$, —S(=O)(=NR$^{5a}$)R$^{5b}$, —S(=O)(=NR$^{5a}$)R$^{5b}$ or —N=S(=O)(R$^{5a}$)R$^{5b}$;

$R^5$ represents a hydrogen atom, a $C_1$-$C_6$-alkyl- or $C_3$-$C_6$-cycloalkyl- group;

$R^{5a}$ represents a hydrogen atom, a $C_1$-$C_6$-alkyl- or $C_3$-$C_6$-cycloalkyl- group;

$R^{5b}$ represents a hydrogen atom, a $C_1$-$C_6$-alkyl- or $C_3$-$C_6$-cycloalkyl- group;

$R^{5c}$ represents a hydrogen atom, a $C_1$-$C_6$-alkyl- or $C_3$-$C_6$-cycloalkyl- group; or $R^{5a}$ and $R^{5b}$, or
$R^{5a}$ and $R^{5c}$, or
$R^{5b}$ and $R^{5c}$
together form a $C_2$-$C_6$-alkylene group, in which optionally one methylene can be replaced by —O—, —C(=O)—, —NH—, or —N($C_1$-$C_4$-alkyl)-;

p represents an integer of 0, 1 or 2;
q represents an integer of 0, 1 or 2;

or a tautomer, an N-oxide, a hydrate, a solvate, or a salt thereof, or a mixture of same.

In another preferred embodiment, the invention relates to compounds of formula I, supra, in which:

$R^{1a}$ represents a hydrogen or halogen atom or a $C_1$-$C_3$-alkyl-, —NR$^{5a}$R$^{5b}$, halo-$C_1$-$C_3$-alkyl-, $C_1$-$C_3$-alkoxy-, or a halo-$C_1$-$C_3$-alkoxy- group;

$R^{1b}$ represents a hydrogen or halogen atom or a $C_1$-$C_3$-alkyl-, halo-$C_1$-$C_3$-alkyl-, $C_1$-$C_3$-alkoxy-, halo-$C_1$-$C_3$-alkoxy- group;

$R^{1c}$ represents a hydrogen or halogen atom or a $C_1$-$C_3$-alkyl-, halo-$C_1$-$C_3$-alkyl-, $C_1$-$C_3$-alkoxy-, halo-$C_1$-$C_3$-alkoxy- group;

Y represents N or $CR^{2a}$;
Z represents $CR^{2b}$;

$R^{2a}$ represents a hydrogen atom or a halogen atom or a group selected from: $C_1$-$C_3$-alkyl-, halo-$C_1$-$C_3$-alkyl-, —$(CH_2)_q$—X—$(CH_2)_p$—$R^3$; wherein said $C_1$-$C_3$-alkyl- group is optionally substituted, identically or differently, with 1, 2 or 3 $R^4$ groups;

$R^{2b}$ represents a hydrogen atom or a halogen atom or a group selected from: $C_1$-$C_3$-alkyl-, —$(CH_2)_q$—X—$(CH_2)_p$—$R^3$, halo-$C_1$-$C_3$-alkyl-; wherein said $C_1$-$C_3$-alkyl- group is optionally substituted, identically or differently, with 1, 2 or 3 $R^4$ groups;

X represents a single bond or a bivalent group selected from: —O—, —S(=O)$_2$—, —S(=O)—(NR$^{3a}$)—, —(NR$^{3a}$)—S(=O)—, —C(=O)—, —(NR$^{3a}$)—, —C(=O)—O—, —C(=O)—(NR$^{3a}$)—, —(NR$^{3a}$)—C(=O)—, —(NR$^{3a}$)—C(=O)—(NR$^{3b}$)—, —O—C(=O)—(NR$^{3a}$)—, —(NR$^{3a}$)—C(=O)—O—;

$R^3$ represents a hydrogen atom or a group selected from $C_1$-$C_3$-alkyl-, 4- to 6-membered heterocycloalkyl-; wherein said $C_1$-$C_3$-alkyl- or 4- to 6-membered heterocycloalkyl- group is optionally substituted, identically or differently, with 1, 2 or 3 $R^4$ groups;

$R^{3a}$ represents a hydrogen atom or a $C_1$-$C_3$-alkyl- group; wherein said $C_1$-$C_3$-alkyl- group is optionally substituted with one $R^4$ group;

$R^{3b}$ represents a hydrogen atom or a $C_1$-$C_3$-alkyl- group; or $R^3$ together with $R^{3a}$ or $R^{3b}$ represent a 3- to 10-membered heterocycloalkyl- or a 4- to 10-membered heterocycloalkenyl- group, which is optionally substituted, one or more times, identically or differently, with halo-, hydroxyl-, cyano-;

$R^4$ represents halo-, hydroxy-, cyano-, $C_1$-$C_6$-alkyl-, $C_2$-$C_6$-alkenyl-, $C_2$-$C_6$-alkynyl-, halo-$C_1$-$C_6$-alkyl-, $C_1$-$C_6$-alkoxy-, halo-$C_1$-$C_6$-alkoxy-, hydroxy-$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-, $R^5$—O—, —C(=O)—$R^5$, —C(=O)—O—$R^5$, —O—C(=O)—$R^5$, —N($R^{5a}$)—C(=O)—$R^{5b}$, —N($R^{5a}$)—C(=O)—NR$^{5b}$R$^{5c}$, —NR$^{5a}$R$^{5b}$, —C(=O)—NR$^{5a}$R$^{5b}$, $R^5$—S—, $R^5$—S(=O)—, $R^5$—S(=O)$_2$—, —N($R^{5a}$)—S(=O)—$R^{5b}$, —S(=O)—NR$^{5a}$R$^{5b}$, —N($R^{5a}$)—S(=O)$_2$—$R^{5b}$, —S(=O)$_2$—NR$^{5a}$R$^{5b}$, —S(=O)(=N$R^{5a}$)$R^{5b}$, —S(=O)(=N$R^{5a}$)$R^{5b}$ or —N=S(=O)($R^{5a}$)$R^{5b}$;

$R^5$ represents a hydrogen atom, a $C_1$-$C_3$-alkyl- or $C_3$-$C_6$-cycloalkyl- group;

$R^{5a}$ represents a hydrogen atom, a $C_1$-$C_3$-alkyl- or $C_3$-$C_6$-cycloalkyl- group;

$R^{5b}$ represents a hydrogen atom, a $C_1$-$C_3$-alkyl- or $C_3$-$C_6$-cycloalkyl- group;

$R^{5c}$ represents a hydrogen atom, a $C_1$-$C_3$-alkyl- or $C_3$-$C_6$-cycloalkyl- group; or $R^{5a}$ and $R^{5b}$, or
$R^{5a}$ and $R^{5c}$, or
$R^{5b}$ and $R^{5c}$
together form a $C_2$-$C_6$-alkylene group, in which optionally one methylene can be replaced by —O—, —C(=O)—, —NH—, or —N($C_1$-$C_4$-alkyl)-;

p represents an integer of 0 or 1;
q represents an integer of 0 or 1;
or a tautomer, an N-oxide, a hydrate, a solvate, or a salt thereof, or a mixture of same.

In another preferred embodiment, the invention relates to compounds of formula I, supra, in which:

$R^{1a}$ represents a hydrogen atom or a halogen atom or a hydroxy-, cyano-, $C_1$-$C_3$-alkyl-, halo-$C_1$-$C_3$-alkyl-, $C_1$-$C_3$-alkoxy- group;

$R^{1b}$ represents a hydrogen atom or a halogen atom or a cyano- group;

$R^{1c}$ represents a hydrogen or a halogen atom or a cyano group;

Y represents N or $CR^{2a}$;
Z represents $CR^{2b}$;
one of $R^{2a}$ and $R^{2b}$
represents —(CH$_2$)$_q$—X—(CH$_2$)$_p$—$R^3$; and
the other one of $R^{2a}$ and $R^{2b}$
represents a hydrogen atom or a halogen atom or a group selected from:
$C_1$-$C_6$-alkyl-, halo-$C_1$-$C_3$-alkyl-, cyano-; wherein said $C_1$-$C_6$-alkyl- group is optionally substituted, identically or differently, with 1, 2 or 3 $R^4$ groups;

X represents a single bond or a bivalent group selected from: —O—, —S—, —S(=O)$_2$—, —C(=O)—, —(NR$^{3a}$)—, —C(=O)—O—, —O—C(=O)—, —C(=O)—(NR$^{3a}$)—, —(NR$^{3a}$)—C(=O)—;

$R^3$ represents a hydrogen atom or a group selected from $C_1$-$C_3$-alkyl-, $C_3$-$C_6$-cycloalkyl-, 4- to 6-membered heterocycloalkyl-, halo-$C_1$-$C_3$-alkyl-;
wherein said $C_1$-$C_3$-alkyl-, $C_3$-$C_6$-cycloalkyl- or 4- to 6-membered heterocycloalkyl- group is optionally substituted, identically or differently, with 1 or 2 $R^4$ groups;

$R^{3a}$ represents a hydrogen atom or a group selected from $C_1$-$C_3$-alkyl-, halo-$C_1$-$C_3$-alkyl-;
wherein said $C_1$-$C_3$-alkyl- group is optionally substituted, identically or differently, with 1 or 2 $R^4$ groups;

$R^{3b}$ represents a hydrogen atom or a group selected from $C_1$-$C_3$-alkyl-, halo-$C_1$-$C_3$-alkyl-;
wherein said $C_1$-$C_3$-alkyl- group is optionally substituted, identically or differently, with 1 or 2 $R^4$ groups; or $R^3$ together with $R^{3a}$ or $R^{3b}$ represent a 3- to 10-membered heterocycloalkyl- or a 4- to 10-membered heterocycloalkenyl- group, which is optionally substituted, one or more times, identically or differently, with halo-, hydroxyl-, cyano-;

$R^4$ represents halo-, hydroxy-, cyano-, $C_1$-$C_3$-alkyl-, $C_2$-$C_3$-alkenyl-, $C_2$-$C_3$-alkynyl-, halo-$C_1$-$C_3$-alkyl-, $C_1$-$C_3$-alkoxy-, halo-$C_1$-$C_3$-alkoxy-, hydroxy-$C_1$-$C_3$-alkyl-, $C_1$-$C_3$-alkoxy-$C_1$-$C_3$-alkyl-, halo-$C_1$-$C_3$-alkoxy-$C_1$-$C_3$-alkyl-, $R^5$—O—, —C(=O)—$R^5$, —C(=O)—O—$R^5$, —O—C(=O)—$R^5$, —N($R^{5a}$)—C(=O)—$R^{5b}$, —N($R^{5a}$)—C(=O)—NR$^{5b}$R$^{5c}$, —NR$^{5a}$R$^{5b}$, —C(=O)—NR$^{5a}$R$^{5b}$, $R^5$—S—, $R^5$—S(=O)—, $R^5$—S(=O)$_2$—, —N($R^{5a}$)—S(=O)—$R^{5b}$, —S(=O)—NR$^{5a}$R$^{5b}$, —N($R^{5a}$)—S(=O)$_2$—$R^{5b}$, —S(=O)$_2$—NR$^{5a}$R$^{5b}$, —S(=O)(=N$R^{5a}$)$R^{5b}$, —S(=O)(=N$R^{5a}$)$R^{5b}$ or —N=S(=O)($R^{5a}$)$R^{5b}$;

$R^5$ represents a hydrogen atom, a $C_1$-$C_3$-alkyl- group;
$R^{5a}$ represents a hydrogen atom, a $C_1$-$C_3$-alkyl- group;
$R^{5b}$ represents a hydrogen atom, a $C_1$-$C_3$-alkyl- group;
$R^{5c}$ represents a hydrogen atom, a $C_1$-$C_3$-alkyl- group;
p represents an integer of 0 or 1;
q represents an integer of 0 or 1;
or a tautomer, an N-oxide, a hydrate, a solvate, or a salt thereof, or a mixture of same.

In another preferred embodiment, the invention relates to compounds of formula I, supra, in which:

$R^{1a}$ represents a hydrogen atom or a halogen atom or a hydroxy-, cyano-, $C_1$-$C_3$-alkyl-, halo-$C_1$-$C_3$-alkyl-, $C_1$-$C_3$-alkoxy- group;

$R^{1b}$ represents a hydrogen atom or a halogen atom or a cyano group;

$R^{1c}$ represents a hydrogen atom or a halogen atom or a cyano group;

Y represents N or $CR^{2a}$;
Z represents $CR^{2b}$;
one of $R^{2a}$ and $R^{2b}$
represents —(CH$_2$)$_q$—X—(CH$_2$)$_p$—$R^3$; and
the other one of $R^{2a}$ and $R^{2b}$
represents a hydrogen atom or a halogen atom or a group selected from:
$C_1$-$C_6$-alkyl-, halo-$C_1$-$C_3$-alkyl-, cyano-; wherein said $C_1$-$C_6$-alkyl- group is optionally substituted, identically or differently, with 1, 2 or 3 $R^4$ groups;

X represents a single bond or a bivalent group selected from: —O—, —S—, —S(=O)$_2$—, —C(=O)—, —(NR$^{3a}$)—, —C(=O)—O—, —O—C(=O)—, —C(=O)—(NR$^{3a}$)—, —(NR$^{3a}$)—C(=O)—;

$R^3$ represents a hydrogen atom or a group selected from $C_1$-$C_3$-alkyl-, $C_3$-$C_6$-cycloalkyl-, 4- to 6-membered heterocycloalkyl-, halo-$C_1$-$C_3$-alkyl-;
wherein said $C_1$-$C_3$-alkyl-, $C_3$-$C_6$-cycloalkyl- or 4- to 6-membered heterocycloalkyl- group is optionally substituted, identically or differently, with 1 or 2 $R^4$ groups;

$R^{3a}$ represents a hydrogen atom or a group selected from $C_1$-$C_3$-alkyl-, halo-$C_1$-$C_3$-alkyl-;
wherein said $C_1$-$C_3$-alkyl- group is optionally substituted, identically or differently, with 1 or 2 $R^4$ groups;

$R^{3b}$ represents a hydrogen atom or a group selected from $C_1$-$C_3$-alkyl-, halo-$C_1$-$C_3$-alkyl-;
wherein said $C_1$-$C_3$-alkyl- group is optionally substituted, identically or differently, with 1 or 2 $R^4$ groups; or $R^3$ together with $R^{3a}$ or $R^{3b}$ represent a 3- to 10-membered heterocycloalkyl- or a 4- to 10-membered heterocycloalkenyl- group, which is optionally substituted, one or more times, identically or differently, with halo-, hydroxyl-, cyano-;

$R^4$ represents halo-, hydroxy-, cyano-, $C_1$-$C_3$-alkyl-, halo-$C_1$-$C_3$-alkyl-, $C_1$-$C_3$-alkoxy-, halo-$C_1$-$C_3$-alkoxy-, hydroxy-$C_1$-$C_3$-alkyl-, $C_1$-$C_3$-alkoxy-$C_1$-$C_3$-alkyl-, —C(=O)—$R^5$, —C(=O)—O—$R^5$, —O—C(=O)—$R^5$, —NR$^{5a}$R$^{5b}$, —C(=O)—NR$^{5a}$R$^{5b}$, $R^5$—S—, $R^5$—S(=O)—, $R^5$—S(=O)$_2$—, —N(R$^{5a}$)—S(=O)—R$^{5b}$, —S(=O)—NR$^{5a}$R$^{5b}$, —N(R$^{5a}$)—S(=O)$_2$—R$^{5b}$, —S(=O)$_2$—NR$^{5a}$R$^{5b}$, —S(=O)(=NR$^{5a}$)R$^{5b}$, —S(=O)(=NR$^{5a}$)R$^{5b}$ or —N=S(=O)(R$^{5a}$)R$^{5b}$;

$R^5$ represents a hydrogen atom, a $C_1$-$C_3$-alkyl- group;
$R^{5a}$ represents a hydrogen atom, a $C_1$-$C_3$-alkyl- group;
$R^{5b}$ represents a hydrogen atom, a $C_1$-$C_3$-alkyl- group;
p represents an integer of 0 or 1;
q represents an integer of 0 or 1;
or a tautomer, an N-oxide, a hydrate, a solvate, or a salt thereof, or a mixture of same.

In another preferred embodiment, the invention relates to compounds of formula I, supra, in which:
$R^{1a}$ represents a hydrogen or halogen atom or a $C_1$-$C_3$-alkyl-, —NR$^{5a}$R$^{5b}$, halo-$C_1$-$C_3$-alkyl-, $C_1$-$C_3$-alkoxy-, or a halo-$C_1$-$C_3$-alkoxy- group;
$R^{1b}$ represents a hydrogen or halogen atom;
$R^{1c}$ represents a hydrogen or halogen atom;
Y represents N or CR$^{2a}$;
Z represents CR$^{2b}$;
one of $R^{2a}$ and $R^{2b}$
  represents —(CH$_2$)$_q$—X—(CH$_2$)$_p$—R$^3$; and
the other one of $R^{2a}$ and $R^{2b}$
  represents a hydrogen atom or a halogen atom or a group selected from:
    $C_1$-$C_3$-alkyl-, halo-$C_1$-$C_3$-alkyl-, cyano-; wherein said $C_1$-$C_3$-alkyl- group is optionally substituted with 1 $R^4$ groups;
X represents a single bond or a bivalent group selected from: —O—, —C(=O)—, —(NR$^{3a}$)—, —C(=O)—O—, —C(=O)—(NR$^{3a}$)—, —(NR$^{3a}$)—C(=O)—, —(NR$^{3a}$)—C(=O)—(NR$^{3b}$)—, —O—C(=O)—(NR$^{3a}$)—, —(NR$^{3a}$)—C(=O)—O—;
$R^3$ represents a hydrogen atom or a group selected from $C_1$-$C_3$-alkyl-, 4- to 6-membered heterocycloalkyl-; wherein said $C_1$-$C_3$-alkyl- or 4- to 6-membered heterocycloalkyl- group is optionally substituted with one $R^4$ group;
$R^{3a}$ represents a hydrogen atom or a $C_1$-$C_3$-alkyl- group;
$R^{3b}$ represents a hydrogen atom or a $C_1$-$C_3$-alkyl- group; or
$R^3$ together with $R^{3a}$ or $R^{3b}$ represent a 3- to 10-membered heterocycloalkyl- or a 4- to 10-membered heterocycloalkenyl- group, which is optionally substituted, one or more times, identically or differently, with halo-, hydroxyl-, cyano-;
$R^4$ represents halo-, hydroxy-, cyano-, $C_1$-$C_3$-alkyl-, $C_2$-$C_3$-alkenyl-, $C_2$-$C_3$-alkynyl-, halo-$C_1$-$C_3$-alkyl-, $C_1$-$C_3$-alkoxy-, halo-$C_1$-$C_3$-alkoxy-, hydroxy-$C_1$-$C_3$-alkyl-, $C_1$-$C_3$-alkoxy-$C_1$-$C_3$-alkyl-, halo-$C_1$-$C_3$-alkoxy-$C_1$-$C_3$-alkyl-;
$R^5$ represents a hydrogen atom, a $C_1$-$C_3$-alkyl- group;
$R^{5a}$ represents a hydrogen atom, a $C_1$-$C_3$-alkyl- group;
$R^{5b}$ represents a hydrogen atom, a $C_1$-$C_3$-alkyl- group;
p represents an integer of 0 or 1;
q represents an integer of 0 or 1;
or a tautomer, an N-oxide, a hydrate, a solvate, or a salt thereof, or a mixture of same.

In another preferred embodiment, the invention relates to compounds of formula I, supra, in which:
$R^{1a}$ represents a $C_1$-$C_3$-alkoxy- group;
$R^{1b}$ represents a hydrogen atom;
$R^{1c}$ represents a hydrogen atom;
Y represents CR$^{2a}$;
Z represents CR$^{2b}$;
$R^{2a}$ represents a $C_1$-$C_3$-alkyl- group; and
$R^{2b}$ represents a $C_1$-$C_3$-alkyl- group;
or a tautomer, an N-oxide, a hydrate, a solvate, or a salt thereof, or a mixture of same.

In another preferred embodiment, the invention relates to compounds of formula I, supra, in which:
$R^{1a}$ represents a hydrogen atom or a $C_1$-$C_3$-alkoxy- group;
$R^{1b}$ represents a hydrogen atom;
$R^{1c}$ represents a hydrogen atom;
Y represents N or CR$^{2a}$;
Z represents N or CR$^{2b}$;
with the proviso that not more than one of Y and Z represents N;
$R^{2a}$ represents a hydrogen atom or a halogen atom or a group selected from: $C_1$-$C_3$-alkyl-, $C_2$-$C_4$-alkynyl-, —X—R$^3$;
  wherein said $C_1$-$C_3$-alkyl- or $C_2$-$C_4$-alkynyl- group is optionally substituted with 1 $R^4$ group;
$R^{2b}$ represents a hydrogen atom or a halogen atom or a group selected from: $C_1$-$C_3$-alkyl-, cyano-, —X—R$^3$;
  wherein said $C_1$-$C_3$-alkyl- group is optionally substituted with 1 $R^4$ group;
X represents a single bond or a bivalent group selected from: —S(=O)$_2$—, —C(=O)—O—, —C(=O)—(NR$^{3a}$)—;
$R^3$ represents a hydrogen atom or a group selected from $C_1$-$C_3$-alkyl-, aryl-;
  wherein said $C_1$-$C_3$-alkyl- or aryl- group is optionally substituted, identically or differently, with 1, 2 or 3 $R^4$ groups;
$R^{3a}$ represents a hydrogen atom or $C_1$-$C_3$-alkyl- group; or
$R^3$ together with $R^{3a}$ or $R^{3b}$ represent a 3- to 10-membered heterocycloalkyl- group;
$R^4$ represents halo-, hydroxy-, cyano-, $C_1$-$C_3$-alkyl-, halo-$C_1$-$C_3$-alkyl-, $C_1$-$C_3$-alkoxy-, halo-$C_1$-$C_3$-alkoxy-, hydroxy-$C_1$-$C_3$-alkyl-, $C_1$-$C_3$-alkoxy-$C_1$-$C_3$-alkyl-, halo-$C_1$-$C_3$-alkoxy-$C_1$-$C_3$-alkyl-, —C(=O)—R$^5$, —C(=O)—O—R$^5$, —O—C(=O)—R$^5$, —N(R$^{5a}$)—C(=O)—R$^{5b}$, —NR$^{5a}$R$^{5b}$, —C(=O)—NR$^{5a}$R$^{5b}$, $R^5$—S(=O)$_2$—, —N(R$^{5a}$)—S(=O)$_2$—R$^{5b}$, —S(=O)$_2$—NR$^{5a}$R$^{5b}$;
$R^5$ represents a hydrogen atom, a $C_1$-$C_6$-alkyl- or $C_3$-$C_6$-cycloalkyl- group;
$R^{5a}$ represents a hydrogen atom, a $C_1$-$C_6$-alkyl- or $C_3$-$C_6$-cycloalkyl- group;
$R^{5b}$ represents a hydrogen atom, a $C_1$-$C_6$-alkyl- or $C_3$-$C_6$-cycloalkyl- group;
or a tautomer, an N-oxide, a hydrate, a solvate, or a salt thereof, or a mixture of same.

In another preferred embodiment, the invention relates to compounds of formula I, supra, in which:
$R^{1a}$ represents a $C_1$-$C_3$-alkoxy- group;
$R^{1b}$ represents a hydrogen atom;
$R^{1c}$ represents a hydrogen atom;
Y represents N or CR$^{2a}$;
Z represents N or CR$^{2b}$;
with the proviso that not more than one of Y and Z represents N;
$R^{2a}$ represents a hydrogen atom or a halogen atom or a group selected from:
  $C_1$-$C_3$-alkyl-, —X—R$^3$;
$R^{2b}$ represents a hydrogen atom or a halogen atom or a group selected from:
  $C_1$-$C_3$-alkyl-, $C_2$-$C_4$-alkynyl-, cyano-, —X—R$^3$;
  wherein said $C_1$-$C_3$-alkyl- group is optionally substituted with 1 $R^4$ group;
X represents a single bond or a bivalent group selected from:
  —S(=O)$_2$—, —C(=O)—O—, —C(=O)—(NR$^{3a}$)—;

R³ represents a hydrogen atom or a group selected from
  C₁-C₃-alkyl-, aryl-;
  wherein said C₁-C₃-alkyl- or aryl- group is optionally substituted, identically or differently, with 1, 2 or 3 R⁴ groups;
R³ᵃ represents a hydrogen atom or C₁-C₃-alkyl- group; or
R³ together with R³ᵃ or R³ᵇ represent a 3- to 10-membered heterocycloalkyl-group;
R⁴ represents halo-, hydroxy-, cyano-, C₁-C₃-alkyl-, halo-C₁-C₃-alkyl-, C₁-C₃-alkoxy-, halo-C₁-C₃-alkoxy-, hydroxy-C₁-C₃-alkyl-, C₁-C₃-alkoxy-C₁-C₃-alkyl-, halo-C₁-C₃-alkoxy-C₁-C₃-alkyl-;
or a tautomer, an N-oxide, a hydrate, a solvate, or a salt thereof, or a mixture of same.

In another preferred embodiment, the invention relates to compounds of formula I, supra, in which:
R¹ᵃ represents a C₁-C₃-alkoxy- group;
R¹ᵇ represents a hydrogen atom;
R¹ᶜ represents a hydrogen atom;
Y represents N or CR²ᵃ;
Z represents N or CR²ᵇ;
with the proviso that not more than one of Y and Z represents N;
R²ᵃ represents a hydrogen atom or a halogen atom or a group selected from:
  C₁-C₃-alkyl-, —X—R³;
R²ᵇ represents a hydrogen atom or a halogen atom or a group selected from:
  C₁-C₃-alkyl-, C₂-C₄-alkynyl-, cyano-, —X—R³;
  wherein said C₁-C₃-alkyl- group is optionally substituted with 1 R⁴ group;
X represents a single bond or a bivalent group selected from:
  —S(=O)₂—, —C(=O)—O—, —C(=O)—(NR³ᵃ)—;
R³ represents a hydrogen atom or a group selected from
  C₁-C₃-alkyl-, aryl-;
  wherein said aryl- group is optionally substituted, identically or differently, with 1 R⁴ group;
R³ᵃ represents a hydrogen atom or C₁-C₃-alkyl- group; or
R³ together with R³ᵃ or R³ᵇ represent a 3- to 10-membered heterocycloalkyl-group;
R⁴ represents halo-, hydroxy-, C₁-C₃-alkyl-, halo-C₁-C₃-alkyl-, C₁-C₃-alkoxy-, halo-C₁-C₃-alkoxy-;
or a tautomer, an N-oxide, a hydrate, a solvate, or a salt thereof, or a mixture of same.

In another preferred embodiment, the invention relates to compounds of formula I, supra, in which:
R¹ᵃ represents a hydrogen atom or a C₁-C₃-alkoxy- group;
R¹ᵇ represents a hydrogen atom;
R¹ᶜ represents a hydrogen atom;
Y represents N or CR²ᵃ;
Z represents N or CR²ᵇ;
with the proviso that not more than one of Y and Z represents N;
R²ᵃ represents a hydrogen atom or a halogen atom or a group selected from:
  C₁-C₃-alkyl-, —X—R³;
R²ᵇ represents a hydrogen atom or a halogen atom or a group selected from:
  C₁-C₃-alkyl-, C₂-C₄-alkynyl-, cyano-, —X—R³;
  wherein said C₁-C₃-alkyl- group is optionally substituted with 1 R⁴ group;
X represents a bond or a bivalent group selected from:
  —S(=O)₂—, —C(=O)—O—, —C(=O)—(NR³ᵃ)—;
R³ represents a hydrogen atom or a group selected from
  C₁-C₃-alkyl-, aryl-;
  wherein said aryl- group is optionally substituted, identically or differently, with 1 R⁴ group;

R³ᵃ represents a hydrogen atom or C₁-C₃-alkyl- group; or
R³ together with R³ᵃ or R³ᵇ represent a 3- to 10-membered heterocycloalkyl-group;
R⁴ represents halo-, hydroxy-, C₁-C₃-alkyl-, halo-C₁-C₃-alkyl-, C₁-C₃-alkoxy-, halo-C₁-C₃-alkoxy-;
or a tautomer, an N-oxide, a hydrate, a solvate, or a salt thereof, or a mixture of same.

It is to be understood that the present invention relates to any sub-combination within any embodiment or aspect of the present invention of compounds of general formula I, supra.

More particularly still, the present invention covers compounds of general formula I which are disclosed in the Examples section of this text, infra.

In accordance with another aspect, the present invention covers methods of preparing compounds of the present invention, said methods comprising the steps as described in the Experimental Section herein.

In a preferred embodiment, the present invention relates to a method of preparing compounds of general formula I, supra, in which method an intermediate compound of general formula II:

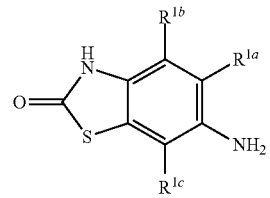

in which R¹ᵃ, R¹ᵇ, and R¹ᶜ are as defined for the compounds of general formula I, supra, is allowed to react with an intermediate compound of general formula IIIb:

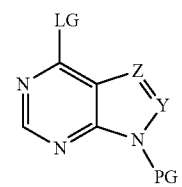

in which Y and Z are as defined for the compounds of general formula I, supra, LG represents a Leaving group, such as a halogen atom or a trifluoromethylsulphonyloxy or nonafluorobutylsulphonyloxy group for example, and PG represents a hydrogen atom or a protective group such as mesyl-, tosyl-, phenylsulfonyl-, tetrahydropyranoyl-, or acyl- group, thus providing a compound of general formula I:

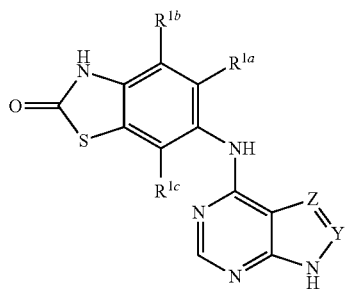

I in which $R^{1a}$, $R^{1b}$, $R^{1c}$, Y and Z are as defined for the compounds of general formula I, supra.

In another aspect, the present invention relates to intermediate compounds for the preparation of the compounds of general formula I, supra.

In a preferred embodiment, the present invention relates to intermediate compounds of formula IIIa, IIIc or IIId:

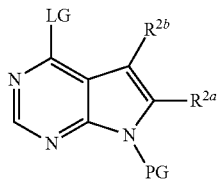

IIIa

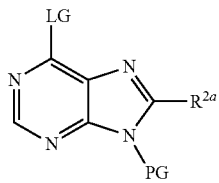

IIIc

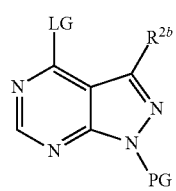

IIId in which $R^{2a}$ and $R^{2b}$ are as defined for the compounds of general formula I, supra, PG represents a hydrogen atom or a protective group and LG represents a Leaving group.

Synthesis of Compounds of General Formula I of the Present Invention

Compounds of general formula II, IIIa, IIIb, IV, V, VI and VII wherein $R^{1a}$, $R^{1b}$, $R^{1c}$, $R^{2a}$, $R^{2b}$, Y and Z have the meaning as given for general formula I, supra, LG represents a Leaving group and PG represents a protective group or a hydrogen atom, can be synthesized according to the procedures depicted in Scheme 1.

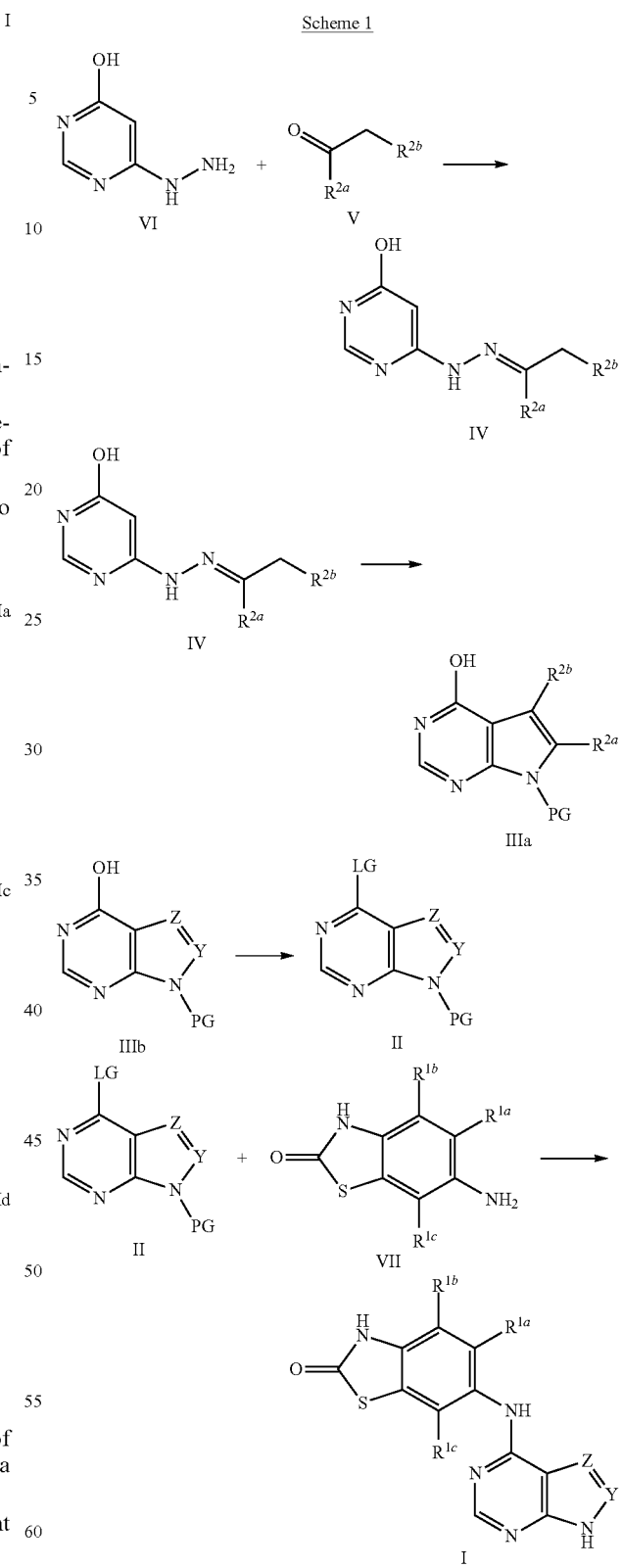

Scheme 1

Scheme 1 exemplifies one route that allows variations and modifications in $R^{2a}$ or $R^{2b}$ at different stages of the synthesis. However, also other routes may be used to synthesise the target compounds, in accordance with common general knowledge of a person skilled in the art of organic synthesis. The order of transformations exemplified in the Scheme is therefore not intended to be limiting. In addition, interconversion of any of the substituents, $R^{1a}, R^{1b}, R^{1c}, R^{2a}, R^{2b}$ can be achieved before and/or after the exemplified transformations.

These modifications can be such as the introduction of protective groups, cleavage of protective groups, reduction or oxidation of functional groups, halogenation, metallation, substitution or other reactions known to a person skilled in the art.

These transformations include those which introduce a functionality which allows for further interconversion of substituents. Appropriate protective groups and their introduction and cleavage are well-known to a person skilled in the art (see for example T. W. Greene and P. G. M. Wuts in Protective Groups in Organic Synthesis, 3$^{rd}$ edition, Wiley 1999). Specific examples are described in the subsequent paragraphs. Further, it is possible that two or more successive steps may be performed without work-up being performed between said steps, e.g. a "one-pot" reaction, as it is well-known to a person skilled in the art. Compounds of formula VI, IIIa, IIIb or II may be commercially available or can be synthesized according to procedures known to a person skilled in the art, for example applying procedures described in the European Journal of Medicinal Chemistry, 2011, 46 (12), 6002-6014, Journal of Medicinal Chemistry, 1996, 39 (12), 2285-2292 or Tetrahedron, 1992, 48 (37), 8089-8100. Compounds of formula V may be commercially available or can be synthesized according to procedures known to a person skilled in the art. Compounds of formula VII may be commercially available or can be synthesized according to procedures known to a person skilled in the art, for example applying procedures described in U.S. Pat. No. 4,370,340. Compounds of formula IV can be synthesized by reacting compound VI with carbonyl compound V in an inert solvent like, for example, ethanol or methanol at temperatures ranging from room temperature to the boiling point of the solvent, for example. Compounds of formula IIIa in which Y represents $CR^{2a}$ and Z represents $CR^{2b}$ can also be synthesized by heating compounds of formula IV with or without an inert additive or solvent like, for example, xylol, 2-[2-(2-tert-butoxyethoxy)ethoxy]-2-methylpropane or 1-methoxy-2-(2-methoxyethoxyl)ethane, at temperatures ranging from 100° C. to 400° C. and pressures ranging from 1 atmosphere to 50 bar. Heating can be optionally performed using microwave irradiation optionally with an additive to improve the absorption of microwave radiation like, for example, an ionic liquid like, for example, 3-(triphenylphosphonio)-propane-1-sulfonate.

Compounds of formula II in which LG represents a Leaving group like, for example, a halogen atom as, for example, a chlorine or bromine atom are obtained from compounds of formula IIIb by reacting the alcohol with a halogenation agent like, for example, phosphorus trichloride or phosphorus tribromide with or without an additional inert solvent as, for example, toluene at temperatures ranging from room temperature to the boiling point of the solvent, for example. Compounds of formula II in which LG represents a Leaving group like, for example, an alkylsulfonate as, for example, methanesulfonate or trifluoromethanesulfonate or 1,1,2,2,3, 3,4,4,4-nonafluorobutane-1-sulfonate or an arylsulfonate like, for example, benzenesulfonate or 4-methylbenzenesulfonate are obtained from compounds of formula IIIb by reacting the alcohol with a suitable alkylsulfonate as, for example, methanesulfonyl chloride or trifluoromethanesulfonyl chloride or 1,1,2,2,3,3,4,4,4-nonafluorobutane-1-sulfonyl fluoride or by reacting the alcohol with a suitable arylsulfonate as, for example, benzenesulfonyl chloride or 4-methylbenzenesulfonyl chloride in an inert solvent like, for example, tetrahydrofuran or toluene or dichloromethane optionally in the presence of a suitable base like, for example, triethylamine or pyridine or N,N-dimethylpyridin-4-amine at temperatures ranging from −40° C. to the boiling point of the solvent, for example. Compounds of formula I can be synthesized by reacting compounds of formula II with a compound of general formula VII with $R^{1a}, R^{1b}, R^{1c}$, as defined for general formula I. The optionally substituted 6-amino-1,3-benzothiazol-2(3H)-one VII replaces LG in compounds of general formula II to form amines of general formula I. Compounds of general formula II can be reacted with amines of formula VII optionally in the presence of an acid like, for example, hydrochloric acid in an inert solvent like, for example, ethanol or 1,4-dioxane at temperatures ranging from room temperature to the boiling point of the solvent, for example, to give compounds of general formula I. Compounds of general formula I can also be built by Ullmann-type coupling reactions in the presence of suitable catalysts, such as, for example, copper based catalysts like copper(II)diacetate or copper(I)chloride in the presence of a suitable base, like for example, caesium carbonate starting from compounds of general formula II. Optionally, suitable ligands like N,N-dimethylglycine or phenyl hydrogen pyrrolidin-2-ylphosphonate can be added. The reaction can be performed at temperatures ranging from −40° C. to the boiling point of the solvent, for example. Compounds of general formula IIIa, IIIb, II or I in which $R^{1a}, R^{1b}, R^{1c}, R^{2a}$ and/or $R^{2b}$ represent a halogen atom such as, for example, a chlorine, bromine or iodine atom, can be further modified via coupling reactions such as, for example Ullmann-, Negishi-, Suzuki- or Sonogashira-type coupling reactions. Said coupling reactions are performed in the presence of suitable catalysts, such as, for example, copper- or palladium based catalysts like, for example, copper(II)diacetate, copper(I)chloride, Palladium (II) acetate, tetrakis(triphenylphosphine)palladium (0), bis (triphenylphosphine)palladium (II) chloride or (1,1,-bis (diphenylphosphino) ferrocene)-dichloropalladium (II) and optionally suitable additives such as, for example, phosphines like, for example, $P(oTol)_3$ or triphenylphosphine and, and optionally with a suitable base, such as, for example, potassium carbonate, sodium 2-methylpropan-2-olate, tetrabutylammonium fluoride or tribasic potassium phosphate in a suitable solvent, such as, for example, tetrahydrofuran. Examples of such coupling reactions may be found in the textbook entitled "Metal-Catalyzed Cross-Coupling Reactions", Armin de Meijere (Editor), François Diederich (Editor) September 2004, Wiley Interscience ISBN: 978-3-527-30518-6.

Compounds of general formula IIIa, IIIb, II or I in which $R^{1a}, R^{1b}, R^{1c}, R^{2a}$ or $R^{2b}$ represents a halogen atom such as a fluorine, chlorine, bromine or iodine atom, can also be further modified via substitution reactions. Said halogen atoms in $R^{1a}, R^{1b}, R^{1c}, R^{2a}$ and/or $R^{2b}$ can be substituted by nucleophiles like primary or secondary amines, alkoxides, thiolates or carbon anion bearing groups to add secondary or tertiary amines, ethers, thioethers or carbon attached groups. The reactions are performed in inert solvents like tetrahydrofuran. Furthermore, residues in compounds of formulas I, II, IIIa, IIIb, IV, V, or VII can be optionally modified using, for example, oxidation-, reduction-, substitution- or elimination-reactions and conditions that are well known to a person skilled in the art of organic synthesis. For example, thioethers can be oxidized using oxidation reagents like 3-chlorobenzenecarboperoxoic acid, oxone or dimethyldioxirane in inert solvents like dichloromethane or acetone, respectively.

Depending on the stoichiometric ratio of oxidation reagent to the aforementioned compounds sulfoxides or sulfones or mixtures thereof will be obtained.

Further, the compounds of formula I of the present invention can be converted to any salt as described herein, by any method which is known to the person skilled in the art. Similarly, any salt of a compound of formula I of the present invention can be converted into the free compound, by any method which is known to the person skilled in the art.

The compounds and intermediates produced according to the methods of the invention may require purification. Purification of organic compounds is well known to the person skilled in the art and there may be several ways of purifying the same compound. In some cases, no purification may be necessary. In some cases, the compounds may be purified by crystallisation. In some cases, impurities may be removed by stirring using a suitable solvent. In some cases, the compounds may be purified by chromatography, particularly flash chromatography, using for example pre-packed silica gel cartridges, e.g. from Separtis such as Isolute® Flash silica gel or Isolute® Flash NH$_2$ silica gel in combination with a suitable chromatographic system such as an Isolera system (Biotage) and eluents such as, for example, gradients of hexane/ethyl acetate or dichloromethane/methanol. In some cases, the compounds may be purified by preparative HPLC using, for example, a Waters autopurifier equipped with a diode array detector and/or on-line electrospray ionisation mass spectrometer in combination with a suitable pre-packed reverse phase column and eluents such as, for example, gradients of water and acetonitrile which may contain additives such as trifluoroacetic acid, formic acid or aqueous ammonia.

EXAMPLES

Chemical naming of the examples and intermediates was performed using ACD software (Name Batch version 12.01.)

Example 1

6-[(6-Ethyl-5-methyl-7H-pyrrolo[2,3-d]pyrimidin-4-yl)amino]-1,3-benzothiazol-2(3H)-one

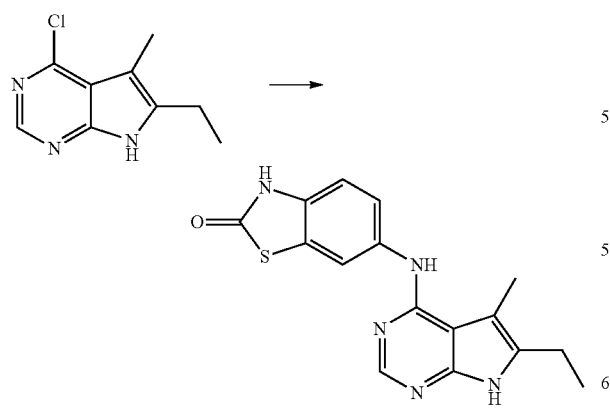

A mixture comprising 60.0 mg (307 μmol) 4-chloro-6-ethyl-5-methyl-7H-pyrrolo[2,3-d]pyrimidine (prepared according to intermediate example 1a), 51 mg 6-amino-1,3-benzothiazol-2(3H)-one (CAS-No: 56354-98-4), 1.75 mL ethanol and 16.9 μL hydrochloric acid (4M in dioxane) was reacted at 110° C. for 10 hours. The residue was digested in a mixture of diethyl ether and ethanol and dried to give 85.3 mg (85%) of the title compound.

$^1$H-NMR (DMSO-d6): δ=1.16 (3H), 2.37 (3H), 2.66 (2H), 7.23 (1H), 7.37 (1H), 7.74 (1H), 8.10 (1H), 9.65 (1H), 12.18 (1H), 12.50 (1H) ppm.

Example 1a

4-Chloro-6-ethyl-5-methyl-7H-pyrrolo[2,3-d]pyrimidine

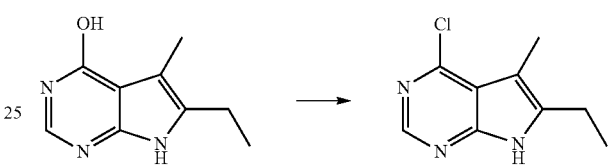

A mixture comprising 1.18 g (6.64 mmol) 6-ethyl-5-methyl-7H-pyrrolo[2,3-d]pyrimidin-4-ol (prepared according to intermediate example 1b) and 37.1 mL phosphorus oxychloride was heated at 100° C. for 1 hour. The reagent was removed and the residue purified by chromatography. The product was further purified by digestion with diethyl ether to give 855 mg (66%) of the title compound.

Example 1b

6-Ethyl-5-methyl-7H-pyrrolo[2,3-d]pyrimidin-4-ol

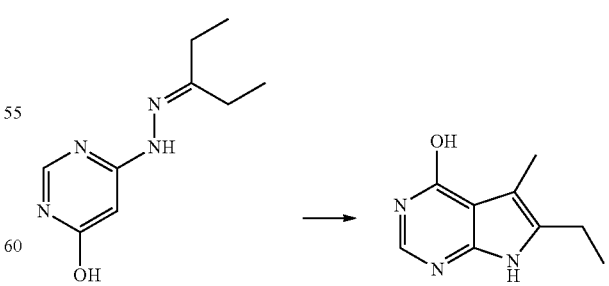

A mixture comprising 735 mg (3.78 mmol) 6-[2-(pentan-3-ylidene)hydrazino]pyrimidin-4-o (prepared according to intermediate example 1c) and 20 mL 2-[2-(2-tert-butoxyethoxy)ethoxy]-2-methylpropane was heated at 250° C. for 2.5 hours. The solid was filtered off and washed with diethyl ether to give 477 mg (68%) of the title compound.

Example 1c

6-[2-(Pentan-3-ylidene)hydrazino]pyrimidin-4-ol

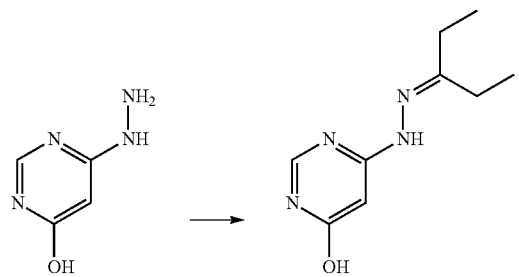

A mixture comprising 5.0 g (39.6 mmol) 6-hydrazinopyrimidin-4-ol/6-hydrazinopyrimidin-4(1H)-one (CAS-No: 29939-37-5), 5.12 g pentan-3-one and 80.8 mL ethanol was heated under reflux for 2 hours. After cooling to 3° C., the precipitated solid was filtered off and washed with diethyl ether to give 5.82 g (72%) of the title compound.

Example 2

6-[(5-Fluoro-7H-pyrrolo[2,3-d]pyrimidin-4-yl)amino]-1,3-benzothiazol-2(3H)-one

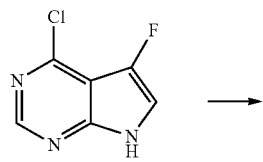

60.0 mg (350 µmol) 4-chloro-5-fluoro-7H-pyrrolo[2,3-d]pyrimidine (CAS-No: 582313-57-3) were transformed in analogy to example 1 to give after working up and purification 86.2 mg (78%) of the title compound.

$^1$H-NMR (DMSO-d6): δ=7.17 (1H), 7.38 (1H), 7.41 (1H), 7.81 (1H), 8.20 (1H), 10.07 (1H), 12.05 (1H), 12.37 (1H) ppm.

Example 3

4-[(2-Oxo-2,3-dihydro-1,3-benzothiazol-6-yl)amino]-7H-pyrrolo[2,3-d]pyrimidine-5-carboxylic acid

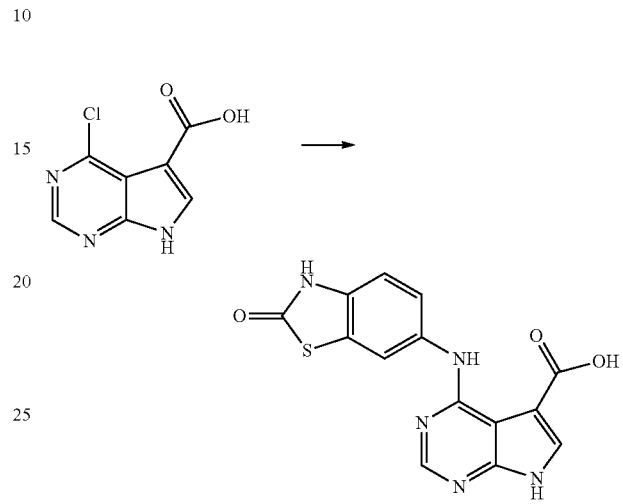

30 mg (152 µmol) 4-chloro-7H-pyrrolo[2,3-d]pyrimidine-5-carboxylic acid (CAS-No: 186519-92-6) were transformed in analogy to example 1 to give after working up and purification 48.2 mg (92%) of the title compound.

$^1$H-NMR (DMSO-d6): δ=7.14 (1H), 7.44 (1H), 8.07 (1H), 8.13 (1H), 8.34 (1H), 11.42 (1H), 11.94 (1H), 12.92 (1H), 12.28-14.33 (1H) ppm.

Example 4

6-({5-[(4-Methylpiperazin-1-yl)carbonyl]-7H-pyrrolo[2,3-d]pyrimidin-4-yl}amino)-1,3-benzothiazol-2(3H)-one

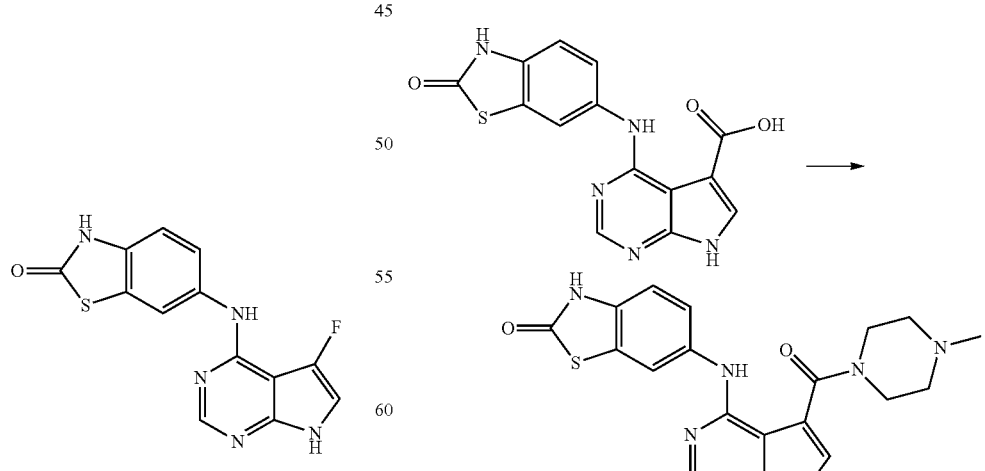

A mixture comprising 18.7 mg (57 µmol) 4-[(2-Oxo-2,3-dihydro-1,3-benzothiazol-6-yl)amino]-7H-pyrrolo[2,3-d]

pyrimidine-5-carboxylic acid (prepared according to example 3), 0.64 mL N,N-dimethylformamide, 57.2 mg 1-methylpiperazine, 136 μL 2,4,6-tripropyl-1,3,5,2,4,6-trioxatriphosphinane 2,4,6-trioxide solution (50% in ethyl acetate) and 29.9 μL N-ethyl-N-isopropylpropan-2-amine was stirred at 23° C. for 2 days. Water was added, the solution was neutralized by addition of sodium hydroxide solution, the solvents were removed and the residue purified by chromatography to give 10.9 mg (44%) of the title compound.

$^1$H-NMR (DMSO-d6): δ=2.18 (3H), 2.36 (4H), 3.77 (4H), 7.07 (1H), 7.39 (1H), 7.72 (1H), 8.16 (1H), 8.31 (1H), 10.74 (1H), 11.74 (1H), 12.41 (1H) ppm.

Example 5

N-Isopropyl-4-[(2-oxo-2,3-dihydro-1,3-benzothiazol-6-yl)amino]-7H-pyrrolo[2,3-d]pyrimidine-5-carboxamide

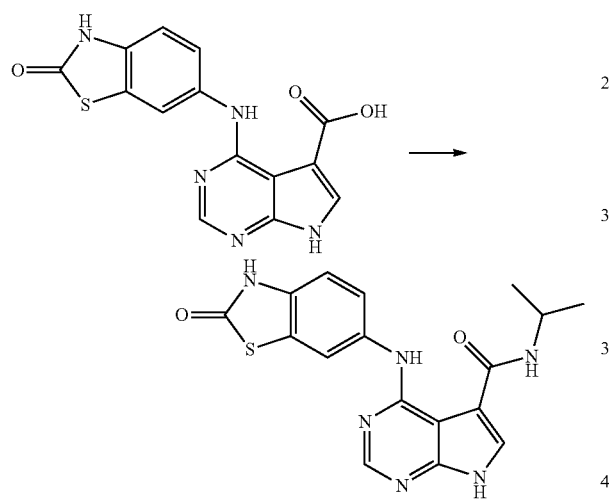

18.7 mg (57 μmol) 4-[(2-Oxo-2,3-dihydro-1,3-benzothiazol-6-yl)amino]-7H-pyrrolo[2,3-d]pyrimidine-5-carboxylic acid (prepared according to example 3) were transformed in analogy to example 4 using propan-2-amine to give after working up and purification 3.2 mg (14%) of the title compound.

$^1$H-NMR (DMSO-d6): δ=1.18 (6H), 4.15 (1H), 7.08 (1H), 7.47 (1H), 8.12 (1H), 8.21-8.31 (3H), 11.72 (1H), 12.28 (1H), 12.32 (1H) ppm.

Example 6

6-(7H-Pyrrolo[2,3-d]pyrimidin-4-ylamino)-1,3-benzothiazol-2(3H)-one

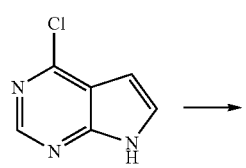

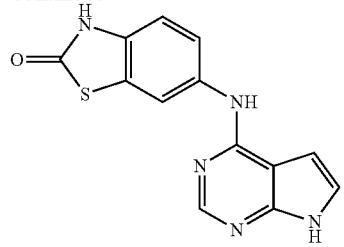

150 mg (977 μmol) 4-chloro-7H-pyrrolo[2,3-d]pyrimidine (CAS-No: 3680-69-1) were transformed in analogy to example 1 to give after working up and purification 221 mg (79%) of the title compound.

$^1$H-NMR (DMSO-d6): δ=6.69 (1H), 7.06 (1H), 7.18 (1H), 7.56 (1H), 8.17, (1H), 8.21 (1H), 9.30 (1H), 11.76 (1H), 11.71 (1H) ppm.

Example 7

6-(1H-pyrazolo[3,4-d]pyrimidin-4-ylamino)-1,3-benzothiazol-2(3H)-one

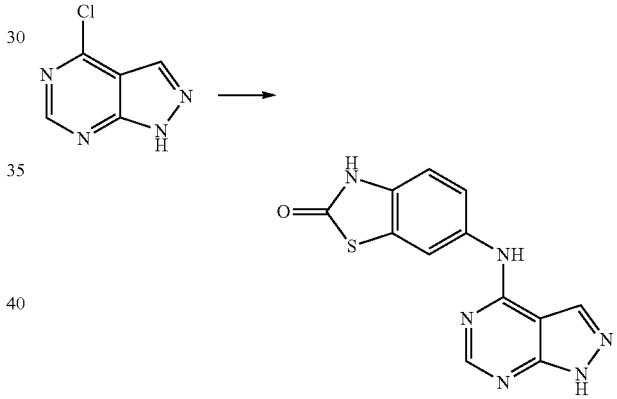

150 mg (971 μmol) 4-chloro-1H-pyrazolo[3,4-d]pyrimidine (CAS-No: 5399-92-8) were transformed in analogy to example 1 to give after working up and purification 69.5 mg (24%) of the title compound.

$^1$H-NMR (DMSO-d6): δ=7.11 (1H), 7.52 (1H), 8.11 (1H), 8.15 (1H), 8.33 (1H), 9.98 (1H), 11.82 (1H), 13.57 (1H) ppm.

Example 8

6-[(6-Bromo-7H-pyrrolo[2,3-d]pyrimidin-4-yl)amino]-1,3-benzothiazol-2(3H)-one

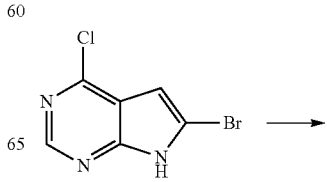

-continued

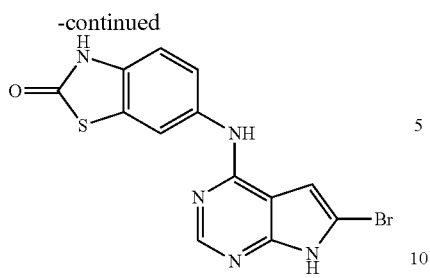

500 mg (2.15 mmol) 6-bromo-4-chloro-7H-pyrrolo[2,3-d]pyrimidine (CAS-No: 784150-41-0) were transformed in analogy to example 1 to give after working up and purification 689 mg (88%) of the title compound.

¹H-NMR (DMSO-d6): δ=6.78 (1H), 7.07 (1H), 7.52 (1H), 8.11 (1H), 8.20 (1H), 9.30 (1H), 11.75 (1H), 12.50 (1H) ppm.

Example 9

6-(9H-Purin-6-ylamino)-1,3-benzothiazol-2(3H)-one

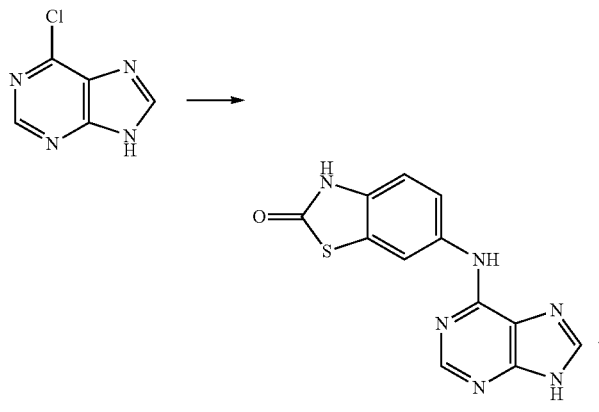

150 mg (971 μmol) 6-chloro-9H-purine (CAS-No: 87-42-3) were transformed in analogy to intermediate example 1 to give after working up and purification 78 mg (28%) of the title compound.

¹H-NMR (DMSO-d6): δ=7.04 (1H), 7.68 (1H), 8.14 (1H), 8.22 (1H), 8.31 (1H), 9.72 (1H), 12.40 (2H) ppm.

Example 10

Ethyl 4-[(2-oxo-2,3-dihydro-1,3-benzothiazol-6-yl)amino]-7H-pyrrolo[2,3-d]pyrimidine-6-carboxylate

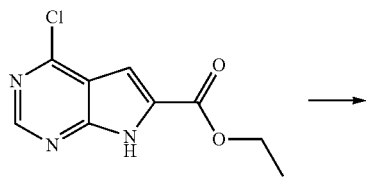

-continued

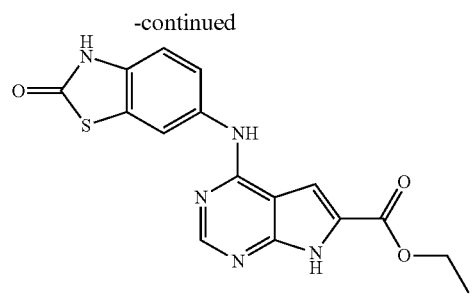

160 mg (μmol) ethyl 4-chloro-7H-pyrrolo[2,3-d]pyrimidine-6-carboxylate (CAS-No: 187725-00-4) were transformed in analogy to example 1 to give after working up and purification 211 mg (68%) of the title compound.

¹H-NMR (DMSO-d6): δ=1.31 (3H), 4.29 (2H), 7.09 (1H), 7.54 (1H), 7.58 (1H), 8.19 (1H), 8.32 (1H), 9.64 (1H), 11.78 (1H), 12.53 (1H) ppm.

Example 11

6-{[6-(3-Hydroxyprop-1-yn-1-yl)-7H-pyrrolo[2,3-d]pyrimidin-4-yl]amino}-1,3-benzothiazol-2(3H)-one

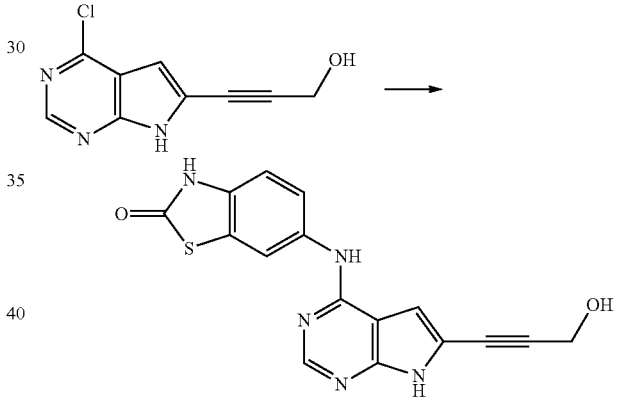

210 mg (1.01 mmol) 3-(4-chloro-7H-pyrrolo[2,3-d]pyrimidin-6-yl)prop-2-yn-1-ol (prepared according to intermediate example 11a) were transformed in analogy to example 1 to give after working up and purification 274 mg (76%) of the title compound.

¹H-NMR (DMSO-d6): δ=4.32 (2H), 5.37 (1H), 6.90 (1H), 7.07 (1H), 7.53 (1H), 8.10 (1H), 8.23 (1H), 9.38 (1H), 11.75 (1H), 12.16 (1H) ppm.

Example 11a 3-(4-Chloro-7H-pyrrolo[2,3-d]pyrimidin-6-yl)prop-2-yn-1-ol

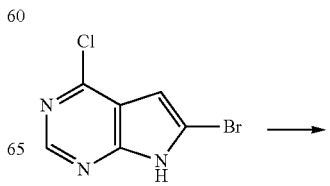

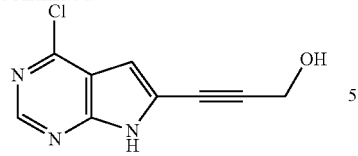

A mixture comprising 3.00 g (12.9 mmol) 6-bromo-4-chloro-7H-pyrrolo[2,3-d]pyrimidine (CAS-No: 784150-41-0), 90 mL tetrahydrofuran, 3.0 mL prop-2-yn-1-ol, 246 mg copper(I) iodide, 746 mg tetrakis(triphenylphosphine)palladium(0) and 3.93 mL N,N-diisopropylethylamine was heated at 80° C. for 4 hours. Water was added and the mixture extracted with ethylacetate/methanol (8:2). The organic layer was washed with brine and dried over sodium sulfate. After filtration and removal of the solvents the residue was purified by chromatography to give 833 mg (31%) of the title compound.

Example 12

4-[(2-Oxo-2,3-dihydro-1,3-benzothiazol-6-yl)amino]-7H-pyrrolo[2,3-d]pyrimidine-5-carbonitrile

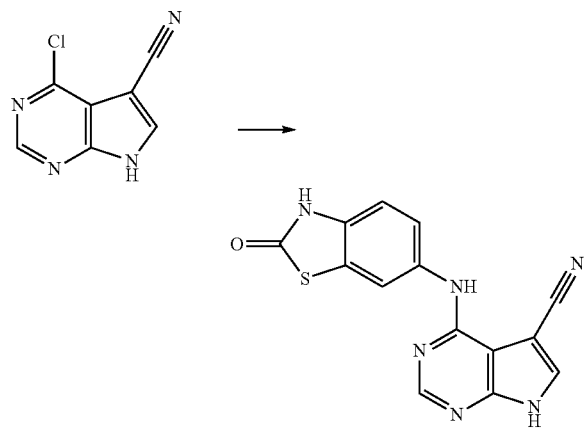

50 mg (280 µmol) 4-chloro-7H-pyrrolo[2,3-d]pyrimidine-5-carbonitrile (CAS-No: 24391-41-1) were transformed in analogy to example 1 to give after working up and purification 38 mg (42%) of the title compound.

$^1$H-NMR (DMSO-d6): δ=7.07 (1H), 7.39 (1H), 7.83 (1H), 8.24 (1H), 8.32 (1H), 8.64 (1H), 12.23 (1H) ppm.

Example 13

6-[(6-Ethyl-5-methyl-7H-pyrrolo[2,3-d]pyrimidin-4-yl)amino]-5-methoxy-1,3-benzothiazol-2(3H)-one

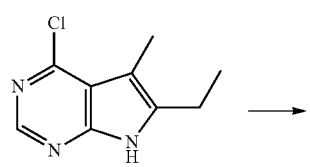

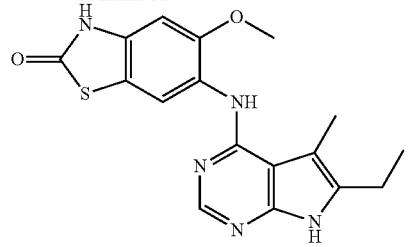

25 mg (128 µmol) 4-Chloro-6-ethyl-5-methyl-7H-pyrrolo[2,3-d]pyrimidine (prepared according to intermediate example 1a) were transformed in analogy to example 1 using 6-amino-5-methoxy-1,3-benzothiazol-2(3H)-one to give after working up and purification 22.3 mg (47%) of the title compound.

$^1$H-NMR (DMSO-d6): δ=1.16 (3H), 2.38 (3H), 2.63 (2H), 3.88 (3H), 6.79 (1H), 7.85 (1H), 8.16 (1H), 8.66 (1H), 11.49 (1H), 11.71 (1H) ppm.

Example 14

6-[(6-Methyl-7H-pyrrolo[2,3-d]pyrimidin-4-yl)amino]-1,3-benzothiazol-2(3H)-one 129 mg (770 µmol) 4-chloro-6-methyl-7H-pyrrolo[2,3-d]pyrimidine (CAS-No: 35808-68-5) were transformed in analogy to example 1 to give after working up and purification 10 mg (4%) of the title compound.

$^1$H-NMR (DMSO-d6): δ=2.32 (3H), 6.35 (1H), 7.05 (1H), 7.55 (1H), 8.14 (2H), 9.10 (1H), 11.53 (1H), 11.71 (1H) ppm.

Example 15

6-[(5-Methyl-7H-pyrrolo[2,3-d]pyrimidin-4-yl)amino]-1,3-benzothiazol-2(3H)-one

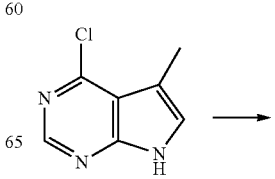

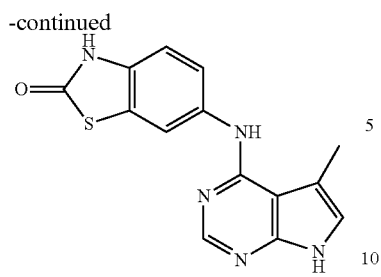

125 mg (746 μmol) 4-chloro-5-methyl-7H-pyrrolo[2,3-d]pyrimidine (CAS-No: 1618-36-6) were transformed in analogy to example 1 to give after working up and purification 20.0 mg (9%) of the title compound.

$^1$H-NMR (DMSO-d6): δ=2.47 (3H), 6.97 (1H), 7.07 (1H), 7.52 (1H), 7.93 (1H), 8.02 (1H), 8.14 (1H), 11.41 (1H), 11.71 (1H) ppm.

Example 16

6-[(6-Chloro-7H-pyrrolo[2,3-d]pyrimidin-4-yl)amino]-1,3-benzothiazol-2(3H)-one

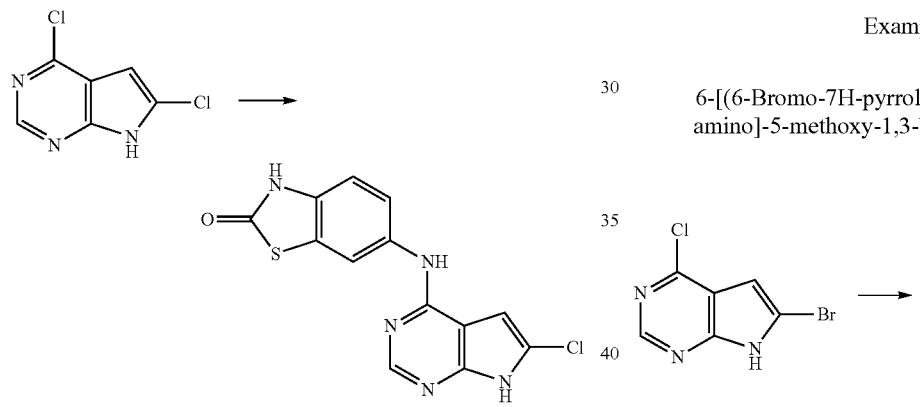

125 mg (665 μmol) 4,6-dichloro-7H-pyrrolo[2,3-d]pyrimidine (CAS-No: 97337-32-1) were transformed in analogy to example 1 to give after working up and purification 15.0 mg (7%) of the title compound.

$^1$H-NMR (DMSO-d6): δ=6.70 (1H), 7.09 (1H), 7.54 (1H), 8.13 (1H), 8.24 (1H), 9.33 (1H), 11.78 (1H), 12.58 (1H) ppm.

Example 17

6-{[6-(3-Hydroxypropyl)-7H-pyrrolo[2,3-d]pyrimidin-4-yl]amino}-1,3-benzothiazol-2(3H)-one

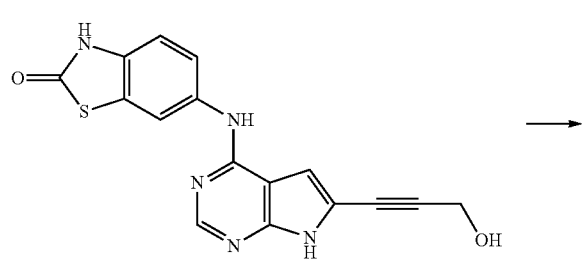

A mixture comprising 262 mg (777 μmol) 6-{[6-(3-hydroxyprop-1-yn-1-yl)-7H-pyrrolo[2,3-d]pyrimidin-4-yl]amino}-1,3-benzothiazol-2(3H)-one (prepared according to example 11), 15 mL ethanol, 5 mL tetrahydrofuran and 41.3 mg palladium on charcoal (10%) were stirred at 23° C. under an atmosphere of hydrogen overnight. After filtration and removal of the solvents the crude product was purified by chromatography and crystallization to give 12 mg (4%) of the title compound.

$^1$H-NMR (DMSO-d6): δ=1.78 (2H), 2.68 (2H), 3.43 (2H), 4.50 (1H), 6.39 (1H), 7.04 (1H), 7.55 (1H), 8.15 (1H), 8.17 (1H), 9.13 (1H), 11.56 (1H), 11.75 (1H) ppm.

Example 18

6-[(6-Bromo-7H-pyrrolo[2,3-d]pyrimidin-4-yl)amino]-5-methoxy-1,3-benzothiazol-2(3H)-one 25 mg (108 μmol) 6-bromo-4-chloro-7H-pyrrolo[2,3-d]pyrimidine (CAS-No: 784150-41-0) were transformed in analogy to example 1 using 6-amino-5-methoxy-1,3-benzothiazol-2(3H)-one to give after working up and purification 11.8 mg (27%) of the title compound.

¹H-NMR (DMSO-d6): δ=3.77 (3H), 6.62 (1H), 6.80 (1H), 7.82 (1H), 8.08 (1H), 8.67 (1H), 11.92 (1H), 12.37 (1H) ppm.

Example 19

5-Methoxy-6-(7H-pyrrolo[2,3-d]pyrimidin-4-ylamino)-1,3-benzothiazol-2(3H)-one

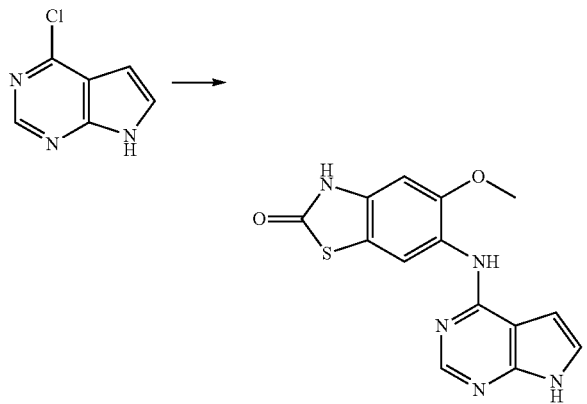

20 mg (130 μmol) 4-chloro-7H-pyrrolo[2,3-d]pyrimidine (CAS-No. 3680-59-1) were transformed in analogy to example 1 using 6-amino-5-methoxy-1,3-benzothiazol-2(3H)-one to give after working up and purification 8.0 mg (19%) of the title compound.

¹H-NMR (DMSO-d6): δ=3.78 (3H), 6.49 (1H), 6.80 (1H), 7.13 (1H), 7.88 (1H), 8.11 (1H), 8.56 (1H), 11.61 (2H) ppm.

Example 20

N,N-dimethyl-4-[(2-oxo-2,3-dihydro-1,3-benzothiazol-6-yl)amino]-7H-pyrrolo[2,3-d]pyrimidine-5-carboxamide

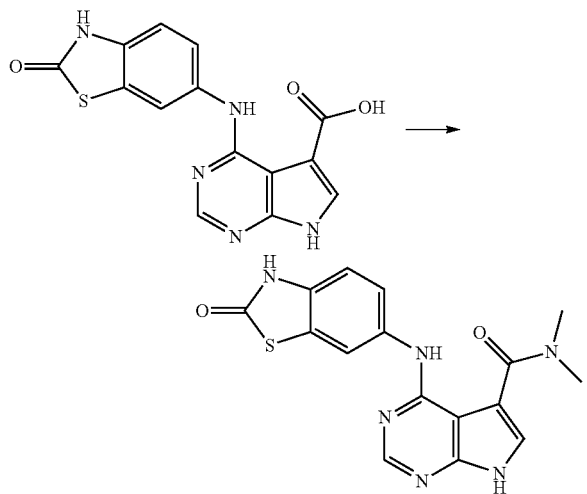

64.6 mg (178 μmol) 4-[(2-oxo-2,3-dihydro-1,3-benzothiazol-6-yl)amino]-7H-pyrrolo[2,3-d]pyrimidine-5-carboxylic acid (prepared according to example 3) were transformed in analogy to example 4 using N-methylmethanamine to give after working up and purification 32.6 mg (49%) of the title compound.

¹H-NMR (DMSO-d6): δ=3.22 (6H), 7.09 (1H), 7.42 (1H), 7.84 (1H), 8.20 (1H), 8.33 (1H), 11.23 (1H), 11.76 (1H), 12.42 (1H) ppm.

Example 21

6-[(6-Isobutyl-5-isopropyl-7H-pyrrolo[2,3-d]pyrimidin-4-yl)amino]-1,3-benzothiazol-2(3H)-one

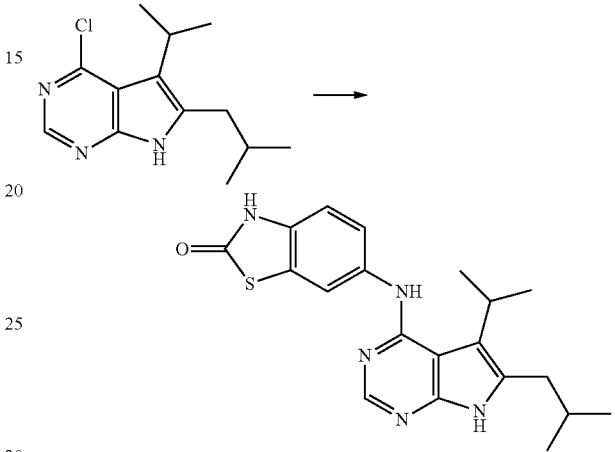

90 mg (357 μmol) 4-chloro-6-isobutyl-5-isopropyl-7H-pyrrolo[2,3-d]pyrimidine (prepared according to intermediate example 21a) were transformed in analogy to example 1 to give after working up and purification 46.1 mg (32%) of the title compound.

¹H-NMR (DMSO-d6): δ=0.89 (6H), 1.35 (6H), 1.99 (1H), 2.58 (2H), 3.47 (1H), 7.07 (1H), 7.48 (1H), 7.52 (1H), 7.92 (1H), 8.11 (1H), 11.41 (1H), 11.80 (1H) ppm.

Example 21a

4-Chloro-6-isobutyl-5-isopropyl-7H-pyrrolo[2,3-d]pyrimidine

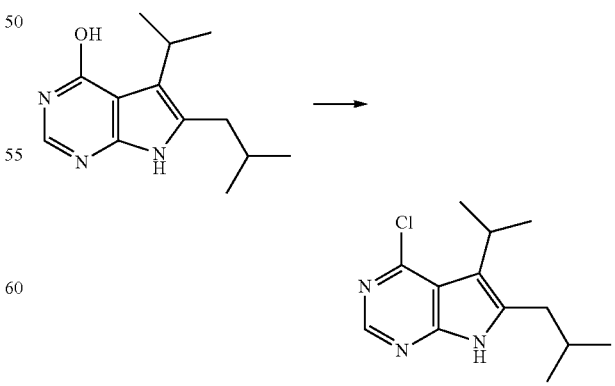

1.25 g (5.35 mmol) 6-isobutyl-5-isopropyl-7H-pyrrolo[2,3-d]pyrimidin-4-ol (prepared according to intermediate example 21b) were transformed in analogy to intermediate example 1a to give after working up and purification 470 mg (28%) of the title compound.

Example 21b

6-Isobutyl-5-isopropyl-7H-pyrrolo[2,3-d]pyrimidin-4-ol

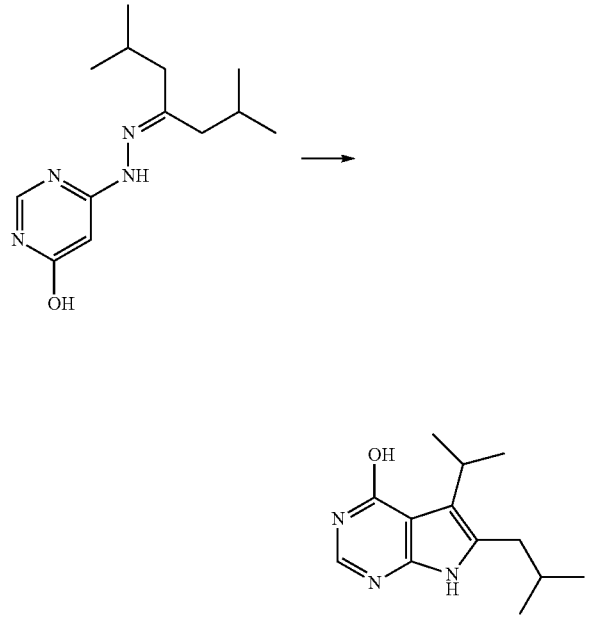

6.00 g (23.97 mmol) 6-[2-(2,6-dimethylheptan-4-ylidene)hydrazino]pyrimidin-4-ol (prepared according to intermediate example 21c) were transformed in analogy to intermediate example 1b to give after working up and purification 1.25 g (22%) of the title compound.

Example 21c

6-[2-(2,6-Dimethylheptan-4-ylidene)hydrazino]pyrimidin-4-ol

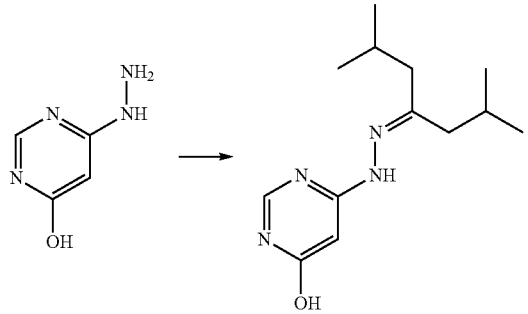 [SMILES: NNc1cc(O)ncn1 ; CC(C)CC(CC(C)C)=NNc1cc(O)ncn1]

10.00 g (79.3 mmol) 6-hydrazinopyrimidin-4-ol (CAS-No: 29939-37-5) were transformed in analogy to intermediate example 1c using 2,6-dimethylheptan-4-one to give after working up and purification 8.77 g (44%) of the title compound.

Example 22

6-[(5-Ethyl-6-propyl-7H-pyrrolo[2,3-d]pyrimidin-4-yl)amino]-1,3-benzothiazol-2(3H)-one

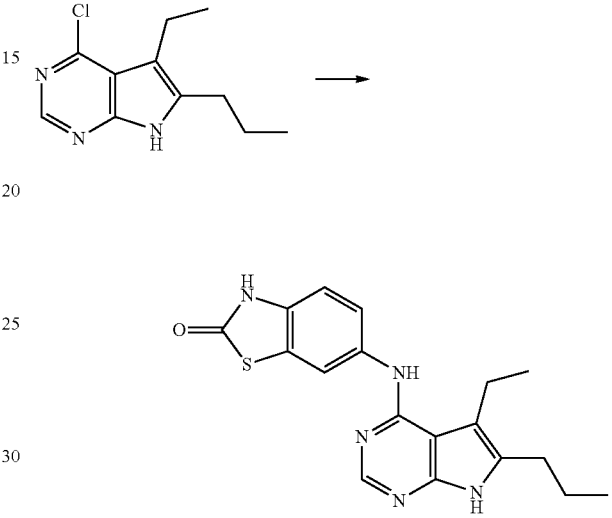

100 mg (447 μmol) 4-chloro-5-ethyl-6-propyl-7H-pyrrolo[2,3-d]pyrimidine (prepared according to intermediate example 22a) were transformed in analogy to example 1 to give after working up and purification 66.5 mg (40%) of the title compound.

$^1$H-NMR (DMSO-d6): δ=0.89 (3H), 1.12 (3H), 1.62 (2H), 2.61 (2H), 2.85 (2H), 7.07 (1H), 7.49 (1H), 7.84 (1H), 7.90 (1H), 8.10 (1H), 11.41 (1H), 11.71 (1H) ppm.

Example 22a

4-Chloro-5-ethyl-6-propyl-7H-pyrrolo[2,3-d]pyrimidine

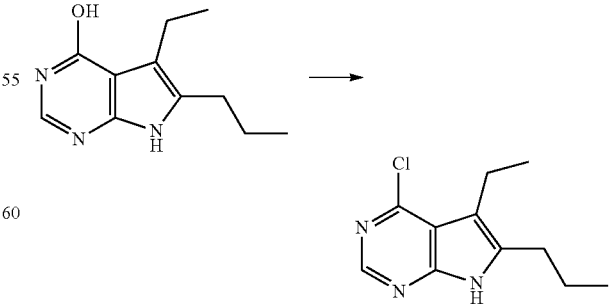

3.24 g (15.79 mmol) 5-ethyl-6-propyl-7H-pyrrolo[2,3-d]pyrimidin-4-ol (prepared according to intermediate example 22b) were transformed in analogy to intermediate example 1a to give after working up and purification 3.62 g (97%) of the title compound.

Example 22b

5-Ethyl-6-propyl-7H-pyrrolo[2,3-d]pyrimidin-4-ol

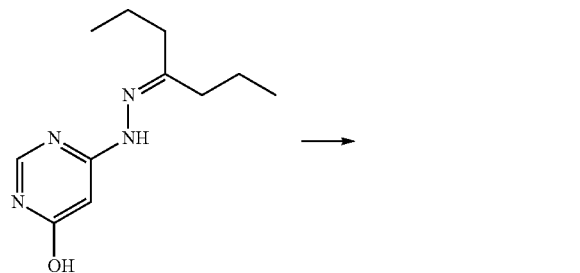

6.00 g (27.99 mmol) 6-[2-(heptan-4-ylidene)hydrazino]pyrimidin-4-ol (prepared according to intermediate example 22c) were transformed in analogy to intermediate example 1b to give after working up and purification 3.24 g (56%) of the title compound.

Example 22c

6-[2-(Heptan-4-ylidene)hydrazino]pyrimidin-4-ol

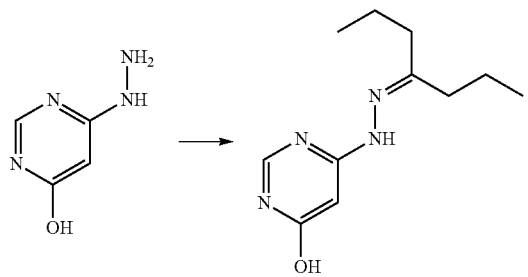 [SMILES: NNc1cc(O)ncn1 ; CCCC(CCC)=NNc1cc(O)ncn1]

10.0 g (79.3 mmol) 6-hydrazinopyrimidin-4-ol (CAS-No: 29939-37-5) were transformed in analogy to intermediate example 1c using heptan-4-one to give after working up and purification 13.5 g (77%) of the title compound.

Example 23

6-({6-[(4-Chlorophenyl)sulfonyl]-7H-pyrrolo[2,3-d]pyrimidin-4-yl}amino)-1,3-benzothiazol-2(3H)-one

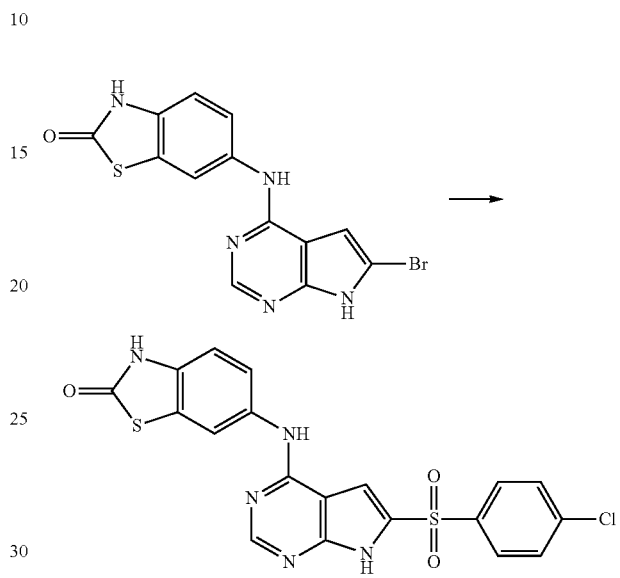

A mixture comprising 50 mg (138 µmol) 6-[(6-bromo-7H-pyrrolo[2,3-d]pyrimidin-4-yl)amino]-1,3-benzothiazol-2(3H)-one (prepared according to example 8), 0.6 mL dimethyl sulfoxide, 109.7 mg sodium 4-chlorobenzenesulfinate, 7.7 mg (mu-benzene-1,2,3,4-tetrayl-1 kappa$^2$C$^1$,C$^2$: 2kappa$^2$C$^3$,C$^4$)[bis(trifluoromethanesulfonatato-kappaO)]dicopper, 2.97 µL N,N-dimethylethane-1,2-diamine was heated at 120° C. for 2 hours to give after chromatography 2.2 mg (3%) of the title compound.

$^1$H-NMR (DMSO-d6): δ=7.11 (1H), 7.56 (1H), 7.62 (1H), 7.74 (2H), 8.01 (2H), 8.16 (1H), 8.36 (1H), 9.79 (1H), 11.81 (1H), 13.16 (1H) ppm.

Example 24

6-({6-[(4-Methylphenyl)sulfonyl]-7H-pyrrolo[2,3-d]pyrimidin-4-yl}amino)-1,3-benzothiazol-2(3H)-one

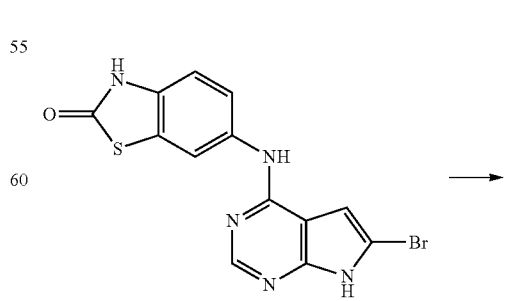

-continued

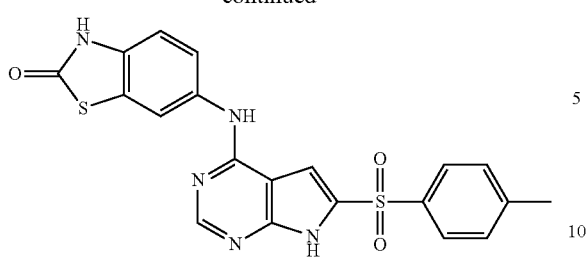

50 mg (138 µmol) 6-[(6-bromo-7H-pyrrolo[2,3-d]pyrimidin-4-yl)amino]-1,3-benzothiazol-2(3H)-one (prepared according to example 8) were transformed in analogy to intermediate example 23 using sodium 4-methylbenzenesulfinate to give after working up and purification 6.7 mg (11%) of the title compound.

$^1$H-NMR (DMSO-d6): δ=2.37 (3H), 7.11 (1H), 7.45 (2H), 7.53-7.60 (2H), 7.90 (2H), 8.17 (1H), 8.35 (1H), 9.75 (1H), 11.80 (1H), 13.08 (1H) ppm.

Example 25

Ethyl 4-[(5-methoxy-2-oxo-2,3-dihydro-1,3-benzothiazol-6-yl)amino]-7H-pyrrolo[2,3-d]pyrimidine-6-carboxylate

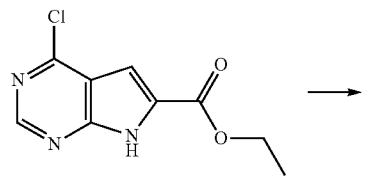

75 mg (332 µmol) ethyl 4-chloro-7H-pyrrolo[2,3-d]pyrimidine-6-carboxylate (CAS-No: 187725-00-4) were transformed in analogy to example 1 using 6-amino-5-methoxy-1,3-benzothiazol-2(3H)-one to give after working up and purification 20.0 mg (15%) of the title compound.

$^1$H-NMR (DMSO-d6): δ=1.31 (3H), 3.78 (3H), 4.30 (2H), 6.81 (1H), 7.38 (1H), 7.82 (1H), 8.19 (1H), 9.08 (1H), 12.44 (1H), 11.82 (1H) ppm.

Example 26

4-[(5-Methoxy-2-oxo-2,3-dihydro-1,3-benzothiazol-6-yl)amino]-7H-pyrrolo[2,3-d]pyrimidine-6-carboxylic acid

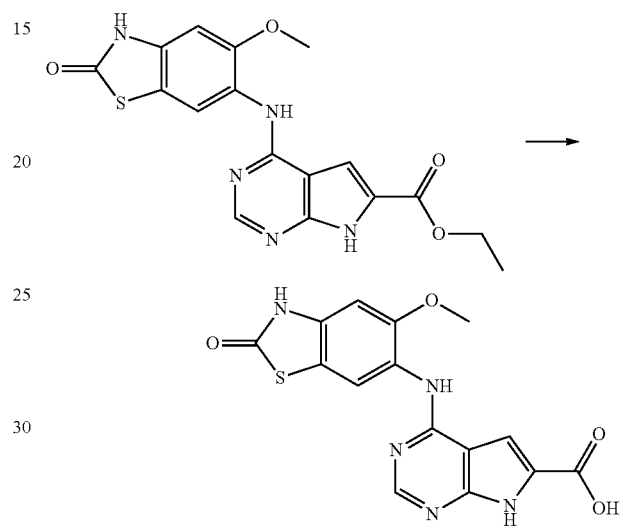

A mixture of 15 mg (39 µmol) ethyl 4-[(5-methoxy-2-oxo-2,3-dihydro-1,3-benzothiazol-6-yl)amino]-7H-pyrrolo[2,3-d]pyrimidine-6-carboxylate (prepared according to example 25), 234 µL aqueous lithium hydroxide (1 molar), and 1.0 mL tetrahydrofuran was stirred at room temperature overnight. The mixture was then acidified by addition of aqueous hydrochloric acid (4 N). The precipitate was filtered, washed with water and diethyl ether and dried to give 10.1 mg (69%) of the title compound.

$^1$H-NMR (DMSO-d6): δ=3.79 (3H), 6.93 (1H), 7.52 (1H), 7.72 (1H), 8.27 (1H), 11.04 (1H), 12.11 (1H), 13.29 (1H) ppm.

Example 27

6-[(5-Bromo-7H-pyrrolo[2,3-d]pyrimidin-4-yl)amino]-1,3-benzothiazol-2(3H)-one

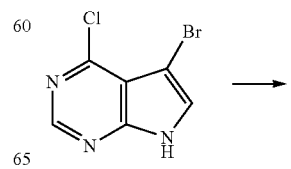

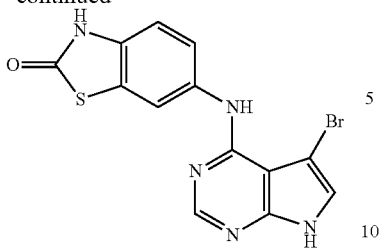
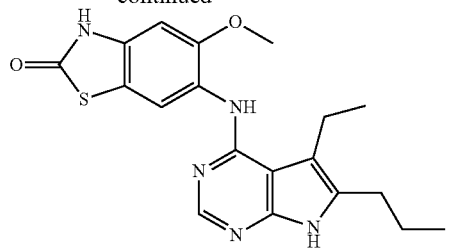

50 mg (215 μmol) 5-bromo-4-chloro-7H-pyrrolo[2,3-d]pyrimidine (CAS-No: 22276-95-5) were transformed in analogy to example 1 to give after working up and purification 65 mg (79%) of the title compound.

$^1$H-NMR (DMSO-d6): δ=7.10 (1H), 7.50 (1H), 7.54 (1H), 8.03 (1H), 8.15 (1H), 8.25 (1H), 11.74 (1H), 12.22 (1H) ppm.

Example 28

6-[(5-Fluoro-7H-pyrrolo[2,3-d]pyrimidin-4-yl)amino]-5-methoxy-1,3-benzothiazol-2(3H)-one

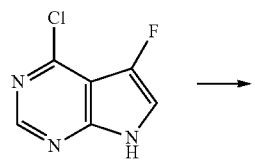

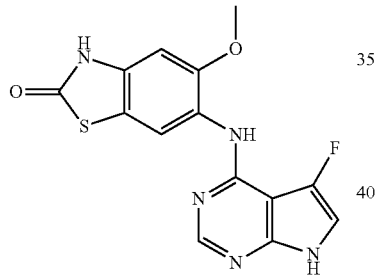

50 mg (291 μmol) 4-chloro-5-fluoro-7H-pyrrolo[2,3-d]pyrimidine (CAS-No: 582313-57-3) were transformed in analogy to example 1 using 6-amino-5-methoxy-1,3-benzothiazol-2(3H)-one to give after working up and purification 2.9 mg (3%) of the title compound.

$^1$H-NMR (DMSO-d6): δ=3.87 (3H), 6.81 (1H), 7.22 (1H), 7.95 (1H), 8.25 (1H), 8.45 (1H), 11.66 (1H), 11.76 (1H) ppm.

Example 29

6-[(5-Ethyl-6-propyl-7H-pyrrolo[2,3-d]pyrimidin-4-yl)amino]-5-methoxy-1,3-benzothiazol-2(3H)-one

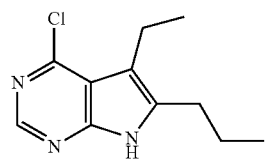

100 mg (447 μmol) 4-chloro-5-ethyl-6-propyl-7H-pyrrolo[2,3-d]pyrimidine (prepared according to intermediate example 22a) were transformed in analogy to example 1 using 6-amino-5-methoxy-1,3-benzothiazol-2(3H)-one to give after working up and purification 3.2 mg (2%) of the title compound.

$^1$H-NMR (DMSO-d6): δ=0.89 (3H), 1.24 (3H), 1.63 (2H), 2.62 (2H), 2.78 (2H), 3.91 (3H), 6.81 (1H), 7.68 (1H), 8.20 (1H), 8.72 (1H), 11.46 (1H) ppm.

Example 30

4-[(2-Oxo-2,3-dihydro-1,3-benzothiazol-6-yl)amino]-7H-pyrrolo[2,3-d]pyrimidine-6-carboxylic acid

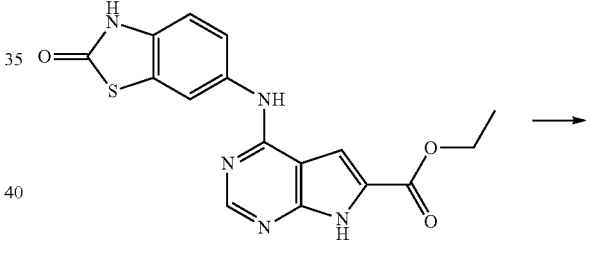

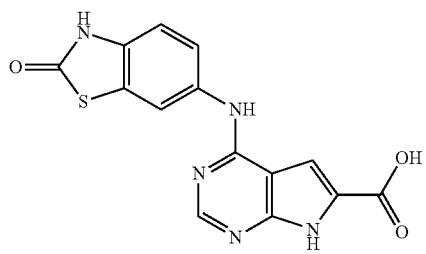

1.60 g (4.50 mmol) ethyl 4-[(2-oxo-2,3-dihydro-1,3-benzothiazol-6-yl)amino]-7H-pyrrolo[2,3-d]pyrimidine-6-carboxylate (prepared according to example 10) were transformed in analogy to example 26 to give after working up and purification 1.39 g (90%) of the title compound.

¹H-NMR (DMSO-d6): δ=7.12 (1H), 7.48 (1H), 7.61 (1H), 8.20 (1H), 8.33 (1H), 9.66 (1H), 11.83 (1H), 12.43 (1H), 12.86-13.19 (1H) ppm.

Example 31

6-[(6-{[4-(Dimethylamino)piperidin-1-yl]carbonyl}-7H-pyrrolo[2,3-d]pyrimidin-4-yl)amino]-1,3-benzothiazol-2(3H)-one

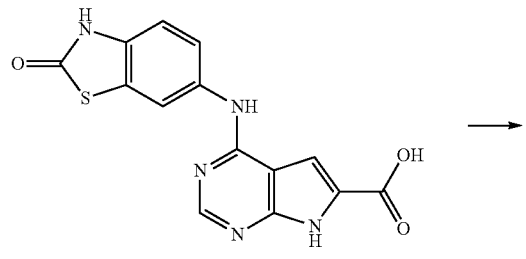

150 mg (458 µmol) 4-[(2-oxo-2,3-dihydro-1,3-benzothiazol-6-yl)amino]-7H-pyrrolo[2,3-d]pyrimidine-6-carboxylic acid (prepared according to example 30) were transformed in analogy to example 4 using N,N-dimethylpiperidin-4-amine to give after working up and purification 10 mg (5%) of the title compound.

¹H-NMR (DMSO-d6): δ=1.29-1.46 (2H), 1.79-1.90 (2H), 2.20 (6H), 2.35-2.46 (1H), 2.90-3.14 (2H), 4.27-4.44 (2H), 6.97-7.05 (1H), 7.11 (1H), 7.50-7.62 (1H), 8.14 (1H), 8.29 (1H), 9.49 (1H), 12.02-12.35 (1H) ppm.

Example 32

6-{[6-(Morpholin-4-ylcarbonyl)-7H-pyrrolo[2,3-d]pyrimidin-4-yl]amino}-1,3-benzothiazol-2(3H)-one

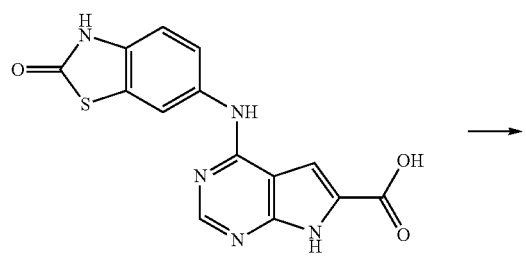

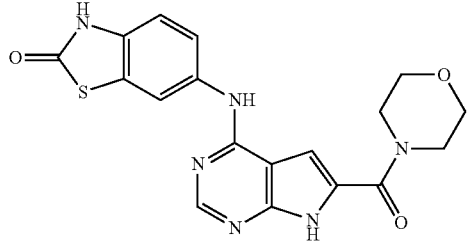

150 mg (458 µmol) 4-[(2-oxo-2,3-dihydro-1,3-benzothiazol-6-yl)amino]-7H-pyrrolo[2,3-d]pyrimidine-6-carboxylic acid (prepared according to example 30) were transformed in analogy to example 4 using morpholine to give after working up and purification 25.0 mg (12%) of the title compound.

¹H-NMR (DMSO-d6): δ=3.61-3.77 (8H), 7.09 (1H), 7.12 (1H), 7.54-7.60 (1H), 8.18 (1H), 8.31 (1H), 9.55 (1H), 12.19-12.32 (1H) ppm.

Example 33

6-{[5-Bromo-6-(piperidin-1-ylcarbonyl)-7H-pyrrolo[2,3-d]pyrimidin-4-yl]amino}-1,3-benzothiazol-2(3H)-one

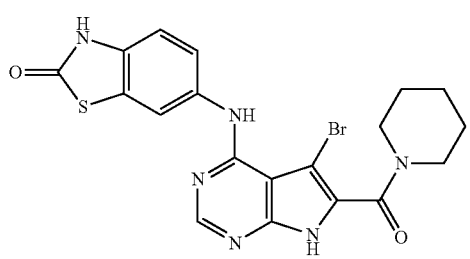

10 mg (24.6 µmol) 4-[(2-oxo-2,3-dihydro-1,3-benzothiazol-6-yl)amino]-7H-pyrrolo[2,3-d]pyrimidine-6-carboxylic acid (prepared according to example 30) were transformed in analogy to example 4 using piperidine to give after working up and purification 10.2 mg (79%) of the title compound.

¹H-NMR (DMSO-d6): δ=1.39-1.74 (6H), 3.21-3.76 (4H), 7.05-7.19 (1H), 7.48-7.62 (1H), 8.01 (1H), 8.21-8.33 (2H), 11.44-12.05 (1H), 12.49-12.86 (1H) ppm.

Example 34

6-[(6-{[(2R)-2-Methylmorpholin-4-yl]carbonyl}-7H-pyrrolo[2,3-d]pyrimidin-4-yl)amino]-1,3-benzothiazol-2(3H)-one

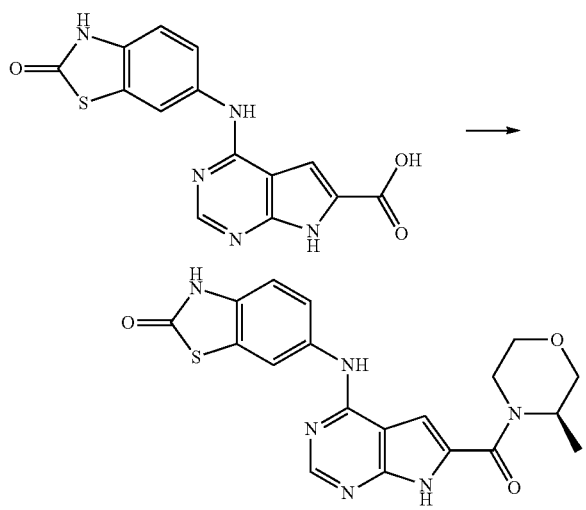

150 mg (458 μmol) 4-[(2-oxo-2,3-dihydro-1,3-benzothiazol-6-yl)amino]-7H-pyrrolo[2,3-d]pyrimidine-6-carboxylic acid (prepared according to example 30) were transformed in analogy to example 4 using (3R)-3-methylmorpholine to give after working up and purification 20.5 mg (10%) of the title compound.

¹H-NMR (DMSO-d6): δ=1.34 (3H), 3.30-3.71 (4H), 3.85-3.94 (1H), 4.03-4.13 (1H), 4.43-4.52 (1H), 7.03-7.07 (1H), 7.12 (1H), 7.52-7.60 (1H), 8.17 (1H), 8.30 (1H), 9.48-9.57 (1H), 11.76-11.87 (1H), 12.15-12.29 (1H). ppm.

Example 35

6-[(6-{[(2S)-2-Methylmorpholin-4-yl]carbonyl}-7H-pyrrolo[2,3-d]pyrimidin-4-yl)amino]-1,3-benzothiazol-2(3H)-one

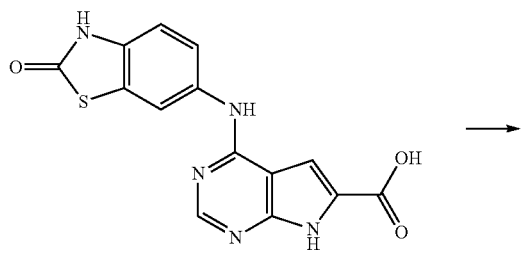

-continued

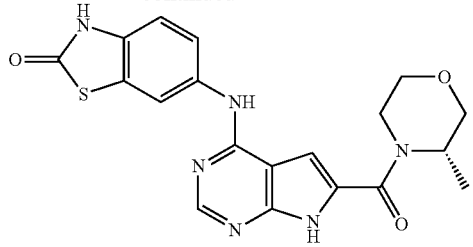

150 mg (458 μmol) 4-[(2-oxo-2,3-dihydro-1,3-benzothiazol-6-yl)amino]-7H-pyrrolo[2,3-d]pyrimidine-6-carboxylic acid (prepared according to example 30) were transformed in analogy to example 4 using (3S)-3-methylmorpholine to give after working up and purification 10.2 mg (5%) of the title compound.

¹H-NMR (DMSO-d6): δ=1.34 (3H), 3.20-3.47 (2H), 3.55-3.62 (1H), 3.66-3.72 (1H), 3.87-3.93 (1H), 4.03-4.15 (1H), 4.42-4.54 (1H), 7.03-7.07 (1H), 7.10-7.14 (1H), 7.54-7.59 (1H), 8.16-8.18 (1H), 8.30 (1H), 9.50-9.54 (1H), 12.01-12.36 (1H) ppm.

Example 36

6-{[6-(Piperidin-1-ylcarbonyl)-7H-pyrrolo[2,3-d]pyrimidin-4-yl]amino}-1,3-benzothiazol-2(3H)-one

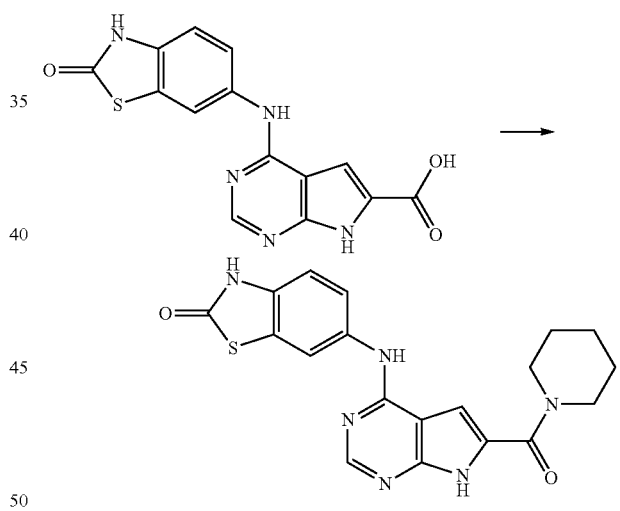

150 mg (458 μmol) 4-[(2-oxo-2,3-dihydro-1,3-benzothiazol-6-yl)amino]-7H-pyrrolo[2,3-d]pyrimidine-6-carboxylic acid (prepared according to example 30) were transformed in analogy to example 4 using piperidine to give after working up and purification 47.0 mg (26%) of the title compound.

¹H-NMR (DMSO-d6): δ=1.50-1.75 (6H), 3.67 (4H), 7.02 (1H), 7.12 (1H), 7.57 (1H), 8.17 (1H), 8.29 (1H), 9.50 (1H), 11.63-11.83 (1H), 12.16 (1H) ppm.

Further, the compounds of formula I of the present invention can be converted to any salt as described herein, by any method which is known to the person skilled in the art. Similarly, any salt of a compound of formula I of the present invention can be converted into the free compound, by any method which is known to the person skilled in the art.

Pharmaceutical Compositions of the Compounds of the Invention

This invention also relates to pharmaceutical compositions containing one or more compounds of the present invention. These compositions can be utilised to achieve the desired pharmacological effect by administration to a patient in need thereof. A patient, for the purpose of this invention, is a mammal, including a human, in need of treatment for the particular condition or disease. Therefore, the present invention includes pharmaceutical compositions that are comprised of a pharmaceutically acceptable carrier and a pharmaceutically effective amount of a compound, or salt thereof, of the present invention. A pharmaceutically acceptable carrier is preferably a carrier that is relatively non-toxic and innocuous to a patient at concentrations consistent with effective activity of the active ingredient so that any side effects ascribable to the carrier do not vitiate the beneficial effects of the active ingredient. A pharmaceutically effective amount of compound is preferably that amount which produces a result or exerts an influence on the particular condition being treated. The compounds of the present invention can be administered with pharmaceutically-acceptable carriers well known in the art using any effective conventional dosage unit forms, including immediate, slow and timed release preparations, orally, parenterally, topically, nasally, ophthalmically, optically, sublingually, rectally, vaginally, and the like.

For oral administration, the compounds can be formulated into solid or liquid preparations such as capsules, pills, tablets, troches, lozenges, melts, powders, solutions, suspensions, or emulsions, and may be prepared according to methods known to the art for the manufacture of pharmaceutical compositions. The solid unit dosage forms can be a capsule that can be of the ordinary hard- or soft-shelled gelatine type containing, for example, surfactants, lubricants, and inert fillers such as lactose, sucrose, calcium phosphate, and corn starch.

In another embodiment, the compounds of this invention may be tableted with conventional tablet bases such as lactose, sucrose and cornstarch in combination with binders such as acacia, corn starch or gelatine, disintegrating agents intended to assist the break-up and dissolution of the tablet following administration such as potato starch, alginic acid, corn starch, and guar gum, gum tragacanth, acacia, lubricants intended to improve the flow of tablet granulation and to prevent the adhesion of tablet material to the surfaces of the tablet dies and punches, for example talc, stearic acid, or magnesium, calcium or zinc stearate, dyes, colouring agents, and flavouring agents such as peppermint, oil of wintergreen, or cherry flavouring, intended to enhance the aesthetic qualities of the tablets and make them more acceptable to the patient. Suitable excipients for use in oral liquid dosage forms include dicalcium phosphate and diluents such as water and alcohols, for example, ethanol, benzyl alcohol, and polyethylene alcohols, either with or without the addition of a pharmaceutically acceptable surfactant, suspending agent or emulsifying agent. Various other materials may be present as coatings or to otherwise modify the physical form of the dosage unit. For instance tablets, pills or capsules may be coated with shellac, sugar or both.

Dispersible powders and granules are suitable for the preparation of an aqueous suspension. They provide the active ingredient in admixture with a dispersing or wetting agent, a suspending agent and one or more preservatives. Suitable dispersing or wetting agents and suspending agents are exemplified by those already mentioned above. Additional excipients, for example those sweetening, flavouring and colouring agents described above, may also be present.

The pharmaceutical compositions of this invention may also be in the form of oil-in-water emulsions. The oily phase may be a vegetable oil such as liquid paraffin or a mixture of vegetable oils. Suitable emulsifying agents may be (1) naturally occurring gums such as gum acacia and gum tragacanth, (2) naturally occurring phosphatides such as soy bean and lecithin, (3) esters or partial esters derived form fatty acids and hexitol anhydrides, for example, sorbitan monooleate, (4) condensation products of said partial esters with ethylene oxide, for example, polyoxyethylene sorbitan monooleate. The emulsions may also contain sweetening and flavouring agents.

Oily suspensions may be formulated by suspending the active ingredient in a vegetable oil such as, for example, arachis oil, olive oil, sesame oil or coconut oil, or in a mineral oil such as liquid paraffin. The oily suspensions may contain a thickening agent such as, for example, beeswax, hard paraffin, or cetyl alcohol. The suspensions may also contain one or more preservatives, for example, ethyl or n-propyl p-hydroxybenzoate; one or more colouring agents; one or more flavouring agents; and one or more sweetening agents such as sucrose or saccharin.

Syrups and elixirs may be formulated with sweetening agents such as, for example, glycerol, propylene glycol, sorbitol or sucrose. Such formulations may also contain a demulcent, and preservative, such as methyl and propyl parabens and flavouring and colouring agents.

The compounds of this invention may also be administered parenterally, that is, subcutaneously, intravenously, intraocularly, intrasynovially, intramuscularly, or interperitoneally, as injectable dosages of the compound in preferably a physiologically acceptable diluent with a pharmaceutical carrier which can be a sterile liquid or mixture of liquids such as water, saline, aqueous dextrose and related sugar solutions, an alcohol such as ethanol, isopropanol, or hexadecyl alcohol, glycols such as propylene glycol or polyethylene glycol, glycerol ketals such as 2,2-dimethyl-1,1-dioxolane-4-methanol, ethers such as poly(ethylene glycol) 400, an oil, a fatty acid, a fatty acid ester or, a fatty acid glyceride, or an acetylated fatty acid glyceride, with or without the addition of a pharmaceutically acceptable surfactant such as a soap or a detergent, suspending agent such as pectin, carbomers, methylcellulose, hydroxypropylmethylcellulose, or carboxymethylcellulose, or emulsifying agent and other pharmaceutical adjuvants. Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum and mineral oil. Suitable fatty acids include oleic acid, stearic acid, isostearic acid and myristic acid. Suitable fatty acid esters are, for example, ethyl oleate and isopropyl myristate. Suitable soaps include fatty acid alkali metal, ammonium, and triethanolamine salts and suitable detergents include cationic detergents, for example dimethyl dialkyl ammonium halides, alkyl pyridinium halides, and alkylamine acetates; anionic detergents, for example, alkyl, aryl, and olefin sulfonates, alkyl, olefin, ether, and monoglyceride sulfates, and sulfosuccinates; non-ionic detergents, for example, fatty amine oxides, fatty acid alkanolamides, and poly(oxyethylene-oxypropylene)s or ethylene oxide or propylene oxide copolymers; and amphoteric detergents, for example, alkyl-beta-aminopropionates, and 2-alkylimidazoline quarternary ammonium salts, as well as mixtures.

The parenteral compositions of this invention will typically contain from about 0.5% to about 25% by weight of the active ingredient in solution. Preservatives and buffers may also be used advantageously. In order to minimise or eliminate irritation at the site of injection, such compositions may contain a non-ionic surfactant having a hydrophile-lipophile balance (HLB) preferably of from about 12 to about 17. The quantity of surfactant in such formulation preferably ranges from about 5% to about 15% by weight. The surfactant can be a single component having the above HLB or can be a mixture of two or more components having the desired HLB.

Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

The pharmaceutical compositions may be in the form of sterile injectable aqueous suspensions. Such suspensions may be formulated according to known methods using suitable dispersing or wetting agents and suspending agents such as, for example, sodium carboxymethylcellulose, methylcellulose, hydroxypropylmethyl-cellulose, sodium alginate, polyvinylpyrrolidone, gum tragacanth and gum acacia; dispersing or wetting agents which may be a naturally occurring phosphatide such as lecithin, a condensation product of an alkylene oxide with a fatty acid, for example, polyoxyethylene stearate, a condensation product of ethylene oxide with a long chain aliphatic alcohol, for example, heptadeca-ethyleneoxycetanol, a condensation product of ethylene oxide with a partial ester derived form a fatty acid and a hexitol such as polyoxyethylene sorbitol monooleate, or a condensation product of an ethylene oxide with a partial ester derived from a fatty acid and a hexitol anhydride, for example polyoxyethylene sorbitan monooleate.

The sterile injectable preparation may also be a sterile injectable solution or suspension in a non-toxic parenterally acceptable diluent or solvent. Diluents and solvents that may be employed are, for example, water, Ringer's solution, isotonic sodium chloride solutions and isotonic glucose solutions. In addition, sterile fixed oils are conventionally employed as solvents or suspending media. For this purpose, any bland, fixed oil may be employed including synthetic mono- or diglycerides. In addition, fatty acids such as oleic acid can be used in the preparation of injectables.

A composition of the invention may also be administered in the form of suppositories for rectal administration of the drug. These compositions can be prepared by mixing the drug with a suitable non-irritation excipient which is solid at ordinary temperatures but liquid at the rectal temperature and will therefore melt in the rectum to release the drug. Such materials are, for example, cocoa butter and polyethylene glycol.

Another formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art (see, e.g., U.S. Pat. No. 5,023,252, issued Jun. 11, 1991, incorporated herein by reference). Such patches may be constructed for continuous, pulsatile, or on demand delivery of pharmaceutical agents.

Controlled release formulations for parenteral administration include liposomal, polymeric microsphere and polymeric gel formulations that are known in the art.

It may be desirable or necessary to introduce the pharmaceutical composition to the patient via a mechanical delivery device. The construction and use of mechanical delivery devices for the delivery of pharmaceutical agents is well known in the art. Direct techniques for, for example, administering a drug directly to the brain usually involve placement of a drug delivery catheter into the patient's ventricular system to bypass the blood-brain barrier. One such implantable delivery system, used for the transport of agents to specific anatomical regions of the body, is described in U.S. Pat. No. 5,011,472, issued Apr. 30, 1991.

The compositions of the invention can also contain other conventional pharmaceutically acceptable compounding ingredients, generally referred to as carriers or diluents, as necessary or desired. Conventional procedures for preparing such compositions in appropriate dosage forms can be utilized. Such ingredients and procedures include those described in the following references, each of which is incorporated herein by reference: Powell, M. F. et al., "Compendium of Excipients for Parenteral Formulations" PDA Journal of Pharmaceutical Science & Technology 1998, 52(5), 238-311; Strickley, R. G "Parenteral Formulations of Small Molecule Therapeutics Marketed in the United States (1999)-Part-1" PDA Journal of Pharmaceutical Science &t Technology 1999, 53(6), 324-349; and Nema, S. et al., "Excipients and Their Use in Injectable Products" PDA Journal of Pharmaceutical Science ft Technology 1997, 51(4), 166-171.

Commonly used pharmaceutical ingredients that can be used as appropriate to formulate the composition for its intended route of administration include:

acidifying agents (examples include but are not limited to acetic acid, citric acid, fumaric acid, hydrochloric acid, nitric acid);

alkalinizing agents (examples include but are not limited to ammonia solution, ammonium carbonate, diethanolamine, monoethanolamine, potassium hydroxide, sodium borate, sodium carbonate, sodium hydroxide, triethanolamine, trolamine);

adsorbents (examples include but are not limited to powdered cellulose and activated charcoal);

aerosol propellants (examples include but are not limited to carbon dioxide, $CCl_2F_2$, $F_2ClC-CClF_2$ and $CClF_3$)

air displacement agents (examples include but are not limited to nitrogen and argon);

antifungal preservatives (examples include but are not limited to benzoic acid, butylparaben, ethylparaben, methylparaben, propylparaben, sodium benzoate);

antimicrobial preservatives (examples include but are not limited to benzalkonium chloride, benzethonium chloride, benzyl alcohol, cetylpyridinium chloride, chlorobutanol, phenol, phenylethyl alcohol, phenylmercuric nitrate and thimerosal);

antioxidants (examples include but are not limited to ascorbic acid, ascorbyl palmitate, butylated hydroxyanisole, butylated hydroxytoluene, hypophosphorus acid, monothioglycerol, propyl gallate, sodium ascorbate, sodium bisulfite, sodium formaldehyde sulfoxylate, sodium metabisulfite);

binding materials (examples include but are not limited to block polymers, natural and synthetic rubber, polyacrylates, polyurethanes, silicones, polysiloxanes and styrene-butadiene copolymers);

buffering agents (examples include but are not limited to potassium metaphosphate, dipotassium phosphate, sodium acetate, sodium citrate anhydrous and sodium citrate dihydrate)

carrying agents (examples include but are not limited to acacia syrup, aromatic syrup, aromatic elixir, cherry syrup, cocoa syrup, orange syrup, syrup, corn oil, mineral oil, peanut oil, sesame oil, bacteriostatic sodium chloride injection and bacteriostatic water for injection)

chelating agents (examples include but are not limited to edetate disodium and edetic acid)

colourants (examples include but are not limited to FD&C Red No. 3, FD&C Red No. 20, FD&C Yellow No. 6, FD&C Blue No. 2, D&C Green No. 5, D&C Orange No. 5, D&C Red No. 8, caramel and ferric oxide red);

clarifying agents (examples include but are not limited to bentonite);

emulsifying agents (examples include but are not limited to acacia, cetomacrogol, cetyl alcohol, glyceryl monostearate, lecithin, sorbitan monooleate, polyoxyethylene 50 monostearate);

encapsulating agents (examples include but are not limited to gelatin and cellulose acetate phthalate)

flavourants (examples include but are not limited to anise oil, cinnamon oil, cocoa, menthol, orange oil, peppermint oil and vanillin);

humectants (examples include but are not limited to glycerol, propylene glycol and sorbitol);

levigating agents (examples include but are not limited to mineral oil and glycerin);

oils (examples include but are not limited to arachis oil, mineral oil, olive oil, peanut oil, sesame oil and vegetable oil);

ointment bases (examples include but are not limited to lanolin, hydrophilic ointment, polyethylene glycol ointment, petrolatum, hydrophilic petrolatum, white ointment, yellow ointment, and rose water ointment);

penetration enhancers (transdermal delivery) (examples include but are not limited to monohydroxy or polyhydroxy alcohols, mono- or polyvalent alcohols, saturated or unsaturated fatty alcohols, saturated or unsaturated fatty esters, saturated or unsaturated dicarboxylic acids, essential oils, phosphatidyl derivatives, cephalin, terpenes, amides, ethers, ketones and ureas)

plasticizers (examples include but are not limited to diethyl phthalate and glycerol);

solvents (examples include but are not limited to ethanol, corn oil, cottonseed oil, glycerol, isopropanol, mineral oil, oleic acid, peanut oil, purified water, water for injection, sterile water for injection and sterile water for irrigation);

stiffening agents (examples include but are not limited to cetyl alcohol, cetyl esters wax, microcrystalline wax, paraffin, stearyl alcohol, white wax and yellow wax);

suppository bases (examples include but are not limited to cocoa butter and polyethylene glycols (mixtures));

surfactants (examples include but are not limited to benzalkonium chloride, nonoxynol 10, oxtoxynol 9, polysorbate 80, sodium lauryl sulfate and sorbitan mono-palmitate);

suspending agents (examples include but are not limited to agar, bentonite, carbomers, carboxymethylcellulose sodium, hydroxyethyl cellulose, hydroxypropyl cellulose, hydroxypropyl methylcellulose, kaolin, methylcellulose, tragacanth and veegum);

sweetening agents (examples include but are not limited to aspartame, dextrose, glycerol, mannitol, propylene glycol, saccharin sodium, sorbitol and sucrose);

tablet anti-adherents (examples include but are not limited to magnesium stearate and talc);

tablet binders (examples include but are not limited to acacia, alginic acid, carboxymethylcellulose sodium, compressible sugar, ethylcellulose, gelatin, liquid glucose, methylcellulose, non-crosslinked polyvinyl pyrrolidone, and pregelatinized starch);

tablet and capsule diluents (examples include but are not limited to dibasic calcium phosphate, kaolin, lactose, mannitol, microcrystalline cellulose, powdered cellulose, precipitated calcium carbonate, sodium carbonate, sodium phosphate, sorbitol and starch);

tablet coating agents (examples include but are not limited to liquid glucose, hydroxyethyl cellulose, hydroxypropyl cellulose, hydroxypropyl methylcellulose, methylcellulose, ethylcellulose, cellulose acetate phthalate and shellac);

tablet direct compression excipients (examples include but are not limited to dibasic calcium phosphate);

tablet disintegrants (examples include but are not limited to alginic acid, carboxymethylcellulose calcium, microcrystalline cellulose, polacrillin potassium, cross-linked polyvinylpyrrolidone, sodium alginate, sodium starch glycollate and starch);

tablet glidants (examples include but are not limited to colloidal silica, corn starch and talc);

tablet lubricants (examples include but are not limited to calcium stearate, magnesium stearate, mineral oil, stearic acid and zinc stearate);

tablet/capsule opaquants (examples include but are not limited to titanium dioxide);

tablet polishing agents (examples include but are not limited to carnuba wax and white wax);

thickening agents (examples include but are not limited to beeswax, cetyl alcohol and paraffin);

tonicity agents (examples include but are not limited to dextrose and sodium chloride);

viscosity increasing agents (examples include but are not limited to alginic acid, bentonite, carbomers, carboxymethylcellulose sodium, methylcellulose, polyvinyl pyrrolidone, sodium alginate and tragacanth); and wetting agents (examples include but are not limited to heptadecaethylene oxycetanol, lecithins, sorbitol monooleate, polyoxyethylene sorbitol monooleate, and polyoxyethylene stearate).

Pharmaceutical compositions according to the present invention can be illustrated as follows:

Sterile IV Solution: A 5 mg/mL solution of the desired compound of this invention can be made using sterile, injectable water, and the pH is adjusted if necessary. The solution is diluted for administration to 1-2 mg/mL with sterile 5% dextrose and is administered as an IV infusion over about 60 minutes.

Lyophilised Powder for IV Administration: A sterile preparation can be prepared with (i) 100-1000 mg of the desired compound of this invention as a lyophilised powder, (ii) 32-327 mg/mL sodium citrate, and (iii) 300-3000 mg Dextran 40. The formulation is reconstituted with sterile, injectable saline or dextrose 5% to a concentration of 10 to 20 mg/mL, which is further diluted with saline or dextrose 5% to 0.2-0.4 mg/mL, and is administered either IV bolus or by IV infusion over 15-60 minutes.

Intramuscular Suspension: The following solution or suspension can be prepared, for intramuscular injection:

50 mg/mL of the desired, water-insoluble compound of this invention 5 mg/mL sodium carboxymethylcellulose 4 mg/mL TWEEN 80

9 mg/mL sodium chloride 9 mg/mL benzyl alcohol

Hard Shell Capsules: A Large number of unit capsules are prepared by filling standard two-piece hard galantine capsules each with 100 mg of powdered active ingredient, 150 mg of Lactose, 50 mg of cellulose and 6 mg of magnesium stearate.

Soft Gelatin Capsules: A mixture of active ingredient in a digestible oil such as soybean oil, cottonseed oil or olive oil is prepared and injected by means of a positive displacement pump into molten gelatin to form soft gelatin capsules containing 100 mg of the active ingredient. The capsules are washed and dried. The active ingredient can be dissolved in a mixture of polyethylene glycol, glycerin and sorbitol to prepare a water miscible medicine mix.

Tablets: A large number of tablets are prepared by conventional procedures so that the dosage unit is 100 mg of active ingredient, 0.2 mg. of colloidal silicon dioxide, 5 mg of magnesium stearate, 275 mg of microcrystalline cellulose, 11 mg. of starch, and 98.8 mg of Lactose. Appropriate aqueous and non-aqueous coatings may be applied to increase palatability, improve elegance and stability or delay absorption.

Immediate Release Tablets/Capsules: These are solid oral dosage forms made by conventional and novel processes. These units are taken orally without water for immediate dissolution and delivery of the medication. The active ingredient is mixed in a liquid containing ingredient such as sugar, gelatin, pectin and sweeteners. These liquids are solidified into solid tablets or caplets by freeze drying and solid state extraction techniques. The drug compounds may be compressed with viscoelastic and thermoelastic sugars and polymers or effervescent components to produce porous matrices intended for immediate release, without the need of water.

Combination Therapies

The term "combination" in the present invention is used as known to persons skilled in the art and may be present as a fixed combination, a non-fixed combination or kit-of-parts.

A "fixed combination" in the present invention is used as known to persons skilled in the art and is defined as a combination wherein the said first active ingredient and the said second active ingredient are present together in one unit dosage or in a single entity. One example of a "fixed combination" is a pharmaceutical composition wherein the said first active ingredient and the said second active ingredient are present in admixture for simultaneous administration, such as in a formulation. Another example of a "fixed combination" is a pharmaceutical combination wherein the said first active ingredient and the said second active ingredient are present in one unit without being in admixture.

A non-fixed combination or "kit-of-parts" in the present invention is used as known to persons skilled in the art and is defined as a combination wherein the said first active ingredient and the said second active ingredient are present in more than one unit. One example of a non-fixed combination or kit-of-parts is a combination wherein the said first active ingredient and the said second active ingredient are present separately. The components of the non-fixed combination or kit-of-parts may be administered separately, sequentially, simultaneously, concurrently or chronologically staggered.

The compounds of this invention can be administered as the sole pharmaceutical agent or in combination with one or more other pharmaceutical agents where the combination causes no unacceptable adverse effects. The present invention relates also to such combinations. For example, the compounds of this invention can be combined with known chemotherapeutic agents or anti-cancer agents, e.g. anti-hyperproliferative or other indication agents, and the like, as well as with admixtures and combinations thereof. Other indication agents include, but are not limited to, anti-angiogenic agents, mitotic inhibitors, alkylating agents, anti-metabolites, DNA-intercalating antibiotics, growth factor inhibitors, cell cycle inhibitors, enzyme inhibitors, toposisomerase inhibitors, biological response modifiers, or anti-hormones.

The terms "chemotherapeutic agent" and anti-cancer agent", include but are not limited to 131I-chTNT, abarelix, abiraterone, aclarubicin, aldesleukin, alemtuzumab, alitretinoin, altretamine, aminoglutethimide, amrubicin, amsacrine, anastrozole, arglabin, arsenic trioxide, asparaginase, azacitidine, basiliximab, BAY 80-6946, BAY 1000394, BAY 86-9766 (RDEA 119), belotecan, bendamustine, bevacizumab, bexarotene, bicalutamide, bisantrene, bleomycin, bortezomib, buserelin, busulfan, cabazitaxel, calcium folinate, calcium levofolinate, capecitabine, carboplatin, carmofur, carmustine, catumaxomab, celecoxib, celmoleukin, cetuximab, chlorambucil, chlormadinone, chlormethine, cisplatin, cladribine, clodronic acid, clofarabine, crisantaspase, cyclophosphamide, cyproterone, cytarabine, dacarbazine, dactinomycin, darbepoetin alfa, dasatinib, daunorubicin, decitabine, degarelix, denileukin diftitox, denosumab, deslorelin, dibrospidium chloride, docetaxel, doxifluridine, doxorubicin, doxorubicin+estrone, eculizumab, edrecolomab, elliptinium acetate, eltrombopag, endostatin, enocitabine, epirubicin, epitiostanol, epoetin alfa, epoetin beta, eptaplatin, eribulin, erlotinib, estradiol, estramustine, etoposide, everolimus, exemestane, fadrozole, filgrastim, fludarabine, fluorouracil, flutamide, formestane, fotemustine, fulvestrant, gallium nitrate, ganirelix, gefitinib, gemcitabine, gemtuzumab, glutoxim, goserelin, histamine dihydrochloride, histrelin, hydroxycarbamide, 1-125 seeds, ibandronic acid, ibritumomab tiuxetan, idarubicin, ifosfamide, imatinib, imiquimod, improsulfan, interferon alfa, interferon beta, interferon gamma, ipilimumab, irinotecan, ixabepilone, lanreotide, lapatinib, lenalidomide, lenograstim, lentinan, letrozole, leuprorelin, levamisole, lisuride, lobaplatin, lomustine, lonidamine, masoprocol, medroxyprogesterone, megestrol, melphalan, mepitiostane, mercaptopurine, methotrexate, methoxsalen, Methyl aminolevulinate, methyltestosterone, mifamurtide, miltefosine, miriplatin, mitobronitol, mitoguazone, mitolactol, mitomycin, mitotane, mitoxantrone, nedaplatin, nelarabine, nilotinib, nilutamide, nimotuzumab, nimustine, nitracrine, ofatumumab, omeprazole, oprelvekin, oxaliplatin, p53 gene therapy, paclitaxel, palifermin, palladium-103 seed, pamidronic acid, panitumumab, pazopanib, pegaspargase, PEG-epoetin beta (methoxy PEG-epoetin beta), pegfilgrastim, peginterferon alfa-2b, pemetrexed, pentazocine, pentostatin, peplomycin, perfosfamide, picibanil, pirarubicin, plerixafor, plicamycin, poliglusam, polyestradiol phosphate, polysaccharide-K, porfimer sodium, pralatrexate, prednimustine, procarbazine, quinagolide, raloxifene, raltitrexed, ranimustine, razoxane, regorafenib, risedronic acid, rituximab, romidepsin, romiplostim, sargramostim, sipuleucel-T, sizofiran, sobuzoxane, sodium glycididazole, sorafenib, streptozocin, sunitinib, talaporfin, tamibarotene, tamoxifen, tasonermin, teceleukin, tegafur, tegafur+gimeracil+oteracil, temoporfin, temozolomide, temsirolimus, teniposide, testosterone, tetrofosmin, thalidomide, thiotepa, thymalfasin, tioguanine, tocilizumab, topotecan, toremifene, tositumomab, trabectedin, trastuzumab, treosulfan, tretinoin, trilostane, triptorelin, trofosfamide, tryptophan, ubenimex, valrubicin, vandetanib, vapreotide, vemurafenib, vinblastine, vincristine, vindesine, vinflunine, vinorelbine, vorinostat, vorozole, yttrium-90 glass microspheres, zinostatin, zinostatin stimalamer, zoledronic acid, zorubicin.

In a preferred embodiment, the compounds of the invention may be administered in combination with protein therapeutics which include, but are not limited to, an interferon (e.g., interferon .alpha., .beta., or .gamma.) supraagonistic monoclonal antibodies, Tuebingen, TRP-1 protein vaccine, Colostrinin, anti-FAP antibody, YH-16, gemtuzumab, infliximab, cetuximab, trastuzumab, denileukin diftitox, rituximab, thymosin alpha 1, bevacizumab, mecasermin, mecasermin rinfabate, oprelvekin, natalizumab, rhMBL, MFE-CP1+ZD-2767-P, ABT-828, ErbB2-specific immunotoxin, SGN-35, MT-103, rinfabate, AS-1402, B43-genistein, L-19 based radioimmunotherapeutics, AC-9301, NY-ESO-1 vaccine, IMC-1C11, CT-322, rhCC10, r(m)CRP, MORAb-009, aviscumine, MDX-1307, Her-2 vaccine, APC-8024, NGR-hTNF, rhH1.3, IGN-311, Endostatin, volociximab, PRO-1762, lexatumumab, SGN-40, pertuzumab, EMD-273063, L19-IL-2 fusion protein, PRX-321, CNTO-328, MDX-214, tigapotide, CAT-3888, labetuzumab, alpha-particle-emitting radioisotope-linked lintuzumab, EM-1421, HyperAcute vaccine, tucotuzumab celmoleukin, galiximab, HPV-16-E7, Javelin—prostate cancer, Javelin—melanoma, NY-ESO-1 vaccine, EGF vaccine, CYT-004-MelQbG10, WT1 peptide, oregovomab, ofatumumab, zalutumumab, cintredekin besudotox, WX-G250, Albuferon, aflibercept, denosumab, vaccine, CTP-37, efungumab, or 131I-chTNT-1/B. Monoclonal antibodies useful as the protein therapeutic include, but are not limited to, muromonab-CD3, abciximab, edrecolomab, daclizumab, gentuzumab, alemtuzumab, ibritumomab, cetuximab, bevicizumab, efalizumab, adalimumab, omalizumab, muromomab-CD3, rituximab, daclizumab, trastuzumab, palivizumab, basiliximab, and infliximab.

In another preferred embodiment, compound of general formula I as defined herein can optionally be administered in combination with one or more of the following: ARRY-162, ARRY-300, ARRY-704, AS-703026, AZD-5363, AZD-8055, BEZ-235, BGT-226, BKM-120, BYL-719, CAL-101, CC-223, CH-5132799, deforolimus, E-6201, enzastaurin, GDC-0032, GDC-0068, GDC-0623, GDC-0941, GDC-0973, GDC-0980, GSK-2110183, GSK-2126458, GSK-2141795, INK128, MK-2206, novolimus, OSI-027, perifosine, PF-04691502, PF-05212384, PX-866, rapamycin, RG-7167, RO-4987655, RO-5126766, setumetinib, TAK-733, trametinib, triciribine, UCN-01, WX-554, XL-147, XL-765, zotarotimus, ZSTK-474.

Generally, the use of cytotoxic and/or cytostatic agents in combination with a compound or composition of the present invention will serve to:
(1) yield better efficacy in reducing the growth of a tumor or even eliminate the tumor as compared to administration of either agent alone,
(2) provide for the administration of lesser amounts of the administered chemotherapeutic agents,
(3) provide for a chemotherapeutic treatment that is well tolerated in the patient with fewer deleterious pharmacological complications than observed with single agent chemotherapies and certain other combined therapies,
(4) provide for treating a broader spectrum of different cancer types in mammals, especially humans,
(5) provide for a higher response rate among treated patients,
(6) provide for a longer survival time among treated patients compared to standard chemotherapy treatments,
(7) provide a longer time for tumor progression, and/or
(8) yield efficacy and tolerability results at least as good as those of the agents used alone, compared to known instances where other cancer agent combinations produce antagonistic effects.

Methods of Sensitizing Cells to Radiation

In a distinct embodiment of the present invention, a compound of the present invention may be used to sensitize a cell to radiation. That is, treatment of a cell with a compound of the present invention prior to radiation treatment of the cell renders the cell more susceptible to DNA damage and cell death than the cell would be in the absence of any treatment with a compound of the invention. In one aspect, the cell is treated with at least one compound of the invention.

Thus, the present invention also provides a method of killing a cell, wherein a cell is administered one or more compounds of the invention in combination with conventional radiation therapy.

The present invention also provides a method of rendering a cell more susceptible to cell death, wherein the cell is treated with one or more compounds of the invention prior to the treatment of the cell to cause or induce cell death. In one aspect, after the cell is treated with one or more compounds of the invention, the cell is treated with at least one compound, or at least one method, or a combination thereof, in order to cause DNA damage for the purpose of inhibiting the function of the normal cell or killing the cell.

In one embodiment, a cell is killed by treating the cell with at least one DNA damaging agent. That is, after treating a cell with one or more compounds of the invention to sensitize the cell to cell death, the cell is treated with at least one DNA damaging agent to kill the cell. DNA damaging agents useful in the present invention include, but are not limited to, chemotherapeutic agents (e.g., cisplatinum), ionizing radiation (X-rays, ultraviolet radiation), carcinogenic agents, and mutagenic agents.

In another embodiment, a cell is killed by treating the cell with at least one method to cause or induce DNA damage. Such methods include, but are not limited to, activation of a cell signalling pathway that results in DNA damage when the pathway is activated, inhibiting of a cell signalling pathway that results in DNA damage when the pathway is inhibited, and inducing a biochemical change in a cell, wherein the change results in DNA damage. By way of a non-limiting example, a DNA repair pathway in a cell can be inhibited, thereby preventing the repair of DNA damage and resulting in an abnormal accumulation of DNA damage in a cell.

In one aspect of the invention, a compound of the invention is administered to a cell prior to the radiation or other induction of DNA damage in the cell. In another aspect of the invention, a compound of the invention is administered to a cell concomitantly with the radiation or other induction of DNA damage in the cell. In yet another aspect of the invention, a compound of the invention is administered to a cell immediately after radiation or other induction of DNA damage in the cell has begun.

In another aspect, the cell is in vitro. In another embodiment, the cell is in vivo.

As mentioned supra, the compounds of the present invention have surprisingly been found to effectively inhibit MKNK-1 and may therefore be used for the treatment or prophylaxis of diseases of uncontrolled cell growth, proliferation and/or survival, inappropriate cellular immune responses, or inappropriate cellular inflammatory responses, or diseases which are accompanied with uncontrolled cell growth, proliferation and/or survival, inappropriate cellular immune responses, or inappropriate cellular inflammatory responses, particularly in which the uncontrolled cell growth, proliferation and/or survival, inappropriate cellular immune responses, or inappropriate cellular inflammatory responses is mediated by MKNK-1, such as, for example, haematological tumours, solid tumours, and/or metastases thereof, e.g. Leukaemias and myelodysplastic syndrome, malignant lymphomas, head and neck tumours including brain tumours and brain metastases, tumours of the thorax including non-small cell and small cell lung tumours, gastrointestinal tumours, endocrine tumours, mammary and other gynaecological tumours, urological tumours including renal, bladder and prostate tumours, skin tumours, and sarcomas, and/or metastases thereof.

In accordance with another aspect therefore, the present invention covers a compound of general formula I, or a stereoisomer, a tautomer, an N-oxide, a hydrate, a solvate, or a salt thereof, particularly a pharmaceutically acceptable salt thereof, or a mixture of same, as described and defined herein, for use in the treatment or prophylaxis of a disease, as mentioned supra.

Another particular aspect of the present invention is therefore the use of a compound of general formula I, described supra, or a stereoisomer, a tautomer, an N-oxide, a hydrate, a solvate, or a salt thereof, particularly a pharmaceutically acceptable salt thereof, or a mixture of same, for the prophylaxis or treatment of a disease.

Another particular aspect of the present invention is therefore the use of a compound of general formula I described supra for manufacturing a pharmaceutical composition for the treatment or prophylaxis of a disease.

The diseases referred to in the two preceding paragraphs are diseases of uncontrolled cell growth, proliferation and/or survival, inappropriate cellular immune responses, or inappropriate cellular inflammatory responses, or diseases which are accompanied with uncontrolled cell growth, proliferation and/or survival, inappropriate cellular immune responses, or inappropriate cellular inflammatory responses, particularly in which the uncontrolled cell growth, proliferation and/or survival, inappropriate cellular immune responses, or inappropriate cellular inflammatory responses is mediated by MKNK-1, such as, for example, haematological tumours, solid tumours, and/or metastases thereof, e.g. leukaemias and myelodysplastic syndrome, malignant lymphomas, head and neck tumours including brain tumours and brain metastases, tumours of the thorax including non-small cell and small cell lung tumours, gastrointestinal tumours, endocrine tumours, mammary and other gynaecological tumours, urological tumours including renal, bladder and prostate tumours, skin tumours, and sarcomas, and/or metastases thereof.

The term "inappropriate" within the context of the present invention, in particular in the context of "inappropriate cellular immune responses, or inappropriate cellular inflammatory responses", as used herein, is to be understood as preferably meaning a response which is less than, or greater than normal, and which is associated with, responsible for, or results in, the pathology of said diseases.

Preferably, the use is in the treatment or prophylaxis of diseases, wherein the diseases are haemotological tumours, solid tumours and/or metastases thereof.

Method of Treating Hyper-Proliferative Disorders

The present invention relates to a method for using the compounds of the present invention and compositions thereof, to treat mammalian hyper-proliferative disorders. Compounds can be utilized to inhibit, block, reduce, decrease, etc., cell proliferation and/or cell division, and/or produce apoptosis. This method comprises administering to a mammal in need thereof, including a human, an amount of a compound of this invention, or a pharmaceutically acceptable salt, isomer, polymorph, metabolite, hydrate, solvate or ester thereof; etc. which is effective to treat the disorder. Hyper-proliferative disorders include but are not limited, e.g., psoriasis, keloids, and other hyperplasias affecting the skin, benign prostate hyperplasia (BPH), solid tumours, such as cancers of the breast, respiratory tract, brain, reproductive organs, digestive tract, urinary tract, eye, liver, skin, head and neck, thyroid, parathyroid and their distant metastases. Those disorders also include Lymphomas, sarcomas, and Leukaemias.

Examples of breast cancer include, but are not limited to invasive ductal carcinoma, invasive lobular carcinoma, ductal carcinoma in situ, and Lobular carcinoma in situ.

Examples of cancers of the respiratory tract include, but are not limited to small-cell and non-small-cell Lung carcinoma, as well as bronchial adenoma and pleuropulmonary blastoma.

Examples of brain cancers include, but are not limited to brain stem and hypophtalmic glioma, cerebellar and cerebral astrocytoma, medulloblastoma, ependymoma, as well as neuroectodermal and pineal tumour.

Tumours of the male reproductive organs include, but are not limited to prostate and testicular cancer. Tumours of the female reproductive organs include, but are not limited to endometrial, cervical, ovarian, vaginal, and vulvar cancer, as well as sarcoma of the uterus.

Tumours of the digestive tract include, but are not limited to anal, colon, colorectal, oesophageal, gallbladder, gastric, pancreatic, rectal, small-intestine, and salivary gland cancers.

Tumours of the urinary tract include, but are not Limited to bladder, penile, kidney, renal pelvis, ureter, urethral and human papillary renal cancers.

Eye cancers include, but are not limited to intraocular melanoma and retinoblastoma.

Examples of liver cancers include, but are not limited to hepatocellular carcinoma (liver cell carcinomas with or without fibrolamellar variant), cholangiocarcinoma (intrahepatic bite duct carcinoma), and mixed hepatocellular cholangiocarcinoma.

Skin cancers include, but are not limited to squamous cell carcinoma, Kaposi's sarcoma, malignant melanoma, Merkel cell skin cancer, and non-melanoma skin cancer.

Head-and-neck cancers include, but are not limited to laryngeal, hypopharyngeal, nasopharyngeal, oropharyngeal cancer, lip and oral cavity cancer and squamous cell. Lymphomas include, but are not limited to AIDS-related lymphoma, non-Hodgkin's lymphoma, cutaneous T-cell lymphoma, Burkitt lymphoma, Hodgkin's disease, and lymphoma of the central nervous system.

Sarcomas include, but are not limited to sarcoma of the soft tissue, osteosarcoma, malignant fibrous histiocytoma, lymphosarcoma, and rhabdomyosarcoma.

Leukemias include, but are not limited to acute myeloid leukemia, acute lymphoblastic leukemia, chronic lymphocytic leukemia, chronic myelogenous leukemia, and hairy cell leukemia.

These disorders have been well characterized in humans, but also exist with a similar etiology in other mammals, and can be treated by administering pharmaceutical compositions of the present invention.

The term "treating" or "treatment" as stated throughout this document is used conventionally, e.g., the management or care of a subject for the purpose of combating, alleviating, reducing, relieving, improving the condition of, etc., of a disease or disorder, such as a carcinoma.

Methods of Treating Kinase Disorders

The present invention also provides methods for the treatment of disorders associated with aberrant mitogen extracellular kinase activity, including, but not limited to stroke, heart failure, hepatomegaly, cardiomegaly, diabetes, Alzheimer's disease, cystic fibrosis, symptoms of xenograft rejections, septic shock or asthma.

Effective amounts of compounds of the present invention can be used to treat such disorders, including those diseases (e.g., cancer) mentioned in the Background section above. Nonetheless, such cancers and other diseases can be treated with compounds of the present invention, regardless of the mechanism of action and/or the relationship between the kinase and the disorder.

The phrase "aberrant kinase activity" or "aberrant serin threonin kinase activity," includes any abnormal expression or activity of the gene encoding the kinase or of the polypeptide it encodes. Examples of such aberrant activity, include, but are not limited to, over-expression of the gene or polypeptide; gene amplification; mutations which produce constitutively-active or hyperactive kinase activity; gene mutations, deletions, substitutions, additions, etc.

The present invention also provides for methods of inhibiting a kinase activity, especially of mitogen extracellular kinase, comprising administering an effective amount of a compound of the present invention, including salts, polymorphs, metabolites, hydrates, solvates, prodrugs (e.g.: esters) thereof, and diastereoisomeric forms thereof. Kinase activity can be inhibited in cells (e.g., in vitro), or in the cells of a mammalian subject, especially a human patient in need of treatment.

Methods of Treating Angiogenic Disorders

The present invention also provides methods of treating disorders and diseases associated with excessive and/or abnormal angiogenesis.

Inappropriate and ectopic expression of angiogenesis can be deleterious to an organism. A number of pathological conditions are associated with the growth of extraneous blood vessels. These include, e.g., diabetic retinopathy, ischemic retinal-vein occlusion, and retinopathy of prematurity [Aiello et al. New Engl. J. Med. 1994, 331, 1480; Peer et al. Lab. Invest. 1995, 72, 638], age-related macular degeneration [AMD; see, Lopez et al. Invest. Opththalmol. Vis. Sci. 1996, 37, 855], neovascular glaucoma, psoriasis, retrolental fibroplasias, angiofibroma, inflammation, rheumatoid arthritis (RA), restenosis, in-stent restenosis, vascular graft restenosis, etc. In addition, the increased blood supply associated with cancerous and neoplastic tissue, encourages growth, leading to rapid tumour enlargement and metastasis. Moreover, the growth of new blood and lymph vessels in a tumour provides an escape route for renegade cells, encouraging metastasis and the consequence spread of the cancer. Thus, compounds of the present invention can be utilized to treat and/or prevent any of the aforementioned angiogenesis disorders, e.g., by inhibiting and/or reducing blood vessel formation; by inhibiting, blocking, reducing, decreasing, etc. endothelial cell proliferation or other types involved in angiogenesis, as well as causing cell death or apoptosis of such cell types.

Dose and Administration

Based upon standard laboratory techniques known to evaluate compounds useful for the treatment of hyper-proliferative disorders and angiogenic disorders, by standard toxicity tests and by standard pharmacological assays for the determination of treatment of the conditions identified above in mammals, and by comparison of these results with the results of known medicaments that are used to treat these conditions, the effective dosage of the compounds of this invention can readily be determined for treatment of each desired indication. The amount of the active ingredient to be administered in the treatment of one of these conditions can vary widely according to such considerations as the particular compound and dosage unit employed, the mode of administration, the period of treatment, the age and sex of the patient treated, and the nature and extent of the condition treated.

The total amount of the active ingredient to be administered will generally range from about 0.001 mg/kg to about 200 mg/kg body weight per day, and preferably from about 0.01 mg/kg to about 20 mg/kg body weight per day. Clinically useful dosing schedules will range from one to three times a day dosing to once every four weeks dosing. In addition, "drug holidays" in which a patient is not dosed with a drug for a certain period of time, may be beneficial to the overall balance between pharmacological effect and tolerability. A unit dosage may contain from about 0.5 mg to about 1500 mg of active ingredient, and can be administered one or more times per day or less than once a day. The average daily dosage for administration by injection, including intravenous, intramuscular, subcutaneous and parenteral injections, and use of infusion techniques will preferably be from 0.01 to 200 mg/kg of total body weight. The average daily rectal dosage regimen will preferably be from 0.01 to 200 mg/kg of total body weight. The average daily vaginal dosage regimen will preferably be from 0.01 to 200 mg/kg of total body weight. The average daily topical dosage regimen will preferably be from 0.1 to 200 mg administered between one to four times daily. The transdermal concentration will preferably be that required to maintain a daily dose of from 0.01 to 200 mg/kg. The average daily inhalation dosage regimen will preferably be from 0.01 to 100 mg/kg of total body weight.

Of course the specific initial and continuing dosage regimen for each patient will vary according to the nature and severity of the condition as determined by the attending diagnostician, the activity of the specific compound employed, the age and general condition of the patient, time of administration, route of administration, rate of excretion of the drug, drug combinations, and the like. The desired mode of treatment and number of doses of a compound of the present invention or a pharmaceutically acceptable salt or ester or composition thereof can be ascertained by those skilled in the art using conventional treatment tests.

Preferably, the diseases of said method are haematological tumours, solid tumour and/or metastases thereof.

The compounds of the present invention can be used in particular in therapy and prevention, i.e. prophylaxis, of tumour growth and metastases, especially in solid tumours of all indications and stages with or without pre-treatment of the tumour growth.

Methods of testing for a particular pharmacological or pharmaceutical property are well known to persons skilled in the art.

The example testing experiments described herein serve to illustrate the present invention and the invention is not limited to the examples given.

Biological Assays

Examples were tested in selected biological assays one or more times. When tested more than once, data are reported as either average values or as median values, wherein the average value, also referred to as the arithmetic mean value, represents the sum of the values obtained divided by the number of times tested, and the median value represents the middle number of the group of values when ranked in ascending or descending order. If the number of values in the data set is odd, the median is the middle value. If the number of values in the data set is even, the median is the arithmetic mean of the two middle values.

Examples were synthesized one or more times. When synthesized more than once, data from biological assays represent average values or median values calculated utilizing data sets obtained from testing of one or more synthetic batch.

MKNK1 Kinase Assay

MKNK1-inhibitory activity of compounds of the present invention was quantified employing the MKNK1 TR-FRET assay as described in the following paragraphs.

A recombinant fusion protein of Glutathione-S-Transferase (GST, N-terminally) and human full-length MKNK1 (amino acids 1-424 and T344D of accession number BAA 19885.1), expressed in insect cells using baculovirus expression system and purified via glutathione sepharose affinity chromatography, was purchased from Carna Biosciences (product no 02-145) and used as enzyme. As substrate for the kinase reaction the biotinylated peptide biotin-Ahx-IKKRKLTRRKSLKG (C-terminus in amide form) was used which can be purchased e.g. form the company Biosyntan (Berlin-Buch, Germany).

For the assay 50 nL of a 100 fold concentrated solution of the test compound in DMSO was pipetted into a black low volume 384 well microtiter plate (Greiner Bio-One, Frickenhausen, Germany), 2 µL of a solution of MKNK1 in aqueous assay buffer [50 mM HEPES pH 7.5, 5 mM $MgCL_2$, 1.0 mM dithiothreitol, 0.005% (v/v) Nonidet-P40 (Sigma)] was added and the mixture was incubated for 15 min at 22° C. to allow pre-binding of the test compounds to the enzyme before the start of the kinase reaction. Then the kinase reaction was started by the addition of 3 µL of a solution of adenosine-triphosphate (ATP, 16.7 µM=>final conc. in the 5 µL assay volume is 10 µM) and substrate (0.1 µM=>final conc. in the 5 µL assay volume is 0.06 µM) in assay buffer and the resulting mixture was incubated for a reaction time of 45 min at 22° C. The concentration of MKNK1 was adjusted depending of the activity of the enzyme Lot and was chosen appropriate to have the assay in the linear range, typical concentrations were in the range of 0.05 µg/ml. The reaction was stopped by the addition of 5 µL of a solution of TR-FRET detection reagents (5 nM streptavidine-XL665 [Cisbio Bioassays, Codolet, France] and 1 nM anti-ribosomal protein S6 (pSer236)-antibody from Invitrogen [#44921G] and 1 nM LANCE EU-W1024 Labeled ProteinG [Perkin-Elmer, product no. AD0071]) in an aqueous EDTA-solution (100 mM EDTA, 0.1% (w/v) bovine serum albumin in 50 mM HEPES pH 7.5).

The resulting mixture was incubated for 1 h at 22° C. to allow the formation of complex between the phosphorylated biotinylated peptide and the detection reagents. Subsequently the amount of phosphorylated substrate was evaluated by measurement of the resonance energy transfer from the Eu-chelate to the streptavidine-XL. Therefore, the fluorescence emissions at 620 nm and 665 nm after excitation at 350 nm were measured in a TR-FRET reader, e.g. a Rubystar (BMG Labtechnologies, Offenburg, Germany) or a Viewlux (Perkin-Elmer). The ratio of the emissions at 665 nm and at 622 nm was taken as the measure for the amount of phosphorylated substrate. The data were normalised (enzyme reaction without inhibitor=0% inhibition, all other assay components but no enzyme=100% inhibition). Usually the test compounds were tested on the same microtiterplate in 11 different concentrations in the range of 20 µM to 0.1 nM (20 µM, 5.9 µM, 1.7 µM, 0.51 µM, 0.15 µM, 44 nM, 13 nM, 3.8 nM, 1.1 nM, 0.33 nM and 0.1 nM, the dilution series prepared separately before the assay on the level of the 100 fold concentrated solutions in DMSO by serial 1:3.4 dilutions) in duplicate values for each concentration and IC50 values were calculated by a 4 parameter fit using an inhouse software.

MKNK1 Kinase High ATP Assay

MKNK1-inhibitory activity at high ATP of compounds of the present invention after their preincubation with MKNK1 was quantified employing the TR-FRET-based MKNK1 high ATP assay as described in the following paragraphs.

A recombinant fusion protein of Glutathione-S-Transferase (GST, N-terminally) and human full-length MKNK1 (amino acids 1-424 and T344D of accession number BAA 19885.1), expressed in insect cells using baculovirus expression system and purified via glutathione sepharose affinity chromatography, was purchased from Carna Biosciences (product no 02-145) and used as enzyme. As substrate for the kinase reaction the biotinylated peptide biotin-Ahx-IKKRKLTRRKSLKG (C-terminus in amide form) was used, which can be purchased e.g. from the company Biosyntan (Berlin-Buch, Germany).

For the assay 50 nL of a 100 fold concentrated solution of the test compound in DMSO was pipetted into a black low volume 384 well microtiter plate (Greiner Bio-One, Frickenhausen, Germany), 2 µL of a solution of MKNK1 in aqueous assay buffer [50 mM HEPES pH 7.5, 5 mM $MgCL_2$, 1.0 mM dithiothreitol, 0.005% (v/v) Nonidet-P40 (Sigma)] was added and the mixture was incubated for 15 min at 22° C. to allow pre-binding of the test compounds to the enzyme before the start of the kinase reaction. Then the kinase reaction was started by the addition of 3 µL of a solution of adenosine-triphosphate (ATP, 3.3 mM=>final conc. in the 5 µL assay volume is 2 mM) and substrate (0.1 µM=>final conc. in the 5 µL assay volume is 0.06 µM) in assay buffer and the resulting mixture was incubated for a reaction time of 30 min at 22° C. The concentration of MKNK1 was adjusted depending of the activity of the enzyme lot and was chosen appropriate to have the assay in the linear range, typical concentrations were in the range of 0.003 µg/mL. The reaction was stopped by the addition of 5 µL of a solution of TR-FRET detection reagents (5 nM streptavidine-XL665 [Cisbio Bioassays, Codolet, France] and 1 nM anti-ribosomal protein S6 (pSer236)-antibody from Invitrogen [#44921G] and 1 nM LANCE EU-W1024 Labeled ProteinG [Perkin-Elmer, product no. AD0071]) in an aqueous EDTA-solution (100 mM EDTA, 0.1% (w/v) bovine serum albumin in 50 mM HEPES pH 7.5).

The resulting mixture was incubated for 1 h at 22° C. to allow the formation of complex between the phosphorylated biotinylated peptide and the detection reagents. Subsequently the amount of phosphorylated substrate was evaluated by measurement of the resonance energy transfer from the Eu-chelate to the streptavidine-XL. Therefore, the fluorescence emissions at 620 nm and 665 nm after excitation at 350 nm were measured in a TR-FRET reader, e.g. a Rubystar (BMG Labtechnologies, Offenburg, Germany) or a Viewlux (Perkin-Elmer). The ratio of the emissions at 665 nm and at 622 nm was taken as the measure for the amount of phosphorylated substrate. The data were normalised (enzyme reaction without inhibitor=0% inhibition, all other assay components but no enzyme=100% inhibition). Usually the test compounds were tested on the same microtiterplate in 11 different concentrations in the range of 20 µM to 0.1 nM (e.g. 20 µM, 5.9 µM, 1.7 µM, 0.51 µM, 0.15 µM, 44 nM, 13 nM, 3.8 nM, 1.1 nM, 0.33 nM and 0.1 nM, the dilution series prepared separately before the assay on the level of the 100 fold concentrated solutions in DMSO by serial dilutions, the exact concentrations may vary depending on the pipettor used) in duplicate values for each concentration and IC50 values were calculated by a 4 parameter fit using an inhouse software. Data are presented in Table 1.

TABLE 1

| Example | MKNK1 $IC_{50}$ [nM] |
|---|---|
| 1 | 27 |
| 2 | 27 |
| 3 | 7 |
| 4 | 19 |
| 5 | 4 |
| 6 | 19 |
| 7 | 44 |

TABLE 1-continued

| Example | MKNK1 IC$_{50}$ [nM] |
| --- | --- |
| 8 | 5 |
| 9 | 11 |
| 10 | 2 |
| 11 | 6 |
| 12 | 13 |
| 13 | 6 |
| 14 | 25 |
| 15 | 9 |
| 16 | 11 |
| 17 | 9 |
| 18 | 18 |
| 19 | 11 |
| 20 | 15 |
| 21 | 32 |
| 22 | 16 |
| 23 | 12 |
| 24 | 5 |
| 25 | 4 |
| 26 | 21 |
| 27 | 6 |
| 28 | 1 |
| 29 | 5 |
| 30 | 36 |
| 31 | 40 |
| 32 | 20 |
| 33 | 24 |
| 34 | 39 |
| 35 | 47 |
| 36 | 14 |

Mnk2 Kinase High ATP Assay

Mnk2-inhibitory activity at high ATP of compounds of the present invention after their preincubation with Mnk2 was quantified employing the TR-FRET-based Mnk2 high ATP assay as described in the following paragraphs.

A recombinant fusion protein of Glutathione-S-Transferase (GST, N-terminally) and human full-length Mnk2 (Genbank accession number NP_060042.2), expressed in insect cells using baculovirus expression system, purified via glutathione sepharose affinity chromatography, and activated in vitro with MAPK12, was purchased from Invitrogen (product no PV5608) and used as enzyme. As substrate for the kinase reaction the biotinylated peptide biotin-Ahx-IKKRKLTRRKSLKG (C-terminus in amide form) was used which can be purchased e.g. form the company Biosyntan (Berlin-Buch, Germany).

For the assay 50 nl of a 100 fold concentrated solution of the test compound in DMSO was pipetted into a black Low volume 384 well microtiter plate (Greiner Bio-One, Frickenhausen, Germany), 2 µl of a solution of Mnk2 in aqueous assay buffer [50 mM HEPES pH 7.5, 5 mM MgCL$_2$, 1.0 mM dithiothreitol, 0.005% (v/v) Nonidet-P40 (G-Biosciences, St. Louis, USA)] was added and the mixture was incubated for 15 min at 22° C. to allow pre-binding of the test compounds to the enzyme before the start of the kinase reaction. Then the kinase reaction was started by the addition of 3 µl of a solution of adenosine-tri-phosphate (ATP, 3.3 mM=>final conc. in the 5 µl assay volume is 2 mM) and substrate (0.1 µM=>final conc. in the 5 µl assay volume is 0.06 µM) in assay buffer and the resulting mixture was incubated for a reaction time of 30 min at 22° C. The concentration of Mnk2 was adjusted depending of the activity of the enzyme Lot and was chosen appropriate to have the assay in the linear range, typical concentrations were in the range of 0.0045 µg/mi. The reaction was stopped by the addition of 5 µL of a solution of TR-FRET detection reagents (5 nM streptavidine-XL665 [Cisbio Bioassays, Codolet, France] and 1 nM anti-ribosomal protein S6 (pSer236)-antibody from Invitrogen [#44921G] and 1 nM LANCE EU-W1024 Labeled ProteinG [Perkin-Elmer, product no. AD0071]) in an aqueous EDTA-solution (100 mM EDTA, 0.1% (w/v) bovine serum albumin in 50 mM HEPES pH 7.5).

The resulting mixture was incubated for 1 h at 22° C. to allow the formation of complex between the phosphorylated biotinylated peptide and the detection reagents. Subsequently the amount of phosphorylated substrate was evaluated by measurement of the resonance energy transfer from the Eu-chelate to the streptavidine-XL665. Therefore, the fluorescence emissions at 620 nm and 665 nm after excitation at 350 nm were measured in a TR-FRET reader, e.g. a Pherastar (BMG Labtechnologies, Offenburg, Germany) or a Viewlux (Perkin-Elmer). The ratio of the emissions at 665 nm and at 622 nm was taken as the measure for the amount of phosphorylated substrate. The data were normalised (enzyme reaction without inhibitor=0% inhibition, all other assay components but no enzyme=100% inhibition). Usually the test compounds were tested on the same microtiterplate in 11 different concentrations in the range of 20 µM to 0.1 nM (e.g. 20 µM, 5.9 µM, 1.7 µM, 0.51 µM, 0.15 µM, 44 nM, 13 nM, 3.8 nM, 1.1 nM, 0.33 nM and 0.1 nM, the dilution series prepared separately before the assay on the level of the 100 fold concentrated solutions in DMSO by serial dilutions, the exact concentrations may vary depending on the pipettor used) in duplicate values for each concentration and IC$_{50}$ values were calculated by a 4 parameter fit using an inhouse software.

EGFR Kinase Assay

EGFR inhibitory activity of compounds of the present invention was quantified employing the TR-FRET based EGFR assay as described in the following paragraphs.

Epidermal Growth Factor Receptor (EGFR) affinity purified from human carcinoma A431 cells (Sigma-Aldrich, #E3641) was used as kinase. As substrate for the kinase reaction the biotinylated peptide biotin-Ahx-AEEEEYFEL-VAKKK (C-terminus in amid form) was used which can be purchased e.g. form the company Biosynthan GmbH (Berlin-Buch, Germany).

For the assay 50 nL of a 100 fold concentrated solution of the test compound in DMSO was pipetted into a black low volume 384 well microtiter plate (Greiner Bio-One, Frickenhausen, Germany), 2 µL of a solution of EGFR in aqueous assay [50 mM Hepes/HCL pH 7.0, 1 mM MgCL$_2$, 5 mM MnCl$_2$, 0.5 mM activated sodium ortho-vanadate, 0.005% (v/v) Tween-20] were added and the mixture was incubated for 15 min at 22° C. to allow pre-binding of the test compounds to the enzyme before the start of the kinase reaction. Then the kinase reaction was started by the addition of 3 µL of a solution of adenosine-tri-phosphate (ATP, 16.7 µM=>final conc. in the 5 µL assay volume is 10 µM) and substrate (1.67 µM=>final conc. in the 5 µL assay volume is 1 µM) in assay buffer and the resulting mixture was incubated for a reaction time of 30 min at 22° C. The concentration of EGFR was adjusted depending of the activity of the enzyme lot and was chosen appropriate to have the assay in the linear range, typical concentration were in the range of 3 U/ml. The reaction was stopped by the addition of 5 µl of a solution of HTRF detection reagents (0.1 µM streptavidine-XL665 [Cis Biointernational] and 1 nM PT66-Tb-Chelate, an terbium-chelate labelled anti-phospho-tyrosine antibody from Cis Biointernational [instead of the PT66-Tb-chelate PT66-Eu-Cryptate from Perkin Elmer can also be used]) in an aqueous EDTA-solution (80 mM EDTA, 0.2% (w/v) bovine serum albumin in 50 mM HEPES pH 7.5).

The resulting mixture was incubated 1 h at 22° C. to allow the binding of the biotinylated phosphorylated peptide to the streptavidine-XL665 and the PT66-Eu-Chelate. Subsequently the amount of phosphorylated substrate was evaluated by measurement of the resonance energy transfer from the PT66-Eu-Chelate to the streptavidine-XL665. Therefore, the fluorescence emissions at 620 nm and 665 nm after excitation at 337 nm were measured in a HTRF reader, e.g. a Pherastar (BMG Labtechnologies, Offenburg, Germany) or a Viewlux (Perkin-Elmer). The ratio of the emissions at 665 nm and at 622 nm was taken as the measure for the amount of phosphorylated substrate. The data were normalised (enzyme reaction without inhibitor=0% inhibition, all other assay components but no enzyme=100% inhibition). Usually the test compounds were tested on the same microtiterplate in 11 different concentrations in the range of 20 µM to 0.1 nM (e.g. 20 µM, 5.9 µM, 1.7 µM, 0.51 µM, 0.15 µM, 44 nM, 13 nM, 3.8 nM, 1.1 nM, 0.33 nM and 0.1 nM, the dilution series prepared separately before the assay on the level of the 100 fold concentrated solutions in DMSO by serial dilutions, the exact concentrations may vary depending on the pipettor used) in duplicate values for each concentration and $IC_{50}$ values were calculated by a 4 parameter fit using an inhouse software.

CDK2/CycE Kinase Assay

CDK2/CycE inhibitory activity of compounds of the present invention can be quantified employing the CDK2/CycE TR-FRET assay as described in the following paragraphs.

Recombinant fusion proteins of GST and human CDK2 and of GST and human CycE, expressed in insect cells (Sf9) and purified by Glutathion-Sepharose affinity chromatography, can be purchased from ProQinase GmbH (Freiburg, Germany). As substrate for the kinase reaction biotinylated peptide biotin-Ttds-YISPLKSPYKISEG (C-terminus in amid form) can be used which can be purchased e.g. from the company JERINI peptide technologies (Berlin, Germany).

For the assay 50 nL of a 100 fold concentrated solution of the test compound in DMSO is pipetted into a black tow volume 384 well microtiter plate (Greiner Bio-One, Frickenhausen, Germany), 2 µL of a solution of CDK2/CycE in aqueous assay buffer [50 mM Tris/HCL pH 8.0, 10 mM $MgCl_2$, 1.0 mM dithiothreitol, 0.1 mM sodium ortho-vanadate, 0.01% (v/v) Nonidet-P40 (Sigma)] are added and the mixture is incubated for 15 min at 22° C. to allow pre-binding of the test compounds to the enzyme before the start of the kinase reaction. Then the kinase reaction is started by the addition of 3 µL of a solution of adenosine-tri-phosphate (ATP, 16.7 µM=>final conc. in the 5 µL assay volume is 10 µM) and substrate (1.25 µM=>final conc. in the 5 µL assay volume is 0.75 µM) in assay buffer and the resulting mixture is incubated for a reaction time of 25 min at 22° C. The concentration of CDK2/CycE is adjusted depending of the activity of the enzyme lot and is chosen appropriate to have the assay in the linear range, typical concentrations ae in the range of 130 ng/ml. The reaction is stopped by the addition of 5 µL of a solution of TR-FRET detection reagents (0.2 µM streptavidine-XL665 [Cisbio Bioassays, Codolet, France] and 1 nM anti-RB(pSer807/pSer811)-antibody from BD Pharmingen [#558389] and 1.2 nM LANCE EU-W1024 Labeled anti-mouse IgG antibody [Perkin-Elmer, product no. AD0077, as an alternative a Terbium-cryptate-labeled anti-mouse IgG antibody from Cisbio Bioassays can be used]) in an aqueous EDTA-solution (100 mM EDTA, 0.2% (w/v) bovine serum albumin in 100 mM HEPES/NaOH pH 7.0).

The resulting mixture is incubated 1 h at 22° C. to allow the formation of complex between the phosphorylated biotinylated peptide and the detection reagents. Subsequently the amount of phosphorylated substrate is evaluated by measurement of the resonance energy transfer from the Eu-chelate to the streptavidine-XL. Therefore, the fluorescence emissions at 620 nm and 665 nm after excitation at 350 nm is measured in a TR-FRET reader, e.g. a Rubystar (BMG Labtechnologies, Offenburg, Germany) or a Viewlux (Perkin-Elmer). The ratio of the emissions at 665 nm and at 622 nm is taken as the measure for the amount of phosphorylated substrate. The data are normalised (enzyme reaction without inhibitor=0% inhibition, all other assay components but no enzyme=100% inhibition). Usually the test compounds are tested on the same microtiterplate in 11 different concentrations in the range of 20 µM to 0.1 nM (20 µM, 5.9 µM, 1.7 µM, 0.51 µM, 0.15 µM, 44 nM, 13 nM, 3.8 nM, 1.1 nM, 0.33 nM and 0.1 nM, the dilution series prepared separately before the assay on the level of the 100 fold concentrated solutions in DMSO by serial 1:3.4 dilutions) in duplicate values for each concentration and IC50 values are calculated by a 4 parameter fit using an inhouse software.

PDGFRβ Kinase Assay

PDGFRβ inhibitory activity of compounds of the present invention can be quantified employing the PDGFRβ HTRF assay as described in the following paragraphs.

As kinase, a GST-His fusion protein containing a C-terminal fragment of human PDGFRβ (amino acids 561-1106, expressed in insect cells [SF9] and purified by affinity chromatography, purchased from Proqinase [Freiburg i.Brsg., Germany] is used. As substrate for the kinase reaction the biotinylated poly-Glu,Tyr (4:1) copolymer (#61GT0BLA) from Cis Biointernational (Marcoule, France) is used.

For the assay 50 nL of a 100 fold concentrated solution of the test compound in DMSO is pipetted into a black Low volume 384 well microtiter plate (Greiner Bio-One, Frickenhausen, Germany), 2 µL of a solution of PDGFRβ in aqueous assay buffer [50 mM HEPES/NaOH pH 7.5, 10 mM $MgCL_2$, 2.5 mM dithiothreitol, 0.01% (v/v) Triton-X100 (Sigma)] are added and the mixture was incubated for 15 min at 22° C. to allow pre-binding of the test compounds to the enzyme before the start of the kinase reaction. Then the kinase reaction is started by the addition of 3 µL of a solution of adenosine-tri-phosphate (ATP, 16.7 µM=>final conc. in the 5 µL assay volume is 10 µM) and substrate (2.27 µg/ml=>final conc. in the 5 µL assay volume is 1.36 µg/ml [~30 nM]) in assay buffer and the resulting mixture is incubated for a reaction time of 25 min at 22° C. The concentration of PDGFRβ in the assay is adjusted depending of the activity of the enzyme lot and is chosen appropriate to have the assay in the linear range, typical enzyme concentrations are in the range of about 125 pg/µL (final conc. in the 5 µL assay volume). The reaction is stopped by the addition of 5 µL of a solution of HTRF detection reagents (200 nM streptavidine-XLent [Cis Biointernational] and 1.4 nM PT66-Eu-Chelate, an europium-chelate Labelled anti-phospho-tyrosine antibody from Perkin Elmer [instead of the PT66-Eu-chelate PT66-Tb-Cryptate from Cis Biointernational can also be used]) in an aqueous EDTA-solution (100 mM EDTA, 0.2% (w/v) bovine serum albumin in 50 mM HEPES/NaOH pH 7.5).

The resulting mixture is incubated 1 h at 22° C. to allow the binding of the biotinylated phosphorylated peptide to the streptavidine-XLent and the PT66-Eu-Chelate. Subsequently the amount of phosphorylated substrate is evaluated by measurement of the resonance energy transfer from the PT66-Eu-Chelate to the streptavidine-XLent. Therefore, the fluorescence emissions at 620 nm and 665 nm after excitation at 350 nm is measured in a HTRF reader, e.g. a Rubystar (BMG Labtechnologies, Offenburg, Germany) or a Viewlux (Perkin-Elmer). The ratio of the emissions at 665 nm and at 622 nm is taken as the measure for the amount of phosphorylated substrate. The data are normalised (enzyme reaction without inhibitor=0% inhibition, all other assay components but no enzyme=100% inhibition). Normally test compound are tested on the same microtiter plate at 10 different concentrations in the range of 20 μM to 1 nM (20 μM, 6.7 μM, 2.2 μM, 0.74 μM, 0.25 μM, 82 nM, 27 nM, 9.2 nM, 3.1 nM and 1 nM, dilution series prepared before the assay at the level of the 100 fold conc. stock solutions by serial 1:3 dilutions) in duplicate values for each concentration and $IC_{50}$ values are calculated by a 4 parameter fit using an inhouse software.

Fyn Kinase Assay

C-terminally His6-tagged human recombinant kinase domain of the human T-Fyn expressed in baculovirus infected insect cells (purchased from Invitrogen, P3042) is used as kinase. As substrate for the kinase reaction the biotinylated peptide biotin-KVEKIGEGTYGW (C-terminus in amid form) is used which can be purchased e.g. form the company Biosynthan GmbH (Berlin-Buch, Germany).

For the assay 50 nL of a 100 fold concentrated solution of the test compound in DMSO is pipetted into a black Low volume 384 well microtiter plate (Greiner Bio-One, Frickenhausen, Germany), 2 μL of a solution of T-Fyn in aqueous assay buffer [25 mM Tris/HCL pH 7.2, 25 mM $MgCL_2$, 2 mM dithiothreitol, 0.1% (w/v) bovine serum albumin, 0.03% (v/v) Nonidet-P40 (Sigma)]. are added and the mixture is incubated for 15 min at 22° C. to allow pre-binding of the test compounds to the enzyme before the start of the kinase reaction. Then the kinase reaction is started by the addition of 3 μL of a solution of adenosine-tri-phosphate (ATP, 16.7 μM=>final conc. in the 5 μL assay volume is 10 μM) and substrate (2 μM=>final conc. in the 5 μL assay volume is 1.2 μM) in assay buffer and the resulting mixture is incubated for a reaction time of 60 min at 22° C. The concentration of Fyn is adjusted depending of the activity of the enzyme Lot and is chosen appropriate to have the assay in the linear range, typical concentration was 0.13 nM. The reaction is stopped by the addition of 5 μL of a solution of HTRF detection reagents (0.2 μM streptavidine-XL [Cisbio Bioassays, Codolet, France) and 0.66 nM PT66-Eu-Chelate, an europium-chelate Labelled anti-phospho-tyrosine antibody from Perkin Elmer [instead of the PT66-Eu-chelate PT66-Tb-Cryptate from Cisbio Bioassays can also be used]) in an aqueous EDTA-solution (125 mM EDTA, 0.2% (w/v) bovine serum albumin in 50 mM HEPES/NaOH pH 7.0).

The resulting mixture is incubated 1 h at 22° C. to allow the binding of the biotinylated phosphorylated peptide to the streptavidine-XL and the PT66-Eu-Chelate. Subsequently the amount of phosphorylated substrate is evaluated by measurement of the resonance energy transfer from the PT66-Eu-Chelate to the streptavidine-XL. Therefore, the fluorescence emissions at 620 nm and 665 nm after excitation at 350 nm is measured in a HTRF reader, e.g. a Rubystar (BMG Labtechnologies, Offenburg, Germany) or a Viewlux (Perkin-Elmer). The ratio of the emissions at 665 nm and at 622 nm is taken as the measure for the amount of phosphorylated substrate. The data are normalised (enzyme reaction without inhibitor=0% inhibition, all other assay components but no enzyme=100% inhibition). Normally test compounds are tested on the same microtiter plate at 10 different concentrations in the range of 20 μM to 1 nM (20 μM, 6.7 μM, 2.2 μM, 0.74 μM, 0.25 μM, 82 nM, 27 nM, 9.2 nM, 3.1 nM and 1 nM, dilution series prepared before the assay at the level of the 100 fold conc. stock solutions by serial 1:3 dilutions) in duplicate values for each concentration and $IC_{50}$ values are calculated by a 4 parameter fit using an inhouse software.

Flt4 Kinase Assay

Flt4 inhibitory activity of compounds of the present invention can be quantified employing the Flt4 TR-FRET assay as described in the following paragraphs.

As kinase, a GST-His fusion protein containing a C-terminal fragment of human Flt4 (amino acids 799-1298, expressed in insect cells [SF9] and purified by affinity chromatography, purchased from Proqinase [Freiburg i.Brsg., Germany] is used. As substrate for the kinase reaction the biotinylated peptide Biotin-Ahx-GGEEEEYFELVKKKK (C-terminus in amide form, purchased from Biosyntan, Berlin-Buch, Germany) is used.

For the assay 50 nL of a 100 fold concentrated solution of the test compound in DMSO was pipetted into a black low volume 384 well microtiter plate (Greiner Bio-One, Frickenhausen, Germany), 2 μL of a solution of Flt4 in aqueous assay buffer [25 mM HEPES pH 7.5, 10 mM $MgCl_2$, 2 mM dithiothreitol, 0.01% (v/v) Triton-X100 (Sigma), 0.5 mM EGTA, and 5 mM B-phospho-glycerol] are added and the mixture is incubated for 15 min at 22° C. to allow pre-binding of the test compounds to the enzyme before the start of the kinase reaction. Then the kinase reaction is started by the addition of 3 μL of a solution of adenosine-tri-phosphate (ATP, 16.7 μM=>final conc. in the 5 μL assay volume is 10 μM) and substrate (1.67 μM=>final conc. in the 5 μL assay volume is 1 μM) in assay buffer and the resulting mixture is incubated for a reaction time of 45 min at 22° C. The concentration of Flt4 in the assay is adjusted depending of the activity of the enzyme lot and was chosen appropriate to have the assay in the linear range, typical enzyme concentrations are in the range of about 120 pg/μL (final conc. in the 5 μL assay volume). The reaction is stopped by the addition of 5 μL of a solution of HTRF detection reagents (200 nM streptavidine-XL665 [Cis Biointernational] and 1 nM PT66-Tb-Cryptate, an terbium-cryptate labelled anti-phospho-tyrosine antibody from Cisbio Bioassays (Codolet, France) in an aqueous EDTA-solution (50 mM EDTA, 0.2% (w/v) bovine serum albumin in 50 mM HEPES pH 7.5).

The resulting mixture is incubated 1 h at 22° C. to allow the binding of the biotinylated phosphorylated peptide to the streptavidine-XL665 and the PT66-Tb-Cryptate. Subsequently the amount of phosphorylated substrate is evaluated by measurement of the resonance energy transfer from the PT66-Tb-Cryptate to the streptavidine-XL665. Therefore, the fluorescence emissions at 620 nm and 665 nm after excitation at 350 nm is measured in a HTRF reader, e.g. a Rubystar (BMG Labtechnologies, Offenburg, Germany) or a Viewlux (Perkin-Elmer). The ratio of the emissions at 665 nm and at 622 nm is taken as the measure for the amount of phosphorylated substrate. The data are normalised (enzyme reaction without inhibitor=0% inhibition, all other assay components but no enzyme=100% inhibition). Normally test compound are tested on the same microtiter plate at 10 different concentrations in the range of 20 μM to 1 nM (20 μM, 6.7 μM, 2.2 μM, 0.74 μM, 0.25 μM, 82 nM, 27 nM, 9.2 nM, 3.1 nM and 1 nM, dilution series prepared before the assay at the level of the 100 fold conc. stock solutions by serial 1:3 dilutions) in duplicate values for each concentration and $IC_{50}$ values are calculated by a 4 parameter fit using an inhouse software.

TrkA Kinase Assay

TrkA inhibitory activity of compounds of the present invention can be quantified employing the TrkA HTRF assay as described in the following paragraphs.

As kinase, a GST-His fusion protein containing a C-terminal fragment of human TrkA (amino acids 443-796, expressed in insect cells [SF9] and purified by affinity chromatography, purchased from Proqinase [Freiburg i.Brsg., Germany] is used. As substrate for the kinase reaction the biotinylated poly-Glu,Tyr (4:1) copolymer (#61GT0BLA) from Cis Biointernational (Marcoule, France) is used.

For the assay 50 nL of a 100 fold concentrated solution of the test compound in DMSO is pipetted into a black low volume 384 well microtiter plate (Greiner Bio-One, Frickenhausen, Germany), 2 μL of a solution of TrkA in aqueous assay buffer [8 mM MOPS/HCL pH 7.0, 10 mM $MgCL_2$, 1 mM dithiothreitol, 0.01% (v/v) NP-40 (Sigma), 0.2 mM EDTA] are added and the mixture was incubated for 15 min at 22° C. to allow pre-binding of the test compounds to the enzyme before the start of the kinase reaction. Then the kinase reaction is started by the addition of 3 μL of a solution of adenosine-tri-phosphate (ATP, 16.7 μM=>final conc. in the 5 μL assay volume is 10 μM) and substrate (2.27 μg/ml=>final conc. in the 5 μL assay volume is 1.36 μg/ml [~30 nM]) in assay buffer and the resulting mixture is incubated for a reaction time of 60 min at 22° C. The concentration of TrkA in the assay is adjusted depending of the activity of the enzyme Lot and is chosen appropriate to have the assay in the linear range, typical enzyme concentrations are in the range of about 20 pg/μL (final conc. in the 5 μL assay volume). The reaction is stopped by the addition of 5 μL of a solution of HTRF detection reagents (30 nM streptavidine-XL665 [Cis Biointernational] and 1.4 nM PT66-Eu-Chelate, an europium-chelate labelled anti-phospho-tyrosine antibody from PerkinElmer [instead of the PT66-Eu-chelate PT66-Tb-Cryptate from Cis Biointernational can also be used]) in an aqueous EDTA-solution (100 mM EDTA, 0.2% (w/v) bovine serum albumin in 50 mM HEPES/NaOH pH 7.5).

The resulting mixture is incubated 1 h at 22° C. to allow the binding of the biotinylated phosphorylated peptide to the streptavidine-XL665 and the PT66-Eu-Chelate. Subsequently the amount of phosphorylated substrate is evaluated by measurement of the resonance energy transfer from the PT66-Eu-Chelate to the streptavidine-XL665. Therefore, the fluorescence emissions at 620 nm and 665 nm after excitation at 350 nm is measured in a HTRF reader, e.g. a Rubystar (BMG Labtechnologies, Offenburg, Germany) or a Viewlux (Perkin-Elmer). The ratio of the emissions at 665 nm and at 622 nm is taken as the measure for the amount of phosphorylated substrate. The data are normalised (enzyme reaction without inhibitor=0% inhibition, all other assay components but no enzyme=100% inhibition). Normally test compound are tested on the same microtiter plate at 10 different concentrations in the range of 20 μM to 1 nM (20 μM, 6.7 μM, 2.2 μM, 0.74 μM, 0.25 μM, 82 nM, 27 nM, 9.2 nM, 3.1 nM and 1 nM, dilution series prepared before the assay at the level of the 100 fold conc. stock solutions by serial 1:3 dilutions) in duplicate values for each concentration and $IC_{50}$ values are calculated by a 4 parameter fit using an inhouse software.

AlphaScreen SureFire eIF4E Ser209 Phosphorylation Assay

The AlphaScreen SureFire eIF4E Ser209 phoshorylation assay can be used to measure the phosphorylation of endogenous eIF4E in cellular lysates. The AlphaScreen SureFire technology allows the detection of phosphorylated proteins in cellular lysates. In this assay, sandwich antibody complexes, which are only formed in the presence of the analyte (p-eIF4E Ser209), are captured by AlphaScreen donor and acceptor beads, bringing them into close proximity. The excitation of the donor bead provokes the release of singlet oxygen molecules that triggers a cascade of energy transfer in the Acceptor beads, resulting in the emission of light at 520-620 nm.

Surefire EIF4e Alphascreen in A549 Cells with 20% FCS Stimulation

For the assay the AlphaScreen SureFire p-eIF4E Ser209 10K Assay Kit and the AlphaScreen ProteinA Kit (for 10K assay points) both from Perkin Elmer are used.

On day one 50.000 A549 cells are plated in a 96-well plate in 100 μL per well in growth medium (DMEM/Hams' F12 with stable Glutamin, 10% FCS) and incubated at 37° C. After attachment of the cells, medium is changed to starving medium (DMEM, 0.1% FCS, without Glucose, with Glutamin, supplemented with 5 g/L Maltose). On day two, test compounds are serially diluted in 50 μL starving medium with a final DMSO concentration of 1% and are added to A549 cells in test plates at a final concentration range from as high 10 μM to as low 10 nM depending on the activities of the tested compounds. Treated cells are incubated at 37° C. for 2 h. 37 ul FCS is added to the wells (=final FCS concentration 20%) for 20 min. Then medium is removed and cells are lysed by adding 50 μL lysis buffer. Plates are then agitated on a plate shaker for 10 min. After 10 min lysis time, 4 μL of the lysate is transferred to a 384 well plate (Proxiplate from Perkin Elmer) and 5 μL Reaction Buffer plus Activation Buffer mix containing AlphaScreen Acceptor beads is added. Plates are sealed with TopSeal-A adhesive film, gently agitated on a plate shaker for 2 hours at room temperature. Afterwards 2 μL Dilution buffer with AlphaScreen Donor beads are added under subdued light and plates are sealed again with TopSeal-A adhesive film and covered with foil. Incubation takes place for further 2 h gently agitation at room temperature. Plates are then measured in an EnVision reader (Perkin Elmer) with the AlphaScreen program. Each data point (compound dilution) is measured as triplicate.

The $IC_{50}$ values are determined by means of a 4-parameter fit using the company's own software.

Proliferation Assays

The tumor cell proliferation assay which can be used to test the compounds of the present invention involves a readout called Cell Titer-Glow® Luminescent Cell Viability Assay developed by Promega® (B. A. Cunningham, "A Growing Issue: Cell Proliferation Assays, Modern kits ease quantification of cell growth", The Scientist 2001, 15(13), 26; S. P. Crouch et al., "The use of ATP bioluminescence as a measure of cell proliferation and cytotoxicity", *Journal of Immunological Methods* 1993, 160, 81-88), that measures inhibition of cell proliferation. Generation of a luminescent signal corresponds to the amount of ATP present, which is directly proportional to the number of metabolically active (proliferating) cells.

In Vitro Tumor Cell Proliferation Assay:

Cultivated tumour cells (MOLM-13 (human acute myeloid leukemia cells obtained from DSMZ #ACC 554), JJN-3 (human plasma cell leukemia cells obtained from DSMZ #ACC 541), Ramos (RA1) (human Burkitt's lymphoma cells obtained from ATCC #CRL-159)) are plated at a density of 2,500 cells/well (JJN-3), 3,000 cells/well (MOLM-13), 4,000 cells/well (Ramos (RA1)), in a 96-well multititer plate (Costar 3603 black/clear bottom) in 100 μL of their respective growth medium supplemented with 10% fetal calf serum. After 24 hours, the cells of one plate (zero-point plate) are measured for viability. Therefore, 70 μL/well CTG solution (Promega Cell Titer Glo solution (catalog #G755B and G756B)) is added to zero-point plate. The plates are mixed for two minutes on orbital shaker to ensure cell tysis and incubated for ten minutes at room temperature in the dark to stabilize luminescence signal. The samples are read on a VICTOR 3 μlate reader. In parallel, serially test compounds are diluted in growth medium, and 50 μL of 3× dilutions/well are pipetted into the test plates (final concentrations: 0 μM, as well as in the range of 0.001-30 μM). The final concentration of the solvent dimethyl sulfoxide is 0.3-0.4%. The cells are incubated for 3 days in the presence of test substances. 105 μL/well CTG solution (Promega Cell Titer Glo solution (catalog #G755B and G756B)) is added to the test wells. The plates are mixed for 2 minutes on an orbital shaker to ensure cell tysis and incubated for 10 min at room temperature in the dark to stabilize luminescence signal. The samples are read on a VICTOR 3 μlate reader. The change of cell number, in percent, is calculated by normalization of the measured values to the extinction values of the zero-point plate (=0%) and the extinction of the untreated (0 μm) cells (=100%). The $IC_{50}$ values (inhibitory concentration at 50% of maximal effect) are determined by means of a 4 parameter fit using the company's own software.

Overview Cell Lines for Proliferation Assays

| Cell line | Origin | Cell number/well | Culture Medium |
|---|---|---|---|
| MOLM-13 (obtained from DSMZ # ACC 554) | human acute myeloid leukemia | 3000 | RPMI 1640 with stable Glutamin with 10% Fetal Bovine Serum |
| JJN-3 (obtained from DSMZ # ACC 541) | human plasma cell leukemia | 2500 | 45% Dulbecco's Modified Eagle Medium with stable Glutamin, 45% Iscove's Modified Dulbecco's Media with stable Glutamin and 10% Fetal Bovine Serum |
| Ramos (RA1) (obtained from ATCC # CRL-159) | human Burkitt's lymphoma | 4000 | RPMI 1640 media with stable Glutamin with 10% Fetal Bovine Serum |

Thus the compounds of the present invention effectively inhibit one or more kinases and are therefore suitable for the treatment or prophylaxis of diseases of uncontrolled cell growth, proliferation and/or survival, inappropriate cellular immune responses, or inappropriate cellular inflammatory responses, particularly in which the uncontrolled cell growth, proliferation and/or survival, inappropriate cellular immune responses, or inappropriate cellular inflammatory responses is mediated by MKNK-1, more particularly in which the diseases of uncontrolled cell growth, proliferation and/or survival, inappropriate cellular immune responses, or inappropriate cellular inflammatory responses are haemotological tumours, solid tumours and/or metastases thereof, e.g. Leukaemias and myelodysplastic syndrome, malignant lymphomas, head and neck tumours including brain tumours and brain metastases, tumours of the thorax including non-small cell and small cell lung tumours, gastrointestinal tumours, endocrine tumours, mammary and other gynaecological tumours, urological tumours including renal, bladder and prostate tumours, skin tumours, and sarcomas, and/or metastases thereof.

The invention claimed is:
1. A compound of general formula I:

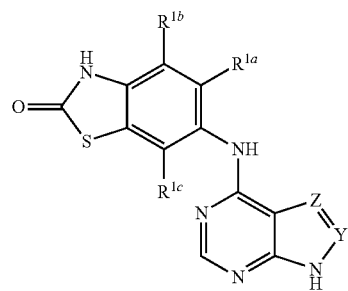

I in which:
$R^{1a}$ represents a hydrogen atom or a halogen atom or a hydroxy-, cyano-, $C_1$-$C_6$-alkyl-, halo-$C_1$-$C_6$-alkyl-, $C_1$-$C_6$-alkoxy-, halo-$C_1$-$C_6$-alkoxy-, $C_3$-$C_6$-cycloalkyloxy-, (3- to 10-membered heterocycloalkyl)-O—, —$NR^{5a}R^{5b}$, —$SCF_3$ or —$SF_5$ group;

$R^{1b}$ represents a hydrogen atom or a halogen atom or a hydroxy-, cyano-, $C_1$-$C_6$-alkyl-, halo-$C_1$-$C_6$-alkyl-, $C_1$-$C_6$-alkoxy-, halo-$C_1$-$C_6$-alkoxy-, $C_3$-$C_6$-cycloalkyloxy-, (3- to 10-membered heterocycloalkyl)-O—, —$NR^{5a}R^{5b}$, —$SCF_3$ or —$SF_5$ group;

$R^{1c}$ represents a hydrogen atom or a halogen atom or a hydroxy-, cyano-, $C_1$-$C_6$-alkyl-, halo-$C_1$-$C_6$-alkyl-, $C_1$-$C_6$-alkoxy-, halo-$C_1$-$C_6$-alkoxy-, $C_3$-$C_6$-cycloalkyloxy-, (3- to 10-membered heterocycloalkyl)-O—, —$NR^{5a}R^{5b}$, —$SCF_3$ or —$SF_5$ group;

Y represents N or $CR^{2a}$;
Z represents N or $CR^{2b}$;
with the proviso that not more than one of Y and Z represents N;

$R^{2a}$ represents a hydrogen atom or a halogen atom or a group selected from:
$C_1$-$C_6$-alkyl-, $C_2$-$C_6$-alkenyl-, $C_2$-$C_6$-alkynyl-, $C_3$-$C_6$-cycloalkyl-, 3- to 10-membered heterocycloalkyl-, 4- to 10-membered heterocycloalkenyl-, aryl-, heteroaryl-, halo-$C_1$-$C_3$-alkyl-, cyano-, —$(CH_2)_q$—X—$(CH_2)_p$-$R^3$;
wherein said $C_1$-$C_6$-alkyl-, $C_3$-$C_6$-cycloalkyl-, 3- to 10-membered heterocycloalkyl-, 4- to 10-membered heterocycloalkenyl-, aryl- or heteroaryl-group is optionally substituted, identically or differently, with 1, 2, 3, 4 or 5 $R^4$ groups;

$R^{2b}$ represents a hydrogen atom or a halogen atom or a group selected from:
$C_1$-$C_6$-alkyl-, $C_2$-$C_6$-alkenyl-, $C_2$-$C_6$-alkynyl-, $C_3$-$C_6$-cycloalkyl-, 3- to 10-membered heterocycloalkyl-, 4- to 10-membered heterocycloalkenyl-, aryl,heteroaryl-, halo-$C_1$-$C_3$-alkyl-, cyano-, —$(CH_2)_q$—X—$(CH_2)_p$-$R^3$;
wherein said $C_1$-$C_6$-alkyl-, $C_3$-$C_6$-cycloalkyl-, 3- to 10-membered heterocycloalkyl-, 4- to 10-membered heterocycloalkenyl-, aryl- or heteroaryl-group is optionally substituted, identically or differently, with 1, 2, 3, 4 or 5 $R^4$ groups;

X represents a bond or a bivalent group selected from: —O—, —S—, —S(=O)—, —S(=O)$_2$—, —S(=O)—($NR^{3a}$)—, —($NR^{3a}$)—S(=O)—, —C(=O)—, —($NR^{3a}$)—, —C(=O)—O—, —O—C(=O)—, —C(=S)—O—, —O—C(=S)—, —C(=O)—($NR^{3a}$)—, —($NR^{3a}$)—C(=O)—, —($NR^{3a}$)—C(=O)—($NR^{3b}$)—, —O—C(=O)—($NR^{3a}$)—, —($NR^{3a}$)—C(=O)—O—;

$R^3$ represents a hydrogen atom or a group selected from $C_1$-$C_6$-alkyl-, $C_3$-$C_6$-cycloalkyl-, 3- to 10-membered heterocycloalkyl-, aryl-, heteroaryl-, halo-$C_1$-$C_3$-alkyl-; wherein said $C_1$-$C_6$-alkyl-, $C_3$-$C_6$-cycloalkyl-, 3- to 10-membered heterocycloalkyl-, aryl- or heteroaryl-group is optionally substituted, identically or differently, with 1, 2, 3, 4 or 5 $R^4$ groups;

$R^{3a}$ represents a hydrogen atom or a group selected from $C_1$-$C_6$-alkyl-, $C_3$-$C_6$-cycloalkyl-, 3- to 10-membered heterocycloalkyl-, aryl-, heteroaryl-, halo-$C_1$-$C_3$-alkyl-; wherein said $C_1$-$C_6$-alkyl-, $C_3$-$C_6$-cycloalkyl-, 3- to 10-membered heterocycloalkyl-, aryl- or heteroaryl-group is optionally substituted, identically or differently, with 1, 2, 3, 4 or 5 $R^4$ groups;

R$^{3b}$ represents a hydrogen atom or a group selected from C$_1$-C$_6$-alkyl-, C$_3$-C$_6$-cycloalkyl-, 3- to 10-membered heterocycloalkyl-, aryl-, heteroaryl-, halo-C$_1$-C$_3$-alkyl-; wherein said C$_1$-C$_6$-alkyl-, C$_3$-C$_6$-cycloalkyl-, 3- to 10-membered heterocycloalkyl-, aryl- or heteroaryl- group is optionally substituted, identically or differently, with 1, 2, 3, 4 or 5 R$^4$ groups; or R$^3$ together with R$^{3a}$ or R$^{3b}$ represent a 3- to 10-memberered heterocycloalkyl- or a 4- to 10-membered heterocycloalkenyl- group, which is optionally substituted, one or more times, identically or differently, with halo-, hydroxyl-, cyano-;

R$^4$ represents halo-, hydroxy-, oxo- (O=), cyano-, nitro-, C$_1$-C$_6$-alkyl-, C$_2$-C$_6$-alkenyl-, C$_2$-C$_6$-alkynyl-, halo-C$_1$-C$_6$-alkyl-, C$_1$-C$_6$-alkoxy-, halo-C$_1$-C$_6$-alkoxy-, hydroxy-C$_1$-C$_6$-alkyl-, C$_1$-C$_6$-alkoxy-C$_1$-C$_6$-alkyl-, halo-C$_1$-C$_6$-alkoxy-C$_1$-C$_6$-alkyl-, R$^5$—O—, —C(=O)—R$^5$, —C(=O)—O—R$^5$, —O—C(=O)—R$^5$, —N(R$^{5a}$)—C(=O)—R$^{5b}$, —N(R$^{5a}$)—C(=O)—NR$^{5b}$R$^{5c}$, —NR$^{5a}$R$^{5b}$, —C(=O)—NR$^{5a}$R$^{5b}$, R$^5$—S—, R$^5$—S(=O)—, R$^5$—S(=O)$_2$—, —N(R$^{5a}$)—S(=O)—R$^{5b}$, —S(=O)—NR$^{5a}$R$^{5b}$, —N(R$^{5a}$)—S(=O)$_2$—R$^{5b}$, —S(=O)$_2$—NR$^{5a}$R$^{5b}$, —S(=O)(=NR$^{5a}$)R$^{5b}$, —S(=O)(=NR$^{5a}$)R$^{5b}$ or —N=S(=O)(R$^{5a}$)R$^{5b}$;

R$^5$ represents a hydrogen atom, a C$_1$-C$_6$-alkyl- or C$_3$-C$_6$-cycloalkyl- group;

R$^{5a}$ represents a hydrogen atom, a C$_1$-C$_6$-alkyl- or C$_3$-C$_6$-cycloalkyl- group;

R$^{5b}$ represents a hydrogen atom, a C$_1$-C$_6$-alkyl- or C$_3$-C$_6$-cycloalkyl- group;

R$^{5c}$ represents a hydrogen atom, a C$_1$-C$_6$-alkyl- or C$_3$-C$_6$-cycloalkyl- group; or R$^{5a}$ and R$^{5b}$ together may form a C$_2$-C$_6$-alkylene group, in which optionally one methylene can be replaced by —O—, —C(=O)—, —NH—, or —N(C$_1$-C$_4$-alkyl)-; or R$^{5a}$ and R$^{5c}$ together may form a C$_2$-C$_6$-alkylene group, in which optionally one methylene can be replaced by —O—, —C(=O)—, —NH—, or —N(C$_1$-C$_4$-alkyl)-; or R$^{5b}$ and R$^{5c}$ together may form a C$_2$-C$_6$-alkylene group, in which optionally one methylene can be replaced by —O—, —C(=O)—, —NH—, or —N(C$_1$-C$_4$-alkyl)-;

p represents an integer of 0, 1, 2 or 3;

q represents an integer of 0, 1, 2 or 3;

or a tautomer, a hydrate, a solvate, or a salt thereof, or a mixture of same.

2. A compound according to claim 1, wherein
R$^{1a}$ represents a hydrogen or halogen atom or a hydroxy-, cyano-, —NR$^{5a}$R$^{5b}$, C$_1$-C$_6$-alkyl- halo-C$_1$-C$_6$-alkyl- C$_1$-C$_6$-alkoxy-, or a halo-C$_1$-C$_6$-alkoxy- group;
R$^{1b}$ represents a hydrogen or halogen atom; and
R$^{1c}$ represents a hydrogen or halogen atom;
or a tautomer, a hydrate, a solvate, or a salt thereof, or a mixture of same.

3. A compound according to claim 1, wherein
one of R$^{2a}$ and R$^{2b}$
represents a hydrogen atom or a halogen atom or a group selected from: cyano-, C$_1$-C$_3$-alkyl-, halo-C$_1$-C$_3$-alkyl-; and
the other one of R$^{2a}$ and R$^{2b}$
represents a group selected from C$_1$-C$_6$-alkyl-, C$_3$-C$_6$-cycloalkyl-, 3- to 10-membered heterocycloalkyl-, 4- to 10-membered heterocycloalkenyl-, aryl-, heteroaryl-, —(CH$_2$)$_q$—X—(CH$_2$)$_p$—R$^3$; wherein said C$_1$-C$_6$-alkyl-, C$_3$-C$_6$-cycloalkyl-, 3- to 10-membered heterocycloalkyl-, 4- to 10-membered heterocycloalkenyl-, aryl- or heteroaryl- group is optionally substituted, identically or differently, with 1, 2 or 3 R$^4$ groups;
or a tautomer, a hydrate, a solvate, or a salt thereof, or a mixture of same.

4. A compound according to claim 1, wherein
Y represents N or CR$^{2a}$;
Z represents CR$^{2b}$;
p represents an integer of 0 or 1; and
q represents an integer of 0 or 1;
or a tautomer, a hydrate, a solvate, or a salt thereof, or a mixture of same.

5. A compound according to claim 1, wherein
X represents a bond or a bivalent group selected from: —C(=O)—, —C(=O)—O—, —C(=O)—(NR$^{3a}$)—, —(NR$^{3a}$)—C(=O)—, —(NR$^{3a}$)—C(=O)—(NR$^{3b}$)—, —O—C(=O)—(NR$^{3a}$)—, —(NR$^{3a}$)—C(=O)—O—;
R$^3$ represents a hydrogen atom or a group selected from C$_1$-C$_3$-alkyl-, 4- to 6-membered heterocycloalkyl-; wherein said C$_1$-C$_3$-alkyl- or 4- to 6-membered with one R$^4$ group;
R$^{3a}$ represents a hydrogen atom or a C$_1$-C$_3$-alkyl- group; wherein said C$_1$-C$_3$-alkyl- group is optionally substituted with one R$^4$ group;
R$^{3a}$ represents a hydrogen atom or a C$_1$-C$_3$-alkyl- group;
or a tautomer, a hydrate, a solvate, or a salt thereof, or a mixture of same.

6. A compound according to claim 1, wherein
R$^{1a}$ represents a C$_1$-C$_3$-alkoxy- group;
R$^{1b}$ represents a hydrogen atom;
R$^{1c}$ represents a hydrogen atom;
Y represents CR$^{2a}$;
Z represents CR$^{2b}$;
R$^{2a}$ represents a C$_1$-C$_3$-alkyl- group; and
R$^{2b}$ represents a C$_1$-C$_3$-alkyl- group;
or a tautomer, a hydrate, a solvate, or a salt thereof, or a mixture of same.

7. A compound according to claim 1, which is selected from the group consisting of:
6-[(6-ethyl-5-methyl-7H-pyrrolo[2,3-d]pyrimidin-4-yl)amino]-1,3-benzothiazol-2(3H)-one,
6-[(5-fluoro-7H-pyrrolo[2,3-d]pyrimidin-4-yl)amino]-1,3-benzothiazol-2(3H)-one,
4-[(2-oxo-2,3-dihydro-1,3-benzothiazol-6-yl)amino]-7H-pyrrolo[2,3-d]pyrimidine-5-carboxylic acid,
6-({5-[(4-methylpiperazin-1-yl)carbonyl]-7H-pyrrolo[2,3-d]pyrimidin-4-yl}amino)-1,3-benzothiazol-2(3H)-one,
N-isopropyl-4-[(2-oxo-2,3-dihydro-1,3-benzothiazol-6-yl)amino]-7H-pyrrolo[2,3-d]pyrimidine-5-carboxamide,
6-(7H-pyrrolo[2,3-d]pyrimidin-4-ylamino)-1,3-benzothiazol-2(3H)-one,
6-(1H-pyrazolo[3,4-d]pyrimidin-4-ylamino)-1,3-benzothiazol-2(3H)-one,
6-(9H-purin-6-ylamino)-1,3-benzothiazol-2(3H)-one,
ethyl 4-[(2-oxo-2,3-dihydro-1,3-benzothiazol-6-yl)amino]-7H-pyrrolo[2,3-d]pyrimidine-6-carboxylate,
6-{[6-(3-hydroxyprop-1-yn-1-yl)-7H-pyrrolo[2,3-d]pyrimidin-4-yl]amino}-1,3-benzothiazol-2(3H)-one,
4-[(2-oxo-2,3-dihydro-1,3-benzothiazol-6-yl)amino]-7H-pyrrolo[2,3-d]pyrimidine-5-carbonitrile,
6-[(6-ethyl-5-methyl-7H-pyrrolo[2,3-d]pyrimidin-4-yl)amino]-5-methoxy-1,3-benzothiazol-2(3H)-one,
6-[(6-methyl-7H-pyrrolo[2,3-d]pyrimidin-4-yl)amino]-1,3-benzothiazol-2(3H)-one, 6-[(5-methyl-7H-pyrrolo[2,3-d]pyrimidin-4-yl)amino]-1,3-benzothiazol-2(3H)-one, 6-[(6-chloro-7H-pyrrolo[2,3-d]pyrimidin-4-yl)amino]-1,3-benzothiazol-2(3H)-one, 6-{[6-(3-hydroxypropyl)-7H-pyrrolo[2,3-d]pyrimidin-4-yl]amino}-1,3-benzothiazol-2(3H)-one, 6-[(6-bromo-7H-pyrrolo[2,3-d]pyrimidin-4-yl)amino]-5-methoxy-1,3-benzothiazol-2(3H)-one, 5-methoxy-6-(7H-pyrrolo[2,3-d]pyrimidin-4-ylamino)-1,3-benzothiazol-2(3H)-one, N,N-dimethyl-4-[(2-oxo-2,3-dihydro-1,3-benzothiazol-6-yl)amino]-7H-pyrrolo[2 3-d]pyrimidine-5-carboxamide, 6-[(6-isobutyl-5-isopropyl-7H-pyrrolo[2,3-d]pyrimidin-4-yl)amino]-1,3-benzothiazol-2(3H)-one, 6-[(5-ethyl-6-propyl-7H-pyrrolo[2,3-d]pyrimidin-4-yl)amino]-1,3-benzathiazol-2(3H)-one, 6-({6-[(4-chlorophenyl)sulfonyl]-7H-pyrrolo[2,3-d]pyrimidin-4-yl}amino)-1,3-benzothiazol-2(3H)-one, 6-({6-[(4-methylphenyl)sulfonyl]-7H-pyrrolo[2,3-d]pyrimidin-4-yl}amino)-1,3-benzothiazol-2(3H)-one, ethyl 4-[(5-methoxy-2-oxo-2,3-dihydro-1,3-benzothiazol-6-yl)amino]-7H-pyrrolo[2,3-d]pyrimidine-6-carboxylate, 4-[(5-methoxy-2-oxo-2,3-dihydro-1,3-benzothiazol-6-yl)amino]-7H-pyrrolo[2,3-d]pyrimidine-6-carboxylic acid, 6-[(5-bromo-7H-pyrrolo[2,3-d]pyrimidin-4-yl)amino]-1,3-benzothiazol-2(3H)-one, 6-[(5-fluoro-7H-pyrrolo[2,3-d]pyrimidin-4-yl)amino]-5-methoxy-1,3-benzothiazol-2(3H)-one, 6-[(5-ethyl-6-propyl-7H-pyrrolo[2,3-d]pyrimidin-4-yl)amino]-5-methoxy-1,3-benzothiazol-2(3H)-one, or a tautomer, a hydrate, a solvate, or a salt thereof, or a mixture of same.

8. A pharmaceutical composition comprising a compound of general formula I, or a stereoisomer, a tautomer, a hydrate, a solvate, or a salt thereof, particularly a pharmaceutically acceptable salt thereof, or a mixture of same, according to claim 1, and a pharmaceutically acceptable diluent or carrier.

9. A method of preparing a compound of general formula I according to claim 1, in which method an intermediate compound of general formula II:

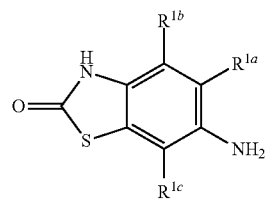

in which $R^{1a}$, $R^{1b}$, and $R^{1c}$ are as defined in claim 1 is allowed to react with an intermediate compound of general formula IIIb:

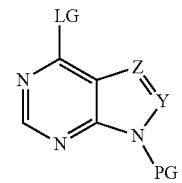

in which Y and Z are as defined in claim 1, LG represents a leaving group and PG represents a protective group or a hydrogen atom;

thus providing a compound of general formula I:

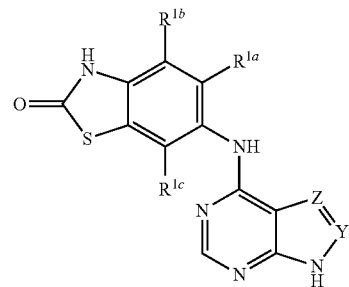

in which $R^{1a}$, $R^{1b}$, $R^{1c}$, $R^{2a}$ and Y are as defined in claim 1.

* * * * *